(12) United States Patent
Hirano et al.

(10) Patent No.: US 10,838,301 B2
(45) Date of Patent: Nov. 17, 2020

(54) RESIST COMPOSITION, METHOD OF FORMING RESIST PATTERN, FLUORINE-CONTAINING COMPOUND, AND COMPOUND

(71) Applicant: TOKYO OHKA KOGYO CO., LTD., Kawasaki (JP)

(72) Inventors: Tomoyuki Hirano, Kawasaki (JP); Takaaki Kaiho, Kawasaki (JP)

(73) Assignee: Tokyo Ohka Kogyo Co., Ltd., Kawasaki (JP)

( * ) Notice: Subject to any disclaimer, the term of this patent is extended or adjusted under 35 U.S.C. 154(b) by 134 days.

(21) Appl. No.: 15/928,488

(22) Filed: Mar. 22, 2018

(65) Prior Publication Data
US 2018/0284606 A1    Oct. 4, 2018

(30) Foreign Application Priority Data

Mar. 29, 2017    (JP) ................................ 2017-066270

(51) Int. Cl.
| | | |
|---|---|---|
| G03F 7/04 | (2006.01) |
| G03F 7/38 | (2006.01) |
| C08F 222/18 | (2006.01) |
| C08F 224/00 | (2006.01) |
| C08F 214/18 | (2006.01) |
| C08F 212/04 | (2006.01) |
| G03F 7/004 | (2006.01) |
| C08F 20/28 | (2006.01) |
| C07C 69/708 | (2006.01) |
| G03F 7/32 | (2006.01) |
| G03F 7/16 | (2006.01) |
| G03F 7/20 | (2006.01) |
| G03F 7/039 | (2006.01) |
| C07C 69/73 | (2006.01) |

(52) U.S. Cl.
CPC .......... *G03F 7/0046* (2013.01); *C07C 69/708* (2013.01); *C07C 69/73* (2013.01); *C08F 20/28* (2013.01); *C08F 212/04* (2013.01); *C08F 214/186* (2013.01); *C08F 222/18* (2013.01); *C08F 224/00* (2013.01); *G03F 7/0045* (2013.01); *G03F 7/0392* (2013.01); *G03F 7/0397* (2013.01); *G03F 7/162* (2013.01); *G03F 7/168* (2013.01); *G03F 7/2006* (2013.01); *G03F 7/2041* (2013.01); *G03F 7/322* (2013.01); *G03F 7/38* (2013.01)

(58) Field of Classification Search
CPC ........ G03F 7/0397; G03F 7/0046; G03F 7/38; G03F 7/2041; G03F 7/2006; C08F 222/18; C08F 224/00; C08F 214/186; C08F 212/04
See application file for complete search history.

(56) References Cited

U.S. PATENT DOCUMENTS

| | | | | |
|---|---|---|---|---|
| 7,494,762 B2 * | 2/2009 | Irie | ........................ | G03F 7/2041 430/270.1 |
| 7,514,204 B2 * | 4/2009 | Hatakeyama | ......... | G03F 7/0045 430/270.1 |
| 7,527,911 B2 * | 5/2009 | Wada | .................... | G03F 7/0046 430/270.1 |
| 8,592,540 B2 * | 11/2013 | Mori | ..................... | C07C 235/06 430/270.1 |
| 2010/0310985 A1 | 12/2010 | Mori et al. | | |
| 2012/0040294 A1 * | 2/2012 | Maeda | .................... | C08F 20/22 430/325 |
| 2012/0064459 A1 * | 3/2012 | Maeda | .................... | C08F 20/26 430/285.1 |

(Continued)

FOREIGN PATENT DOCUMENTS

| | | |
|---|---|---|
| JP | A-2010-275498 | 12/2010 |
| JP | B-5386236 | 1/2014 |

(Continued)

OTHER PUBLICATIONS

D. Gil et al., "First microprocessors with Immersion Lithography", Proceedings of SPIE vol. 5754, pp. 119-128, 2005.

*Primary Examiner* — John S Chu
(74) *Attorney, Agent, or Firm* — Knobbe Martens Olson & Bear LLP

(57) ABSTRACT

A resist composition which generates acid upon exposure and exhibits changed solubility in a developing solution under action of acid, the resist composition including: a base component which exhibits changed solubility in a developing solution under action of acid and a fluorine additive component which exhibits decomposability to an alkali developing solution, the fluorine additive component including a fluorine resist component having a structural unit derived from a compound represented by general formula (f1-1) in which W represents a polymerizable group-containing group; $Rf^1$ and $Rf^2$ each independently represents a hydrogen atom or an electron-withdrawing group; and $Rf^3$ represents a hydrocarbon group

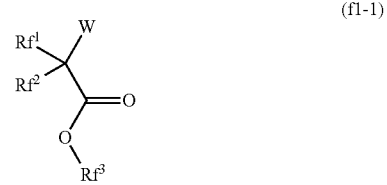

(f1-1)

5 Claims, 1 Drawing Sheet

(56) References Cited

U.S. PATENT DOCUMENTS

2012/0077126 A1\* 3/2012 Mori ................... C07C 69/653
 430/285.1
2012/0129108 A1\* 5/2012 Aqad ................... C07C 63/72
 430/325

FOREIGN PATENT DOCUMENTS

| JP | B-5569402 | 8/2014 |
| JP | B-5713011 | 5/2015 |

\* cited by examiner

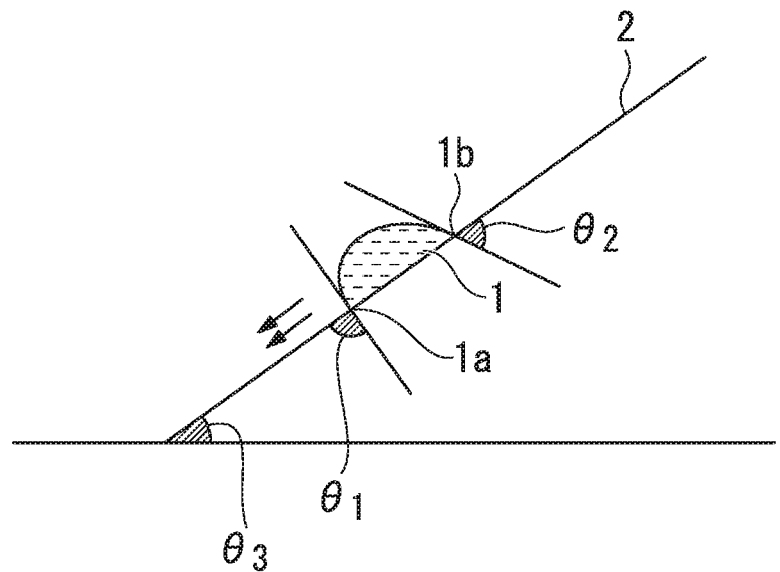

RESIST COMPOSITION, METHOD OF FORMING RESIST PATTERN, FLUORINE-CONTAINING COMPOUND, AND COMPOUND

TECHNICAL FIELD

The present invention relates to a resist composition, a method of forming a resist pattern, a fluorine-containing polymeric compound, and a compound.

Priority is claimed on Japanese Patent Application No. 2017-066270, filed Mar. 29, 2017, the content of which is incorporated herein by reference.

DESCRIPTION OF RELATED ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

For miniaturization of semiconductor devices, shortening of the wavelength of the exposure light source, and increasing of the numerical aperture (NA) of the projector lens have progressed. Currently, exposure apparatuses in which an ArF excimer laser having a wavelength of 193 nm is used as an exposure light source and NA=0.84 have been developed. As shortening the wavelength of the exposure light source progresses, it is required to improve various lithography properties of the resist material, such as the sensitivity to the exposure light source and a resolution capable of reproducing patterns of minute dimensions. As a resist material which satisfies these conditions, a chemically amplified resist is used, which includes a base resin that exhibits a changed solubility in an alkali developing solution under action of acid and an acid generator that generates acid upon exposure.

Currently, resins that contain structural units derived from (meth)acrylate esters within the main chain (acrylic resins) are now widely used as base resins for resists that use ArF excimer laser lithography, as they exhibit excellent transparency in the vicinity of 193 nm.

Here, the term "(meth)acrylic acid" is a generic term that includes either or both of acrylic acid having a hydrogen atom bonded to the α-position and methacrylic acid having a methyl group bonded to the α-position. The term "(meth) acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position.

As a technique for further improving the resolution, a lithography method called liquid immersion lithography (hereafter, frequently referred to as "immersion exposure") is known in which exposure (immersion exposure) is conducted in a state where the region between the lens and the resist layer formed on a wafer is filled with a solvent (an immersion medium) that has a larger refractive index than the refractive index of air (see for example, Non-Patent Document 1).

According to this type of immersion exposure, it is considered that higher resolutions equivalent to those obtained using a shorter wavelength light source or a larger NA lens can be obtained using the same exposure light source wavelength, with no lowering of the depth of focus. Furthermore, immersion exposure can be conducted using a conventional exposure apparatus. As a result, it is expected that immersion exposure will enable the formation of resist patterns of higher resolution and superior depth of focus at lower costs. Accordingly, in the production of semiconductor devices, which requires enormous capital investment, immersion exposure is attracting considerable attention as a method that offers significant potential to the semiconductor industry, both in terms of cost and in terms of lithography properties such as resolution.

Immersion lithography is effective in forming patterns having various shapes. Further, immersion exposure is expected to be capable of being used in combination with currently studied super-resolution techniques, such as phase shift method and modified illumination method. Currently, as the immersion exposure technique, technique using an ArF excimer laser as an exposure source is being actively studied. Further, water is mainly used as the immersion medium.

It is known that a compound containing a fluorine atom is added to a resist composition used in immersion lithography (see, for example, Patent Literatures 1 to 4).

DOCUMENTS OF RELATED ART

Patent Literature

[Patent Literature 1] Japanese Patent No. 5386236
[Patent Literature 2] Japanese Unexamined Patent Application, First Publication No. 2010-275498
[Patent Literature 3] Japanese Patent No. 5569402
[Patent Literature 4] Japanese Patent No. 5713011

Non-Patent Documents

[Non-Patent Document 1] Proceedings of SPIE (U.S.), vol. 5754, pp. 119-128 (2005)

SUMMARY OF THE INVENTION

In the aforementioned immersion exposure, a resist material is required which exhibits not only general lithography properties (e.g., sensitivity, resolution, etching resistance and the like), but also properties suited for immersion lithography. For example, in immersion exposure, when the resist film comes in contact with the immersion medium, elution of a substance contained in the resist film into the immersion medium occurs. This elution of a substance causes phenomenon such as degeneration of the resist film and change in the refractive index of the immersion medium, thereby adversely affecting the lithography properties. The amount of the eluted substance is affected by the properties of the resist film surface (e.g., hydrophilicity, hydrophobicity, and the like). For example, by enhancing the hydrophobicity of the resist film surface, the elution of a substance can be reduced. Further, when the immersion medium is water, and immersion exposure is performed using a scanning-type immersion exposure apparatus as disclosed in Non-Patent Document 1, a water tracking ability in which the immersion medium is capable of tracking the movement of the lens is required. When the water tracking ability is low, the exposure speed becomes low, and as a result, there is a possibility that the productivity is adversely affected. It is presumed that the water tracking ability can be improved by enhancing the hydrophobicity of the resist film (rendering the resist film hydrophobic).

Accordingly, it is presumed that the above-described characteristic problems of immersion lithography, which require a reduction in substance elution and an improvement in the water tracking ability, can be addressed by enhancing the hydrophobicity of the resist film surface.

However, if the resist film is simply rendered hydrophobic, then adverse effects are seen on the lithography properties. For example, as the hydrophobicity of the resist film is increased, defects tend to be generated more readily on the surface of the formed resist pattern following alkali developing. Particularly in the case where a pattern is formed using alkali developing process, defects are likely to be generated at unexposed portions.

The term "defects" refers to general deficiencies within a resist film that are detected when observed from directly above the developed resist pattern using, for example, a surface defect detection apparatus (product name: "KLA") manufactured by KLA-TENCOR Corporation. Examples of these deficiencies include deficiencies caused by adhesion of foreign matters and precipitates on the surface of the resist pattern, such as post-developing scum (residual resist), foam and dust; deficiencies related to resist pattern shape, such as bridges formed between line patterns, and filling-up of holes of a contact hole pattern; and color irregularities of a pattern. In the resist compositions described in Patent Literatures 1 to 4, a fluorine-containing polymeric compound is added to enhance the water repellency during exposure, and a hydrophilic group is formed during developing to enhance hydrophilicity and reduce defects.

In recent years, in the case where immersion lithography is conducted using a scan-type immersion lithography apparatus, due to the increase of the scanning speed, generation of watermark defects is becoming a problem. Therefore, there are demands for rendering the resist film more hydrophobic. However, conventional resist compositions do not have satisfactory water repellency for responding to the increase in the scanning speed.

The present invention takes the above circumstances into consideration, with an object of providing a resist composition which has high water repellency, and is capable of reducing generation of defects; a method of forming a resist pattern using the resist composition; a fluorine-containing polymeric compound useful as an additive for the resist composition; and a compound useful for producing the fluorine-containing polymeric compound.

A first aspect of the present invention is a resist composition which generates acid upon exposure and exhibits changed solubility in a developing solution under action of acid, the resist composition including: a base component (A) which exhibits changed solubility in a developing solution under action of acid and a fluorine additive component (F) which exhibits decomposability to an alkali developing solution, the fluorine additive component (F) including a fluorine resist component (F1) having a structural unit (f1) derived from a compound represented by general formula (f1-1) shown below.

[Chemical Formula 1]

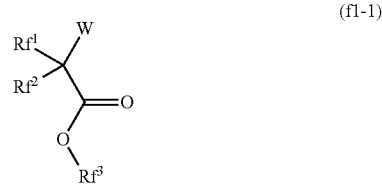

In the formula, W represents a polymerizable group-containing group; $Rf^1$ and $Rf^2$ each independently represents a hydrogen atom or an electron-withdrawing group; $Rf^3$ represents a hydrocarbon group which may have a substituent; provided that at least one of $Rf^1$ to $Rf^3$ has a fluorine atom; in the case where $Rf^3$ is an aliphatic hydrocarbon group which may have a substituent, $Rf^3$ has 5 or more carbon atoms; and in the case where $Rf^3$ is an aromatic hydrocarbon group which may have a substituent, 3 or more hydrogen atoms of the aromatic ring are substituted with electron-withdrawing groups, and at least one of $Rf^1$ and $Rf^2$ is an electron-withdrawing group.

A second aspect of the present invention is a method of forming a resist pattern, including: using a resist composition according to the first aspect to form a resist film on a substrate, exposing the resist film to exposure, and developing the exposed resist film to form a resist pattern.

A third aspect of the present invention is a fluorine-containing polymeric compound having a structural unit (f1) derived from a compound represented by general formula (f1-1) shown below.

[Chemical Formula 2]

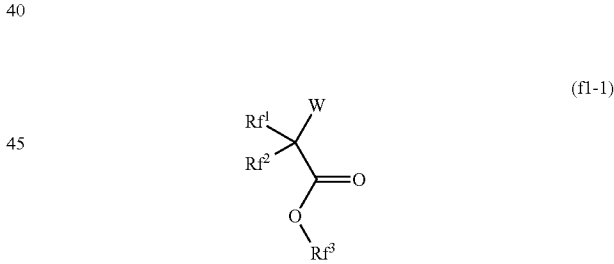

In the formula, W represents a polymerizable group-containing group; $Rf^1$ and $Rf^2$ each independently represents a hydrogen atom or an electron-withdrawing group; $Rf^3$ represents a hydrocarbon group which may have a substituent; provided that at least one of $Rf^1$ to $Rf^3$ has a fluorine atom; in the case where $Rf^3$ is an aliphatic hydrocarbon group which may have a substituent, $Rf^3$ has 5 or more carbon atoms; and in the case where $Rf^3$ is an aromatic hydrocarbon group which may have a substituent, 3 or more hydrogen atoms of the aromatic ring are substituted with electron-withdrawing groups, and at least one of $Rf^1$ and $Rf^2$ is an electron-withdrawing group.

A fourth aspect of the present invention is a compound represented by general formula (f1-1).

[Chemical Formula 3]

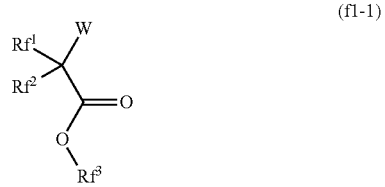

(f1-1)

In the formula, W represents a polymerizable group-containing group; Rf¹ and Rf² each independently represents a hydrogen atom or an electron-withdrawing group; Rf³ represents a hydrocarbon group which may have a substituent; provided that at least one of Rf¹ to Rf³ has a fluorine atom; in the case where Rf³ is an aliphatic hydrocarbon group which may have a substituent, Rf³ has 5 or more carbon atoms; and in the case where Rf³ is an aromatic hydrocarbon group which may have a substituent, 3 or more hydrogen atoms of the aromatic ring are substituted with electron-withdrawing groups, and at least one of Rf¹ and Rf² is an electron-withdrawing group.

According to the present invention, there are provided a resist composition which has high water repellency, and is capable of reducing generation of defects; a method of forming a resist pattern using the resist composition; a fluorine-containing polymeric compound useful as an additive for the resist composition; and a compound useful for producing the fluorine-containing polymeric compound.

BRIEF DESCRIPTION OF THE DRAWINGS

FIG. 1 is an explanatory diagram of an advancing angle (θ1), a receding angle (θ2) and a sliding angle (θ3).

DETAILED DESCRIPTION OF THE INVENTION

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified.

The term "alkylene group" includes linear, branched or cyclic, divalent saturated hydrocarbon, unless otherwise specified. The same applies for the alkyl group within an alkoxy group.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with a fluorine atom.

The term "structural unit" refers to a monomer unit that contributes to the formation of a polymeric compound (resin, polymer, copolymer).

A "structural unit derived from an acrylate ester" refers to a structural unit that is formed by the cleavage of the ethylenic double bond of an acrylate ester.

An "acrylate ester" refers to a compound in which the terminal hydrogen atom of the carboxy group of acrylic acid ($CH_2=CH-COOH$) has been substituted with an organic group.

The acrylate ester may have the hydrogen atom bonded to the carbon atom on the α-position substituted with a substituent. The substituent ($R^{\alpha}$) with which the hydrogen atom bonded to the carbon atom at the α-position is substituted is an atom other than the hydrogen atom or a group, and examples thereof include an alkyl group having from 1 to 5 carbon atoms, a halogenated alkyl group having from 1 to 5 carbon atoms, and a hydroxyalkyl group. A carbon atom on the α-position of an acrylate ester refers to the carbon atom bonded to the carbonyl group, unless specified otherwise.

Hereafter, an acrylate ester having the hydrogen atom bonded to the carbon atom on the α-position substituted with a substituent is sometimes referred to as "α-substituted acrylate ester". Further, acrylate esters and α-substituted acrylate esters are collectively referred to as "(α-substituted) acrylate ester".

As the alkyl group as a substituent on the α-position, a linear or branched alkyl group is preferable, and specific examples include alkyl groups of 1 to 5 carbon atoms, such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group as the substituent on the α-position include groups in which part or all of the hydrogen atoms of the aforementioned "alkyl group as the substituent on the α-position" are substituted with halogen atoms. Examples of the halogen atom include a fluorine atom, a chlorine atom, a bromine atom and an iodine atom, and a fluorine atom is particularly desirable.

Specific examples of the hydroxyalkyl group as the substituent on the α-position include groups in which part or all of the hydrogen atoms of the aforementioned "alkyl group as the substituent on the α-position" are substituted with a hydroxy group. The number of hydroxy groups within the hydroxyalkyl group is preferably 1 to 5, and most preferably 1.

The case of describing "may have a substituent" includes both of the case where the hydrogen atom (—H) is substituted with a monovalent group and the case where the methylene group (—$CH_2$—) is substituted with a divalent group.

The term "exposure" is used as a general concept that includes irradiation with any form of radiation.

(Resist Composition)

A first aspect of the present invention is a resist composition which generates acid upon exposure and exhibits changed solubility in a developing solution under action of acid, the resist composition including: a base component (A) (hereafter, sometimes referred to as "component (A)") which exhibits changed solubility in a developing solution under action of acid and a fluorine additive component (F) (hereafter, sometimes referred to as "component (F)") which exhibits decomposability to an alkali developing solution, the fluorine additive component (F) including a fluorine resist component (F1) having a structural unit (f1) derived from a compound represented by general formula (f1-1) shown below.

In the present embodiment, the component (A) may be constituted of a single polymeric compound, or a mixture of a plurality of polymeric compounds.

When a resist film is formed using the resist composition and the formed resist film is subjected to a selective exposure, acid is generated at exposed portions, and the generated acid acts on the component (A) to change the solubility of the component (A) in a developing solution, whereas the solubility of the component (A) in a developing solution is not changed at unexposed portions, thereby generating difference in solubility in a developing solution between exposed portions and unexposed portions. Therefore, by subjecting the resist film to development, the exposed portions are dissolved and removed to form a positive-tone resist pattern in the case of a positive resist, whereas the unexposed portions are dissolved and removed to form a negative-tone resist pattern in the case of a negative resist.

In the present specification, a resist composition which forms a positive resist pattern by dissolving and removing the exposed portions is called a positive resist composition, and a resist composition which forms a negative resist pattern by dissolving and removing the unexposed portions is called a negative resist composition.

In the present embodiment, the resist composition may be either a positive resist composition or a negative resist composition.

Further, in the present invention, the resist composition is applicable to an alkali developing process using an alkali developing solution in the developing treatment, or a solvent developing process using a developing solution containing an organic solvent (organic developing solution) in the developing treatment, but is preferably applicable to an alkali developing process.

In the present embodiment, the resist composition has a function of generating acid upon exposure, and in the resist composition, the component (A) may generate acid upon exposure, or an additive component other than the component (A) may generate acid upon exposure.

More specifically, in the present embodiment, the resist composition may be a resist composition (1) containing an acid generator component (B) which generates acid upon exposure (hereafter, referred to as "component (B)";

a resist composition (2) in which the component (A) is a component which generates acid upon exposure; or a resist composition (3) in which the component (A) is a component which generates acid upon exposure, and further containing an acid generator component (B).

That is, when the resist composition of the present invention is the aforementioned resist composition (2) or (3), the component (A) is a "base component which generates acid upon exposure and exhibits changed solubility in a developing solution under action of acid". In the case where the component (A) is a base component which generates acid upon exposure and exhibits changed solubility in a developing solution under action of acid, the component (A1) described later is preferably a polymeric compound which generates acid upon exposure and exhibits changed solubility in a developing solution under action of acid. As the polymeric compound, a resin having a structural unit which generates acid upon exposure can be used. As the structural unit which generates acid upon exposure, a conventional structural unit can be used.

In the present embodiment, it is particularly desirable that the resist composition is the aforementioned resist composition (1).

<Component (A)>

In the present invention, the term "base component" refers to an organic compound capable of forming a film, and is preferably an organic compound having a molecular weight of 500 or more. When the organic compound has a molecular weight of 500 or more, the film-forming ability is improved, and a photosensitive resin pattern of nano level can be easily formed.

The organic compound used as the base component is broadly classified into non-polymers and polymers.

In general, as a non-polymer, any of those which have a molecular weight in the range of 500 to less than 4,000 is used. Hereafter, a "low molecular weight compound" refers to a non-polymer having a molecular weight in the range of 500 to less than 4,000.

As a polymer, any of those which have a molecular weight of 1,000 or more is generally used. Hereafter, a "resin" refers to a polymer having a molecular weight of 1,000 or more.

As the molecular weight of the polymer, the weight average molecular weight in terms of the polystyrene equivalent value determined by gel permeation chromatography (GPC) is used.

As the component (A'), a resin, a low molecular weight compound, or a combination thereof may be used.

The component (A) may be a resin that exhibits increased solubility in a developing solution under action of acid or a resin that exhibits decreased solubility in a developing solution under action of acid.

In the present invention, the component (A) may be a component that generates acid upon exposure.

In the present invention, the component (A) preferably includes a resin component (A1) (hereafter, sometimes referred to as "component (A1))" which has at least one structural unit selected from the group consisting of the structural units (a10), (a1), (a2) and (a3) described later.

(Structural Unit (a1))

The structural unit (a1) is a structural unit containing an acid decomposable group that exhibits increased polarity by the action of acid.

The term "acid decomposable group" refers to a group in which at least a part of the bond within the structure thereof is cleaved by the action of an acid.

Examples of acid decomposable groups which exhibit increased polarity by the action of an acid include groups which are decomposed by the action of an acid to form a polar group.

Examples of the polar group include a carboxy group, a hydroxy group, an amino group and a sulfo group ($-SO_3H$). Among these, a polar group containing —OH in the structure thereof (hereafter, referred to as "OH-containing polar group") is preferable, a carboxy group or a hydroxy group is more preferable, and a carboxy group is particularly desirable.

More specifically, as an example of an acid decomposable group, a group in which the aforementioned polar group has been protected with an acid dissociable group (such as a group in which the hydrogen atom of the OH-containing polar group has been protected with an acid dissociable group) can be given.

The "acid dissociable group" refers to both (i) a group in which the bond between the acid dissociable group and the adjacent atom is cleaved by the action of acid; and (ii) a group in which one of the bonds is cleaved by the action of acid, and then a decarboxylation reaction occurs, thereby cleaving the bond between the acid dissociable group and the adjacent atom.

It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1) is increased. By the increase in the polarity, the solubility in an alkali developing solution changes, and the solubility in an alkali developing solution is relatively increased, whereas the solubility in an organic developing solution is relatively decreased.

Examples of the acid dissociable group include groups which have been proposed as acid dissociable groups for the base resin of a conventional chemically amplified resist composition.

Specific examples of acid dissociable groups for the base resin of a conventional chemically amplified resist composition include "acetal-type acid dissociable group", "tertiary alkyl ester-type acid dissociable group" and "tertiary alkyloxycarbonyl acid dissociable group" described below.

Acetal-Type Acid Dissociable Group

Examples of the acid dissociable group for protecting the carboxy group or hydroxy group as a polar group include the acid dissociable group represented by general formula (a1-r-1) shown below (hereafter, referred to as "acetal-type acid dissociable group").

[Chemical Formula 4]

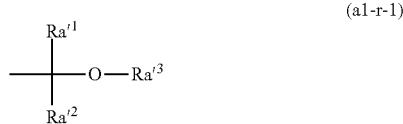

(a1-r-1)

In the formula, $Ra'^1$ and $Ra'^2$ each independently represents a hydrogen atom or an alkyl group; and $Ra'^3$ represents a hydrocarbon group, provided that $Ra'^3$ may be bonded to $Ra'^1$ or $Ra'^2$.

In the formula (a1-r-1), it is preferable that at least one of $Ra'^1$ and $Ra'^2$ represents a hydrogen atom, and it is more preferable that both of $Ra'^1$ and $Ra'^2$ represent a hydrogen atom.

In the case where $Ra'^1$ or $Ra'^2$ is an alkyl group, as the alkyl group, the same alkyl groups as those described above the for the substituent which may be bonded to the carbon atom on the α-position of the aforementioned α-substituted acrylate ester can be mentioned, and an alkyl group of 1 to 5 carbon atoms is preferable. Specific examples include linear or branched alkyl groups. Specific examples of the alkyl group include a methyl group, an ethyl group, a propyl group, an isopropyl group, an n-butyl group, an isobutyl group, a tert-butyl group, a pentyl group, an isopentyl group and a neopentyl group. Of these, a methyl group or an ethyl group is preferable, and a methyl group is particularly preferable.

In formula (a1-r-1), examples of the hydrocarbon group for $Ra'^3$ include a linear or branched alkyl group and a cyclic hydrocarbon group.

The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5. Specific examples include an isopropyl group, an isobutyl group, a tert-butyl group, an isopentyl group, a neopentyl group a 1,1-diethylpropyl group and a 2,2-dimethylbutyl group. Among these, an isopropyl group is preferable.

In the case where $Ra'^3$ represents a cyclic hydrocarbon group, the cyclic hydrocarbon group may be an aliphatic hydrocarbon group or an aromatic hydrocarbon group, and may be polycyclic or monocyclic.

As the monocyclic aliphatic hydrocarbon group, a group in which 1 hydrogen atom has been removed from a monocycloalkane is preferable. The monocycloalkane preferably has 3 to 6 carbon atoms, and specific examples thereof include cyclopentane and cyclohexane.

As the polycyclic aliphatic hydrocarbon group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

When the monovalent hydrocarbon group for $Ra'^3$ is an aromatic hydrocarbon group, the aromatic hydrocarbon group is a hydrocarbon group having at least one aromatic ring.

The aromatic ring is not particularly limited, as long as it is a cyclic conjugated compound having $(4n+2)\pi$ electrons, and may be either monocyclic or polycyclic. The aromatic ring preferably has 5 to 30 carbon atoms, more preferably 5 to 20, still more preferably 6 to 15, and most preferably 6 to 12.

Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group for $Ra'^3$ include a group in which one hydrogen atom has been removed from the aforementioned aromatic hydrocarbon ring or aromatic hetero ring (aryl group or heteroaryl group); a group in which one hydrogen atom has been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (an arylalkyl group such as a benzyl group, a phenethyl group, a 1-naphthylmethyl group, a 2-naphthylmethyl group, a 1-naphthylethyl group, or a 2-naphthylethyl group). The alkylene group bonded to the aforementioned aromatic hydrocarbon ring or the aromatic hetero ring preferably has 1 to 4 carbon atoms, more preferably 1 or 2 carbon atoms, and most preferably 1 carbon atom.

The cyclic hydrocarbon group for $Ra'^3$ may have a substituent. Examples of the substituent include $-R^{P1}$, $-R^{P2}-O-R^{P1}$, $-R^{P2}-CO-R^{P1}$, $-R^{P2}-CO-OR^{P1}$, $-R^{P2}-O-CO-R^{P1}$, $-R^{P2}-OH$, $-R^{P2}-CN$ and $-R^{P2}COOH$ (hereafter, these substituents are sometimes collectively referred to as "$Ra^{05}$").

Here, $R^{P1}$ is a monovalent chain saturated hydrocarbon group having 1 to 10 carbon atoms, a monovalent aliphatic cyclic saturated hydrocarbon group having 3 to 20 carbon atoms, or a monovalent aromatic hydrocarbon group having 6 to 30 carbon atoms. Further, $R^{P2}$ is a single bond, a divalent chain saturated hydrocarbon group having 1 to 10 carbon atoms, a divalent aliphatic cyclic saturated hydrocarbon group having 3 to 20 carbon atoms, or a divalent aromatic hydrocarbon group having 6 to 30 carbon atoms.

Here, a portion or all of the hydrogen atoms having the chain saturated hydrocarbon group, the aliphatic cyclic saturated hydrocarbon group, and the aromatic hydrocarbon group for $R^{P1}$ and $R^{P2}$ may be substituted with a fluorine atom. The aliphatic cyclic hydrocarbon group may have 1 or more substituents of 1 kind, or 1 or more substituents of a plurality of kinds.

Examples of the monovalent chain saturated hydrocarbon group having 1 to 10 carbon atoms include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, and a cyclododecyl group; and a polycyclic aliphatic saturated hydrocarbon group such as a bicyclo[2.2.2]octanyl group, a tricyclo[5.2.1.02,6]decanyl group, a tricyclo[3.3.1.13,7]decanyl group, a tetracyclo[6.2.1.13,6.02,7]dodecanyl group, and an adamantyl group.

Examples of the monovalent aromatic hydrocarbon group having 6 to 30 carbon atoms include a group obtained by removing one hydrogen atom from the aromatic hydrocarbon ring such as benzene, biphenyl, fluorene, naphthalene, anthracene, and phenanthrene.

In the case where $Ra'^3$ is bonded to $Ra'^1$ or $Ra'^2$ to form a ring, the cyclic group is preferably a 4 to 7-membered ring, and more preferably a 4 to 6-membered ring. Specific examples of the cyclic group include tetrahydropyranyl group and tetrahydrofuranyl group.

Tertiary Alkyl Ester-Type Acid Dissociable Group

Examples of the acid dissociable group for protecting the carboxy group as a polar group include the acid dissociable group represented by general formula (a1-r-2) shown below.

Among the acid dissociable groups represented by general formula (a1-r-2), for convenience, a group which is constituted of alkyl groups is referred to as "tertiary ester-type acid dissociable group".

[Chemical Formula 5]

(a1-r-2)

In the formula, $Ra'^4$ to $Ra'^6$ each independently represents a hydrocarbon group, provided that $Ra'^5$ and $Ra'^6$ may be mutually bonded to form a ring.

Examples of the hydrocarbon group for $Ra'^4$ include a linear or branched alkyl group, a chain or cyclic alkenyl group, and a cyclic hydrocarbon group.

The linear or branched alkyl group and the cyclic hydrocarbon group (monocyclic aliphatic hydrocarbon group, polycyclic aliphatic hydrocarbon group or aromatic hydrocarbon group) for $Ra'^4$ are the same as defined for $Ra'^3$.

The chain or cyclic alkenyl group for $Ra'^4$ is preferably an alkenyl group having 2 to 10 carbon atoms.

The hydrocarbon group for $Ra'^5$ and $Ra'^6$ is the same as defined for $Ra'^3$.

In the case where $Ra'^5$ and $Ra'^6$ are mutually bonded to form a ring, a group represented by general formula (a1-r2-1) shown below, a group represented by general formula (a1-r2-2) shown below, and a group represented by general formula (a1-r2-3) shown below may be given as preferable examples.

On the other hand, in the case where $Ra'^4$ to $Ra'^6$ are not mutually bonded and independently represent a hydrocarbon group, the group represented by general formula (a1-r2-4) shown below may be given as a preferable example.

[Chemical Formula 6]

(a1-r2-1)

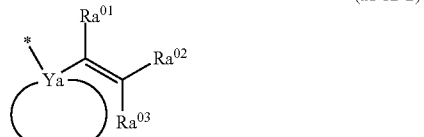

(a1-r2-2)

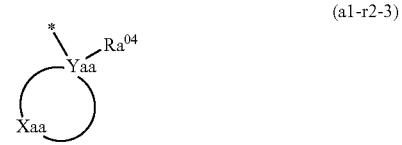

(a1-r2-3)

(a1-r2-4)

In formula (a1-r2-1), $Ra'^{10}$ represents an alkyl group of 1 to 10 carbon atoms; $Ra'^{11}$ is a group which forms an aliphatic cyclic group together with a carbon atom having $Ra'^{10}$ bonded thereto. In formula (a1-r2-2), Ya represents a carbon atom; Xa represents a group which forms a cyclic hydrocarbon group together with Ya, provided that part or all of the hydrogen atoms of the cyclic hydrocarbon group may be substituted;

$Ra^{01}$ to $Ra^{03}$ each independently represents a hydrogen atom, a monovalent saturated chain hydrocarbon group of 1 to 10 carbon atoms or a monovalent saturated aliphatic cyclic hydrocarbon group of 3 to 20 carbon atoms, provided that part or all of the hydrogen atoms of the saturated chain hydrocarbon or the saturated aliphatic cyclic hydrocarbon may be substituted; two or more of $Ra^{01}$ to $Ra^{03}$ may be mutually bonded to form a cyclic structure; and * represents a valence bond. In formula (a1-r2-3), Yaa represents a carbon atom; Xaa represents a group which forms an aliphatic cyclic group together with Yaa; $Ra^{04}$ represents an aromatic hydrocarbon group which may have a substituent; and * represents a valence bond. In formula (a1-r2-4), $Ra'^{12}$ and $Ra'^{13}$ each independently represents a hydrogen atom or a monovalent saturated hydrocarbon group of 1 to 10 carbon atoms, provided that part or all of the hydrogen atoms of the saturated hydrocarbon group may be substituted; $Ra'^{14}$ represents an aromatic hydrocarbon group which may have a substituent; and * represents a valence bond (the same definition hereafter).

In the formula (a1-r2-1), as the alkyl group of 1 to 10 carbon atoms for $Ra'^{10}$, the same groups as described above for the linear or branched alkyl group for $Ra'^3$ in the formula (a1-r-1) are preferable.

$Ra'^{10}$ is preferably an alkyl group of 1 to 5 carbon atoms.

In formula (a1-r2-1), the aliphatic cyclic group which is formed by $Ra'^{11}$ together with the carbon atom bonded to Ra'$^{10}$, the same groups as those described above for the monocyclic or polycyclic aliphatic hydrocarbon group for Ra'$^{3}$ in formula (a1-r-1) are preferable.

In formula (a1-r2-2), as the cyclic hydrocarbon group formed by Xa together with Ya, a group in which 1 or more hydrogen atoms have been removed from the monovalent cyclic hydrocarbon group (aliphatic hydrocarbon group or aromatic hydrocarbon group) for Ra'$^{3}$ in the aforementioned formula (a1-r-1) may be mentioned.

The cyclic hydrocarbon group which Xa forms with Ya may have a substituent. Examples of substituents include the same substituents as those which the cyclic hydrocarbon group for Ra'$^{3}$ may have.

In formula (a1-r2-2), examples of the monovalent saturated chain hydrocarbon group of 1 to 10 carbon atoms for Ra$^{01}$ to Ra$^{03}$ include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms for Ra$^{01}$ to Ra$^{03}$ include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, and a cyclododecyl group; and a polycyclic aliphatic saturated hydrocarbon group such as a bicyclo[2.2.2]octanyl group, a tricyclo[5.2.1.0$^{2,6}$]decanyl group, a tricyclo[3.3.1.1$^{3,7}$]decanyl group, a tetracyclo[6.2.1.1$^{3,6}$.0$^{2,7}$]dodecanyl group, and an adamantyl group.

Among these examples, as Ra$^{01}$ to Ra$^{03}$, in terms of ease in synthesis of the monomeric compound which derives the structural unit (a1), a hydrogen atom or a saturated chain hydrocarbon group having 1 to 10 carbon atoms is preferable, a hydrogen atom, a methyl group or an ethyl group is more preferable, and a hydrogen atom is most preferable.

As the substituent for the saturated chain hydrocarbon group or saturated cyclic aliphatic hydrocarbon group represented by Ra$^{01}$ to Ra$^{03}$, for example, the same substituents as those described above for Ra$^{05}$ may be mentioned.

Examples of the group containing a carbon-carbon double bond which is generated by forming a cyclic structure in which two or more of Ra$^{01}$ to Ra$^{03}$ are bonded to each other include a cyclopentenyl group, a cyclohexenyl group, a methyl cyclopentenyl group, a methyl cyclohexenyl group, a cyclopentylideneethenyl group, and a cyclohexylideneethenyl group. Among these examples, from the viewpoint of the ease of synthesis of the monomer compound which derives the structural unit (a1), a cyclopentenyl group, a cyclohexenyl group, and a cyclopentylidenethenyl group are preferable.

In formula (a1-r2-3), an aliphatic cyclic group which is formed of Xaa together with Yaa is preferably a group exemplified as an aliphatic hydrocarbon group which is a monocyclic group or a polycyclic group of Ra'$^{3}$ in general formula (a1-r-1).

In general formula (a1-r2-3), examples of the aromatic hydrocarbon group for Ra$^{04}$ include a group obtained by removing one or more hydrogen atoms from an aromatic hydrocarbon ring having 5 to 30 carbon atoms. Among these examples, Ra$^{04}$ is preferably a group obtained by removing one or more hydrogen atoms from an aromatic hydrocarbon ring having 6 to 15 carbon atoms, a group obtained by removing one or more hydrogen atoms from benzene, naphthalene, anthracene, or phenanthrene is further preferable, a group obtained by removing one or more hydrogen atoms from benzene, naphthalene, or anthracene is still further preferable, a group obtained by removing one or more hydrogen atoms from benzene and naphthalene is particularly preferable, and a group obtained by removing one or more hydrogen atoms from benzene is most preferable.

Examples of the substituent that Ra$^{04}$ in general formula (a1-r2-3) may have include a methyl group, an ethyl group, a propyl group, a hydroxyl group, a carboxyl group, a halogen atom (a fluorine atom, a chlorine atom, a bromine atom, or the like), an alkoxy group (a methoxy group, an ethoxy group, a propoxy group, a butoxy group, or the like), and an alkyloxycarbonyl group.

In general formula (a1-r2-4), Ra'$^{12}$ and Ra'$^{13}$ each independently represent a monovalent chain saturated hydrocarbon group having 1 to 10 carbon atoms or a hydrogen atom. With respect to Ra'$^{12}$ and Ra'$^{13}$, examples of the monovalent chain saturated hydrocarbon group having 1 to 10 carbon atoms include the same monovalent chain saturated hydrocarbon group having 1 to 10 carbon atoms as that for Ra$^{01}$ to Ra$^{03}$, provided that part or all of the hydrogen atoms of the saturated hydrocarbon group may be substituted;

Among these examples, as Ra'$^{12}$ and Ra'$^{13}$, a hydrogen atom and an alkyl group having 1 to 5 carbon atoms are preferable, an alkyl group having 1 to 5 carbon atoms is further preferable, a methyl group and an ethyl group are still further preferable, and a methyl group is particularly preferable.

In the case where the chain saturated hydrocarbon group represented by Ra'$^{12}$ and Ra'$^{13}$ is substituted, examples of the substituent include the same group as that of Ra$^{05}$.

In general formula (a1-r2-4), Ra'$^{14}$ is an aromatic hydrocarbon group which may have a substituent. Examples of the hydrocarbon group for Ra'$^{14}$ include the same aromatic hydrocarbon groups as those exemplified in the description for Ra$^{04}$. Among these examples, Ra'$^{14}$ is preferably a group obtained by removing one or more hydrogen atoms from the aromatic hydrocarbon group having 6 to 15 carbon atoms, is further preferably a group obtained by removing one or more hydrogen atoms from benzene, naphthalene, anthracene, or phenanthrene, is still further preferably a group obtained by removing one or more hydrogen atoms from benzene, naphthalene, or anthracene, is particularly preferably a group obtained by removing one or more hydrogen atoms from naphthalene or anthracene, and is most preferably a group obtained by removing one or more hydrogen atoms from naphthalene.

Examples of the substituent that Ra'$^{14}$ may have include the same group as the substituent that Ra$^{04}$ may have.

In the case where Ra'$^{14}$ in general formula (a1-r2-4) is a naphthyl group, a position which is bonded to a tertiary carbon atom in general formula (a1-r2-4) may be 1-position and 2-position of the naphthyl group.

In the case where Ra'$^{14}$ in general formula (a1-r2-4) is an anthryl group, a position which is bonded to a tertiary carbon atom in general formula (a1-r2-4) may be any one of 1-position, 2-position, and 9-position of the anthryl group.

Specific examples of the group represented by the aforementioned formula (a1-r2-1) are shown below.

[Chemical Formula 7]

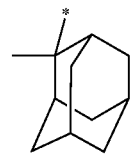

(r-pr-m1)

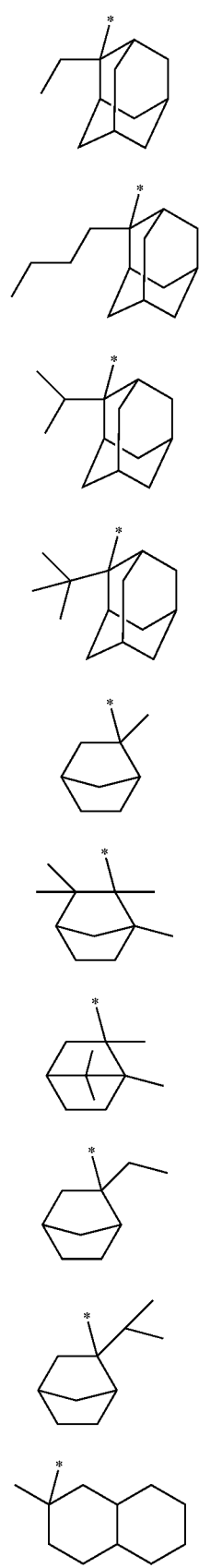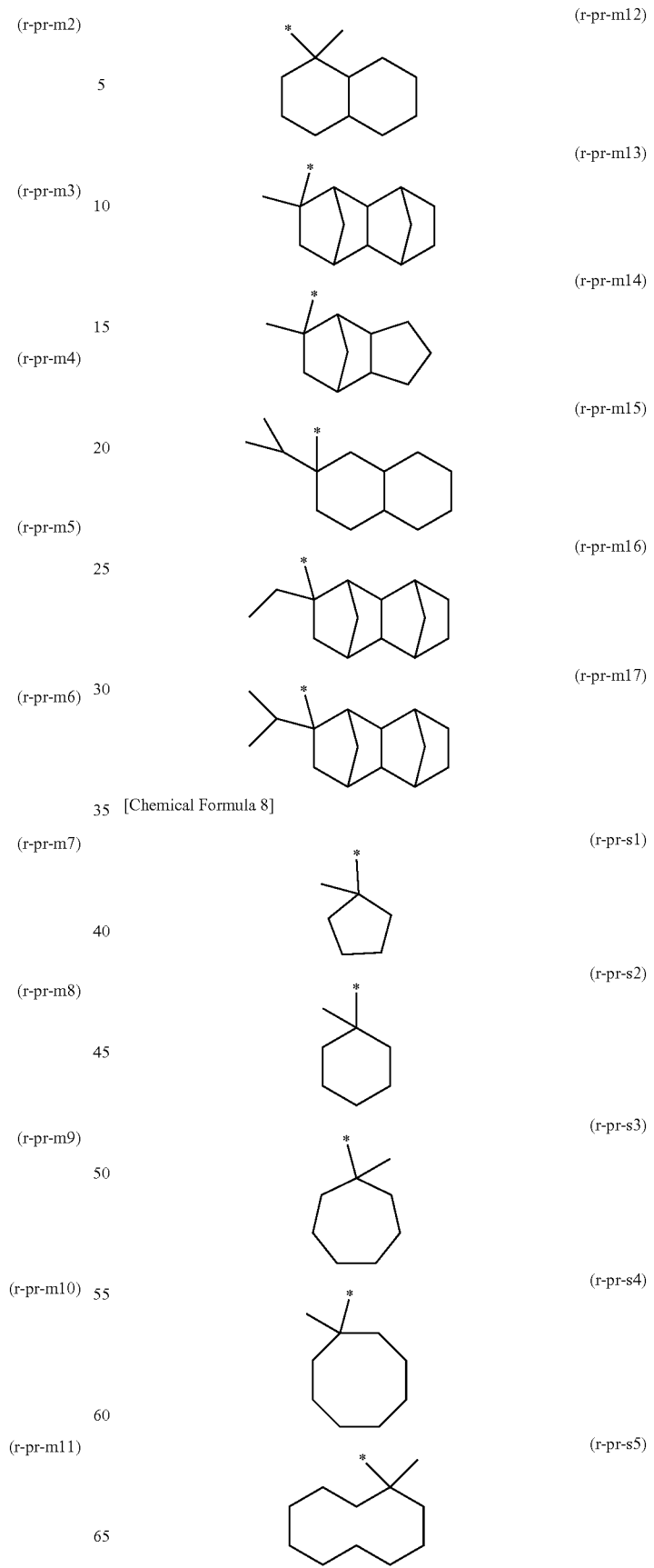

-continued
(r-pr-s6) 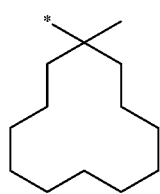
(r-pr-s7) 
(r-pr-s8) 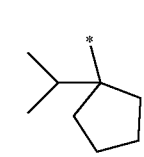
(r-pr-s9) 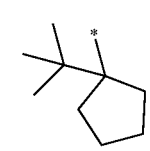
(r-pr-s10) 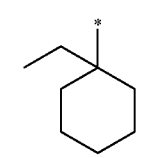
(r-pr-s11) 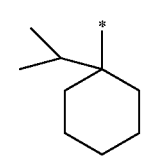
(r-pr-s12) 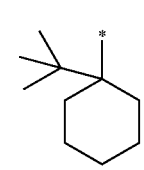
(r-pr-s13) 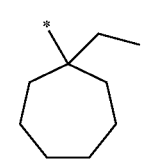
(r-pr-s14) 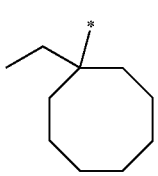
(r-pr-s15) 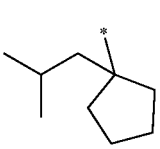
-continued
(r-pr-s16) 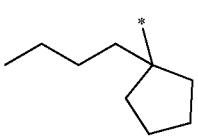
(r-pr-s17) 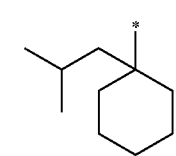
(r-pr-s18) 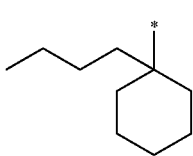
Specific examples of the group represented by the aforementioned formula (a1-r2-2) are shown below.
[Chemical Formula 9]
(r-pr-sv1)
(r-pr-sv2)
(r-pr-sv3)
(r-pr-sv4)
(r-pr-sv5)
(r-pr-sv6)

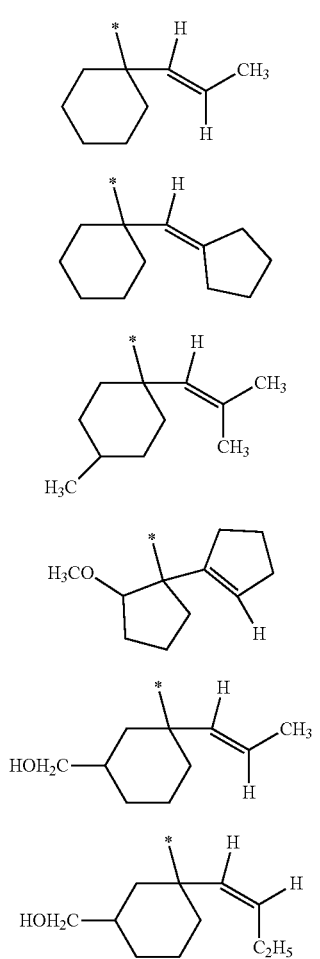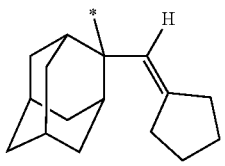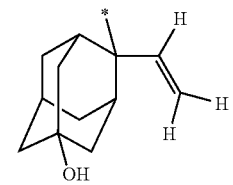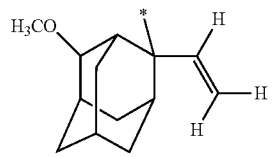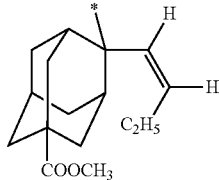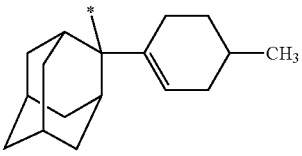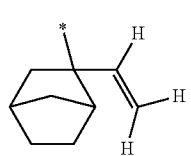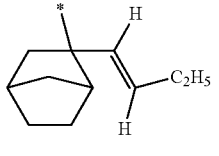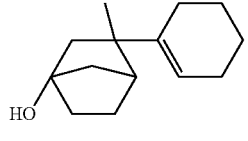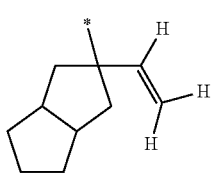

-continued
(r-pr-mv14)
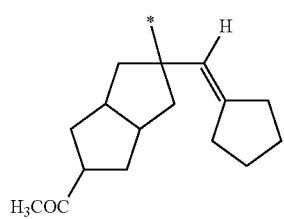
(r-pr-mv15)
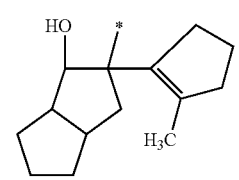
(r-pr-mv16)
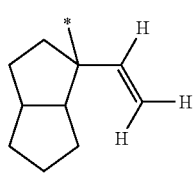
(r-pr-mv17)
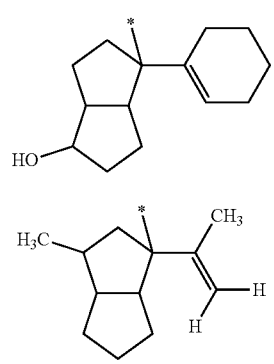
(r-pr-mv18)
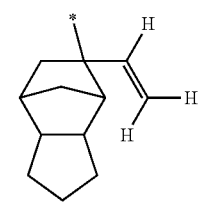
(r-pr-mv19)
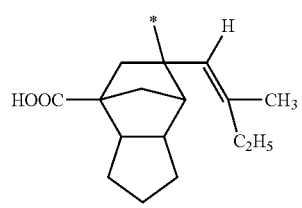
(r-pr-mv20)
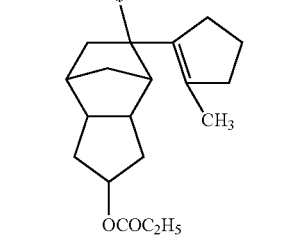
(r-pr-mv21)
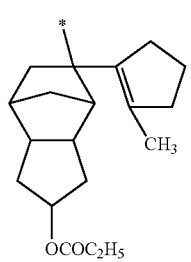
-continued
[Chemical Formula 12]
(r-pr-av1)
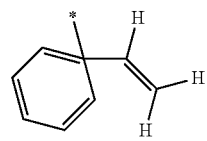
(r-pr-av2)
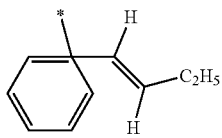
(r-pr-av3)
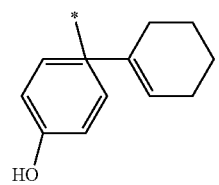
(r-pr-av4)
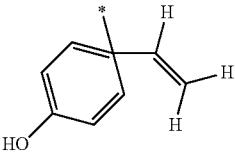
(r-pr-av5)
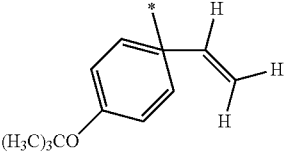
Specific examples of the group represented by the aforementioned formula (a1-r2-3) are shown below.
[Chemical Formula 13]
(r-pr-sa1)
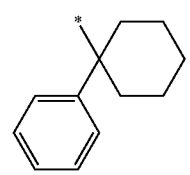
(r-pr-sa2)
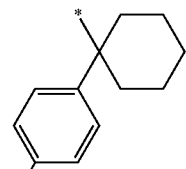
(r-pr-sa3)
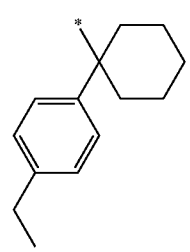

-continued

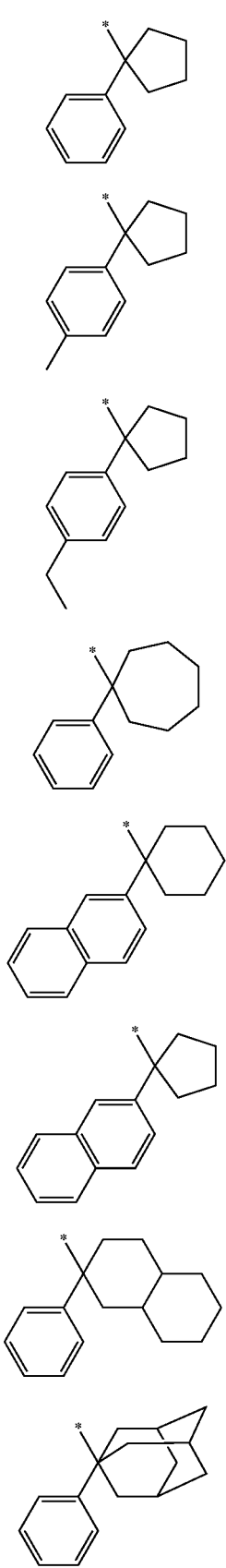

(r-pr-sa4)
(r-pr-sa5)
(r-pr-sa6)
(r-pr-sa7)
(r-pr-sa8)
(r-pr-sa9)
(r-pr-ma1)
(r-pr-ma2)

Specific examples of the group represented by the aforementioned formula (a1-r2-4) are shown below.

[Chemical Formula 14]

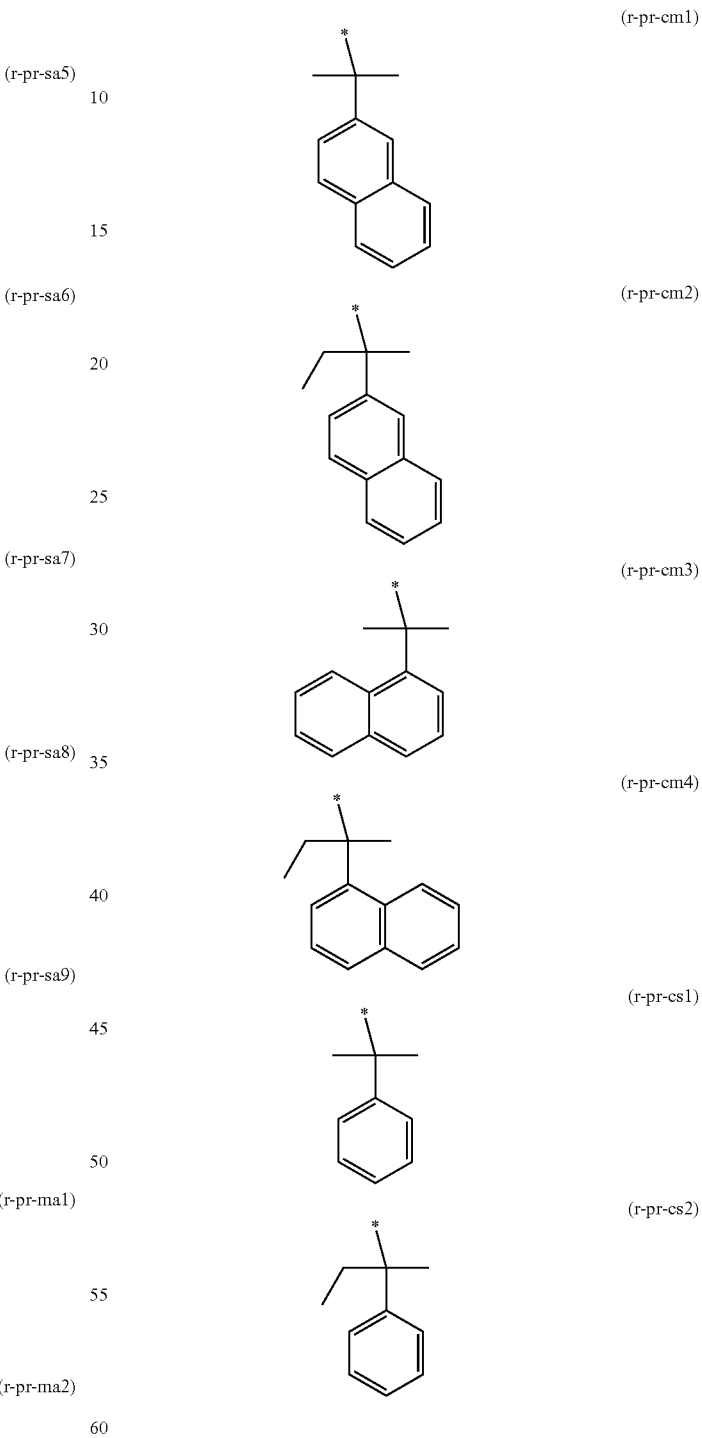

(r-pr-cm1)
(r-pr-cm2)
(r-pr-cm3)
(r-pr-cm4)
(r-pr-cs1)
(r-pr-cs2)

Tertiary Alkyloxycarbonyl Acid Dissociable Group

Examples of the acid dissociable group for protecting a hydroxy group as a polar group include the acid dissociable group represented by general formula (a1-r-3) shown below (hereafter, for convenience, referred to as "tertiary alkyloxycarbonyl-type acid dissociable group").

[Chemical Formula 15]

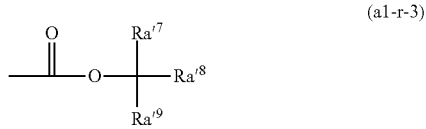

(a1-r-3)

In the formula, $Ra'^7$ to $Ra'^9$ each independently represents an alkyl group.

In the formula (a1-r-3), $Ra'^7$ to $Ra'^9$ is preferably an alkyl group of 1 to 5 carbon atoms, and more preferably an alkyl group of 1 to 3 carbon atoms.

Further, the total number of carbon atoms within the alkyl group is preferably 3 to 7, more preferably 3 to 5, and most preferably 3 or 4.

Examples of the structural unit (a1) include a structural unit derived from an acrylate ester which may have the hydrogen atom bonded to the carbon atom on the α-position substituted with a substituent; a structural unit derived from an acrylamide; a structural unit derived from hydroxystyrene or a hydroxystyrene derivative in which at least a part of the hydrogen atom of the hydroxy group is protected with a substituent containing an acid decomposable group; and a structural unit derived from vinylbenzoic acid or a vinylbenzoic acid derivative in which at least a part of the hydrogen atom within —C(=O)—OH is protected with a substituent containing an acid decomposable group.

As the structural unit (a1), a structural unit derived from an acrylate ester which may have the hydrogen atom bonded to the carbon atom on the α-position substituted with a substituent is preferable.

Specific examples of preferable structural units for the structural unit (a1) include structural units represented by general formula (a1-1) or (a1-2) shown below.

[Chemical Formula 16]

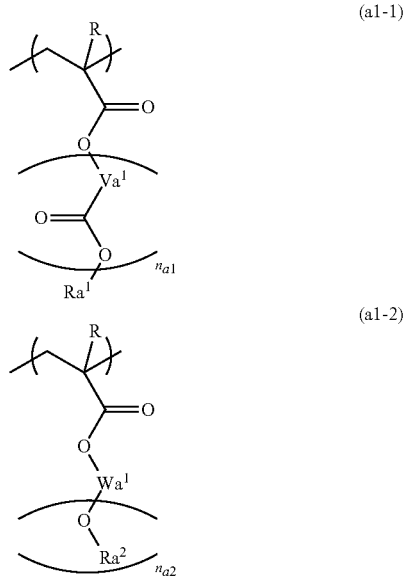

(a1-1)

(a1-2)

In the formula, R represents a hydrogen atom, an alkyl group of 1 to 5 carbon atoms or a halogenated alkyl group of 1 to 5 carbon atoms; $Va^1$ represents a divalent hydrocarbon group optionally having an ether bond; $n_{a1}$ represents an integer of 0 to 2; $Ra^1$ represents an acid dissociable group represented by the aforementioned formula (a1-r-1) or (a1-r-2); $Wa^1$ represents a hydrocarbon group having a valency of $n_{a2}+1$; $n_{a2}$ represents an integer of 1 to 3; and $Ra^2$ represents an acid dissociable group represented by the aforementioned formula (a1-r-1) or (a1-r-3).

In the aforementioned formula (a1-1), as the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms represented by R is a group in which part or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In formula (a1-1), the divalent hydrocarbon group for $V^1$ may be either an aliphatic hydrocarbon group or an aromatic hydrocarbon group.

The aliphatic hydrocarbon group as the divalent hydrocarbon group for $Va^1$ may be either saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—($CH_2$)$_2$—], a trimethylene group [—($CH_2$)$_3$—], a tetramethylene group [—($CH_2$)$_4$—] and a pentamethylene group [—($CH_2$)$_5$—].

The branched aliphatic hydrocarbon group preferably has 3 to 10 carbon atoms, more preferably 3 to 6 carbon atoms, still more preferably 3 or 4 carbon atoms, and most preferably 3 carbon atoms.

As the branched aliphatic hydrocarbon group, branched alkylene groups are preferred, and specific examples include various alkylalkylene groups, including alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)—, and —C($CH_2CH_3$)$_2$—; alkylethylene groups such as —CH($CH_3$)$CH_2$—, —CH($CH_3$)CH($CH_3$)—, —C($CH_3$)$_2CH_2$—, —CH($CH_2CH_3$)$CH_2$—, and —C($CH_2CH_3$)$_2$—$CH_2$—; alkyltrimethylene groups such as —CH($CH_3$)$CH_2CH_2$—, and —$CH_2$CH($CH_3$)$CH_2$—; and alkyltetramethylene groups such as —CH($CH_3$)$CH_2CH_2CH_2$—, and —$CH_2$CH($CH_3$)$CH_2CH_2$—. As the alkyl group within the alkylalkylene group, a linear alkyl group of 1 to 5 carbon atoms is preferable.

As examples of the hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given. The linear or branched aliphatic hydrocarbon group is the same as defined for the aforementioned linear aliphatic hydrocarbon group or the aforementioned branched aliphatic hydrocarbon group.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aromatic hydrocarbon group as the divalent hydrocarbon group for $Va^1$ is a hydrocarbon group having an aromatic ring.

The aromatic hydrocarbon group preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atom, more preferably 1 or 2, and most preferably 1.

In formula (a1-1), Ra' represents an acid dissociable group represented by the aforementioned formula (a1-r-1) or (a1-r-2).

In the aforementioned formula (a1-2), the hydrocarbon group for $Wa^1$ having a valency of $n_{a2}+1$ may be either an aliphatic hydrocarbon group or an aromatic hydrocarbon group. The aliphatic cyclic group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof.

The valency of $n_{a2}+1$ is preferably divalent, trivalent or tetravalent, and divalent or trivalent is more preferable.

Specific examples of structural unit represented by formula (a1-1) are shown below. In the formulae shown below, $R^\alpha$ represents a hydrogen atom, a methyl group or a trifluoromethyl group.

[Chemical Formula 17]

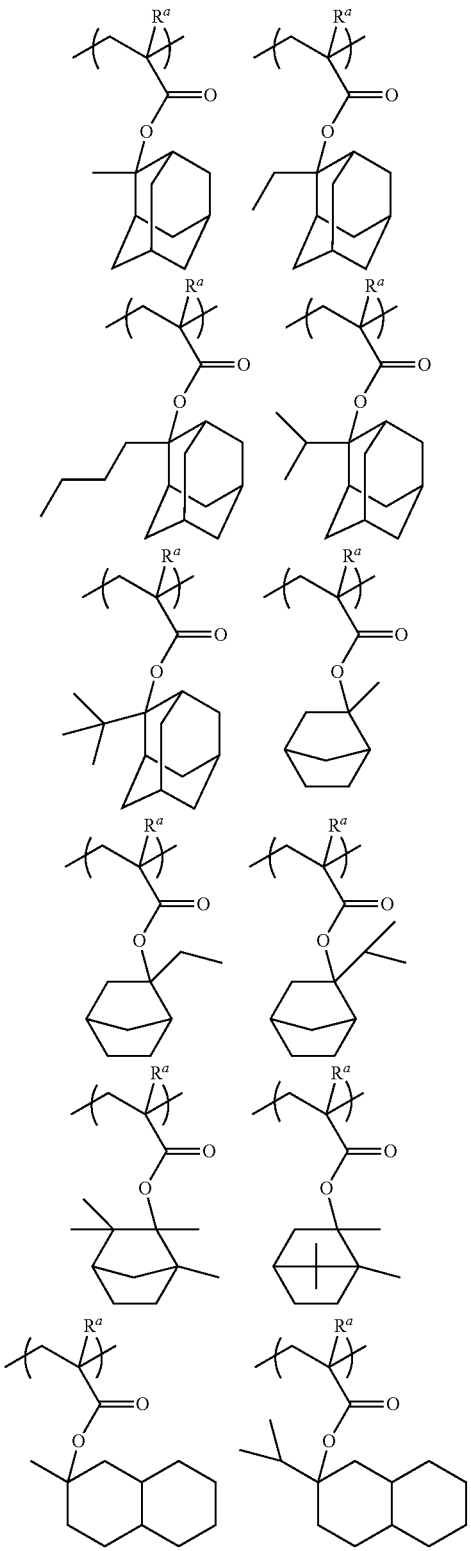

-continued
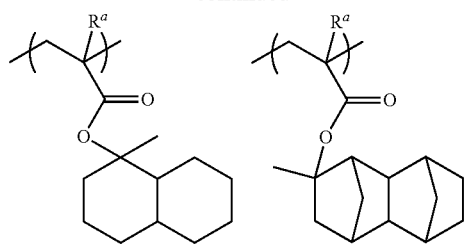
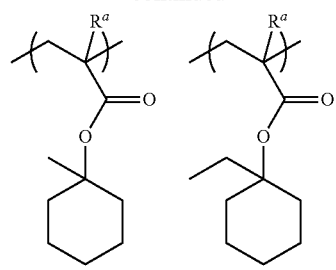
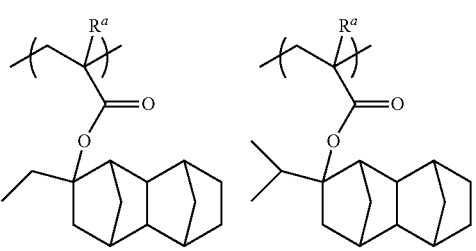
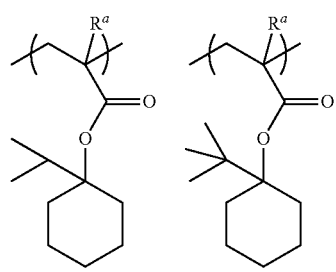
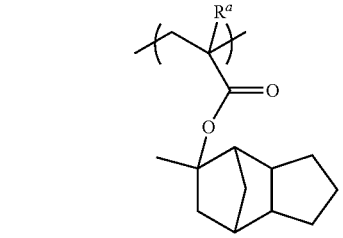
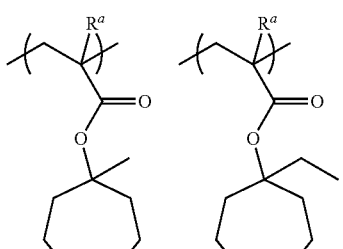
[Chemical Formula 18]
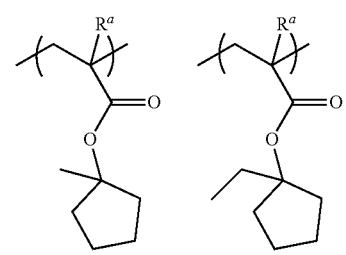
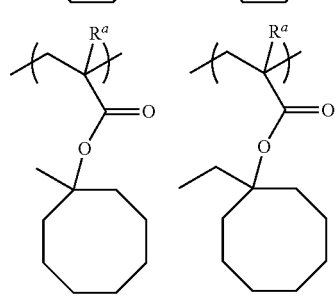
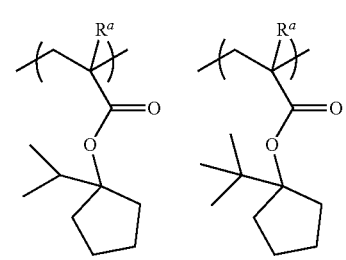
[Chemical Formula 19]
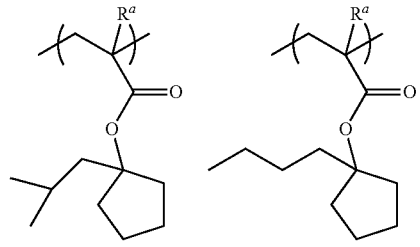
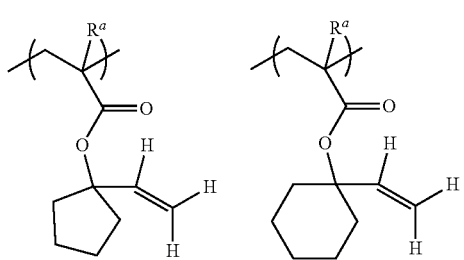
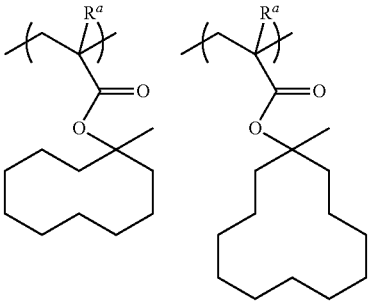

-continued
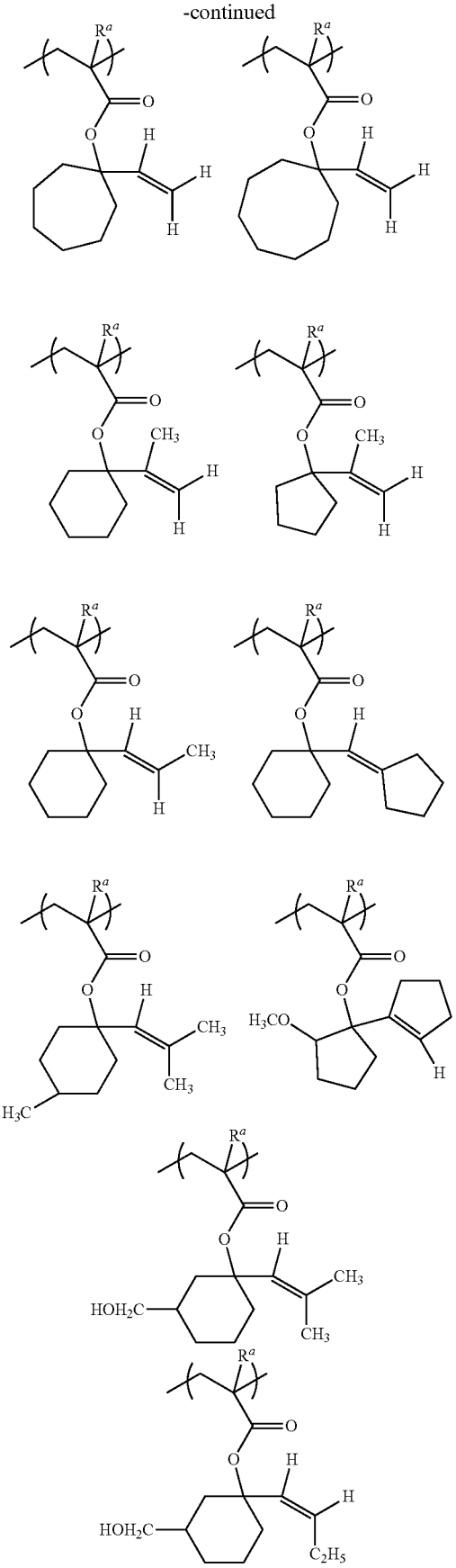
-continued
[Chemical Formula 20]
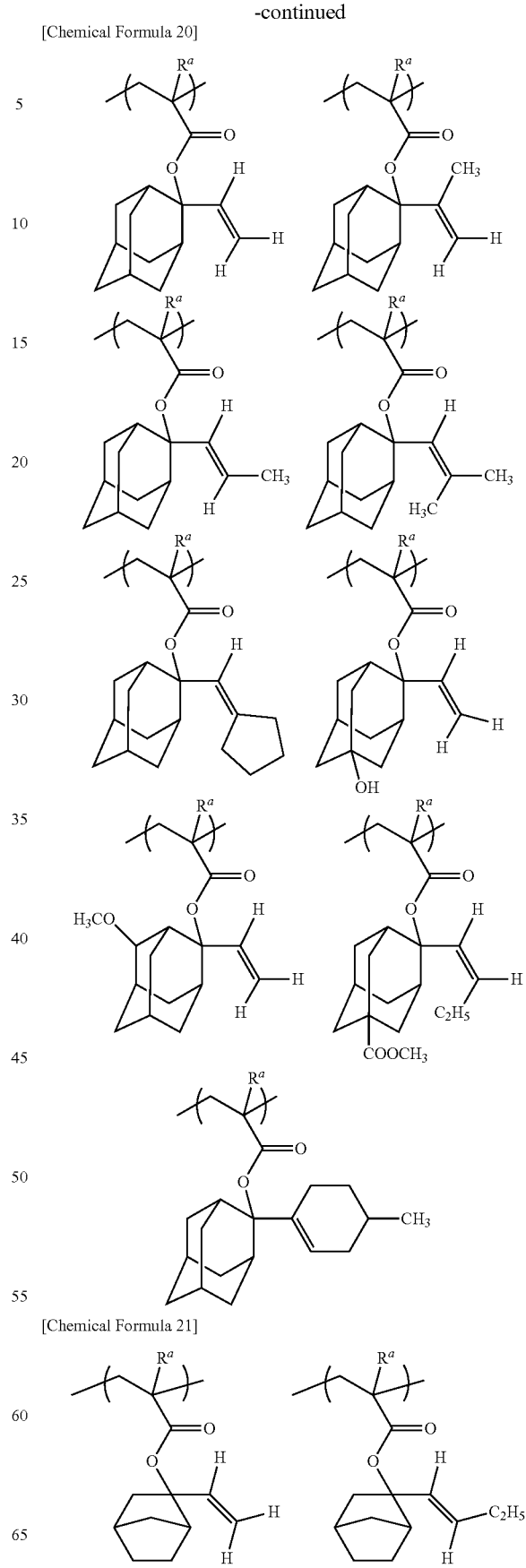
[Chemical Formula 21]

-continued
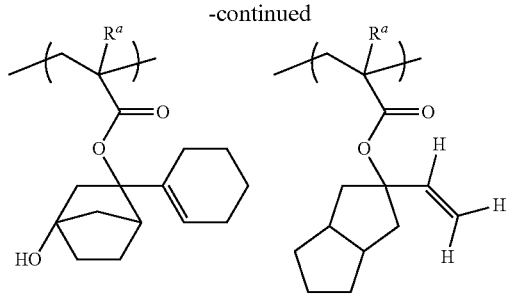
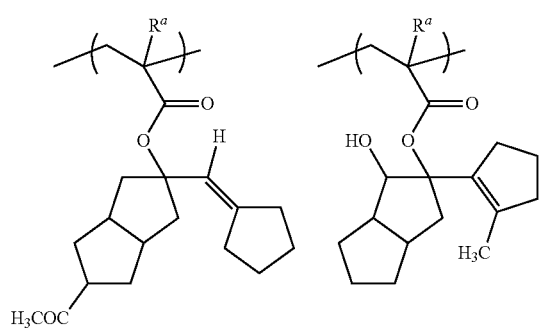
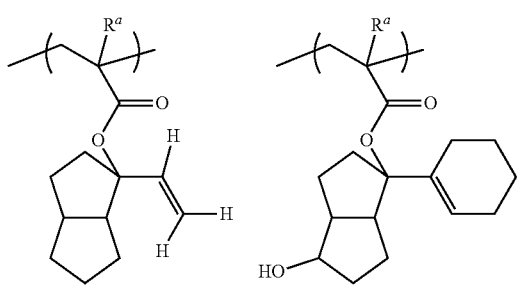
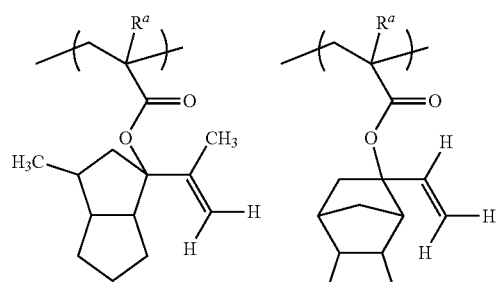
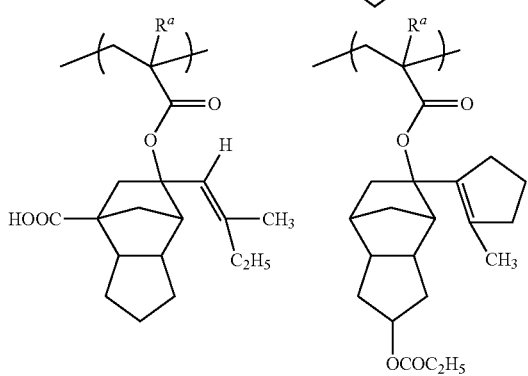
-continued
[Chemical Formula 22]
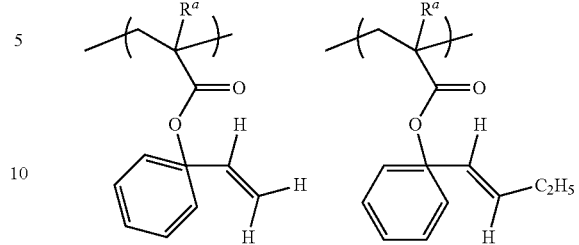
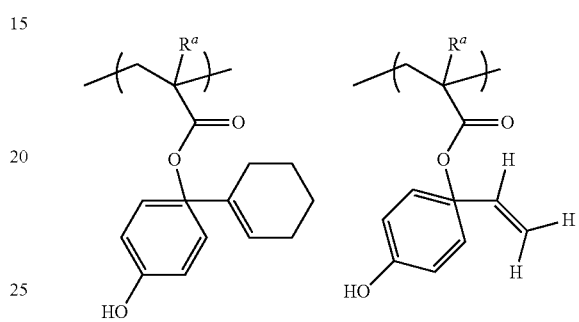
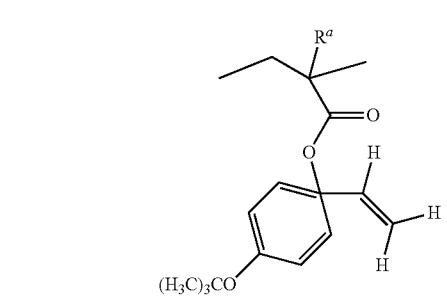
[Chemical Formula 23]
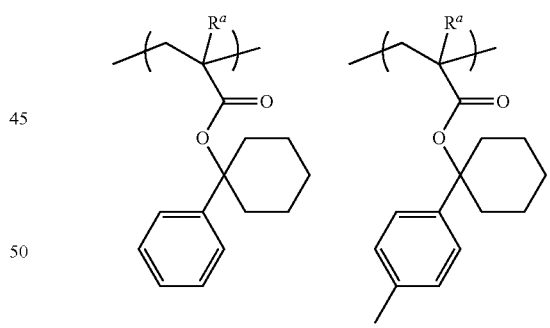
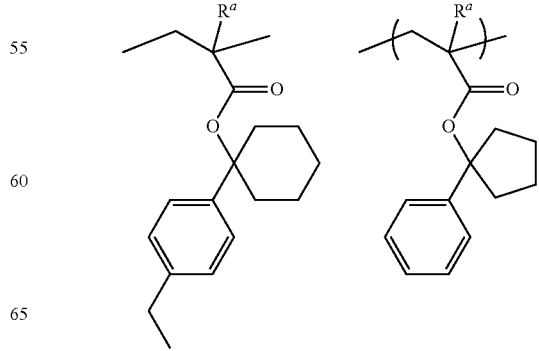

-continued
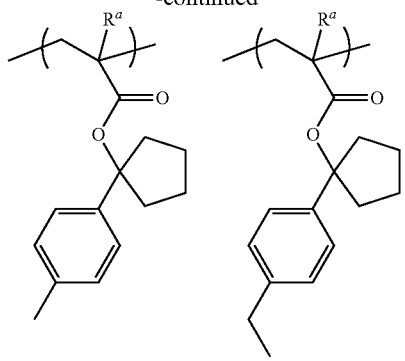
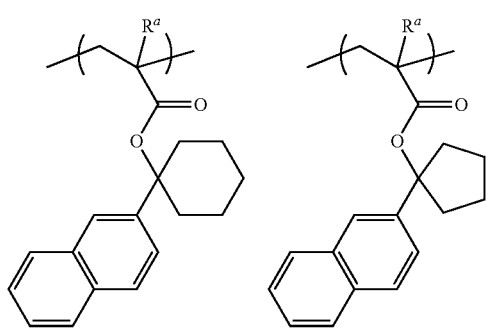
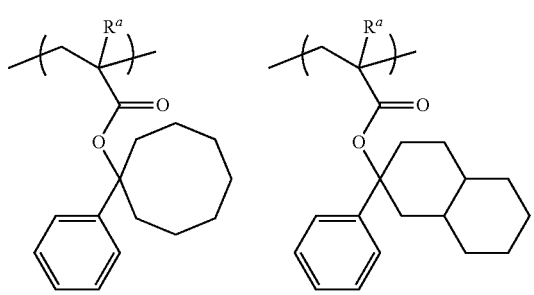
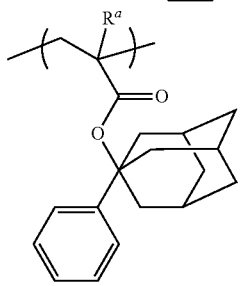
[Chemical Formula 24]
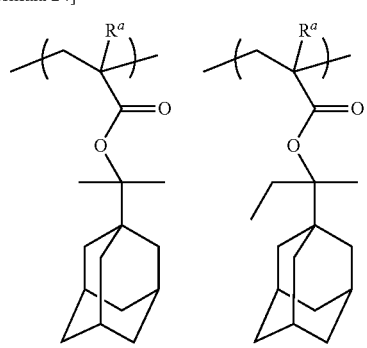
-continued
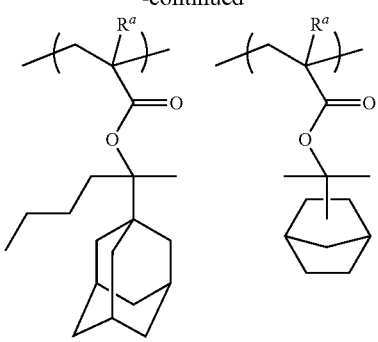
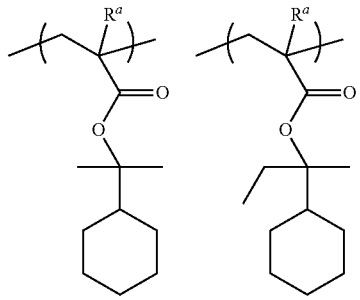
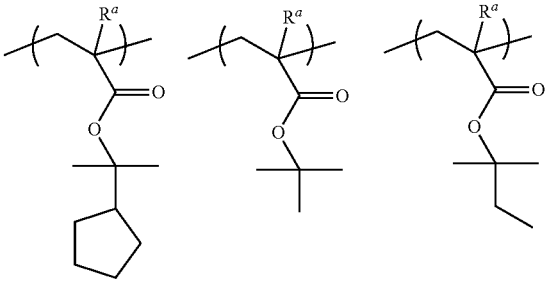
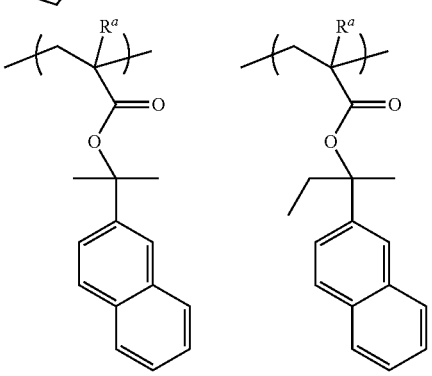
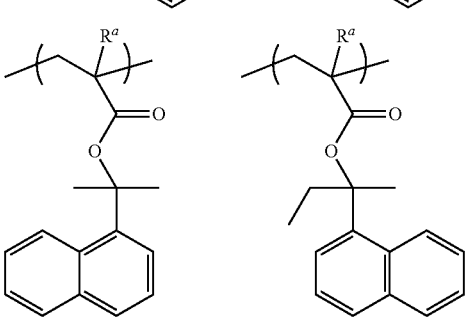

[Chemical Formula 25]
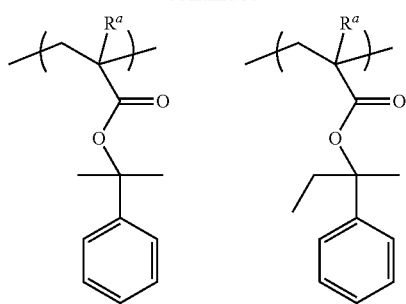
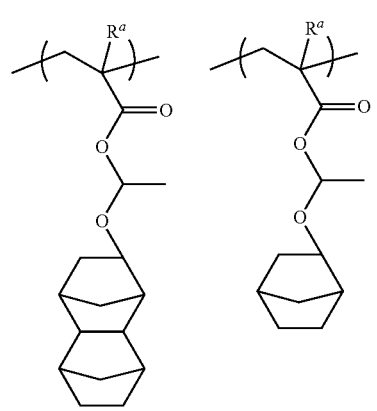
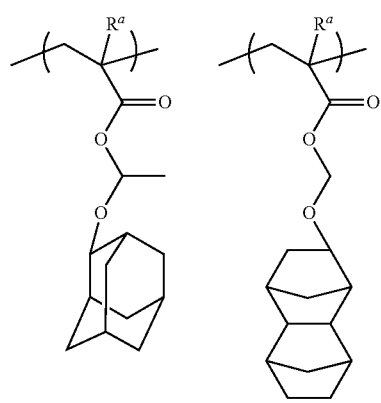
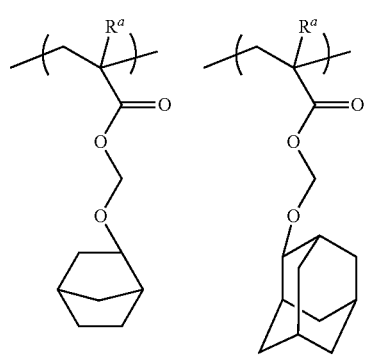
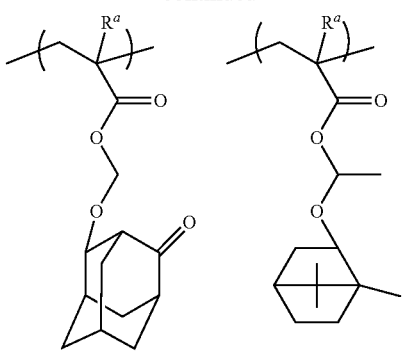
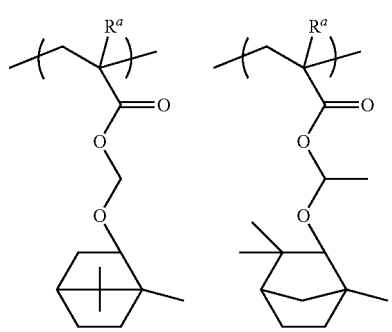
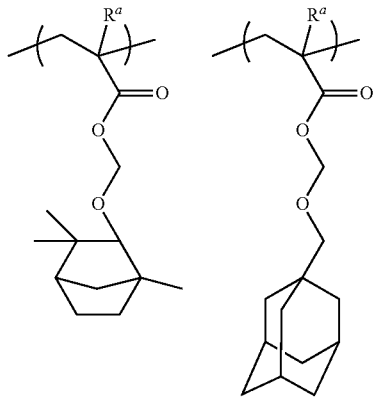
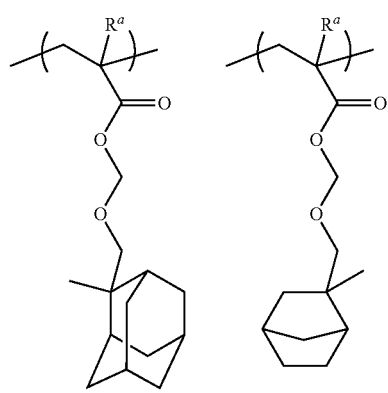

[Chemical Formula 26]
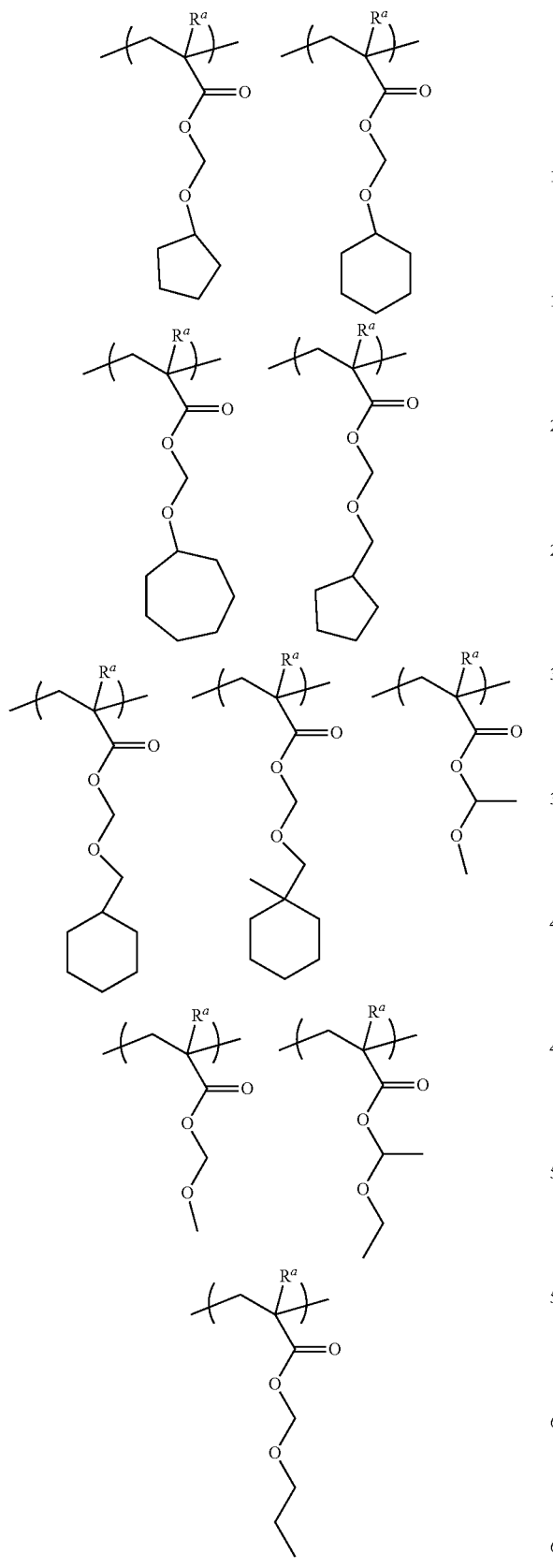
[Chemical Formula 27]
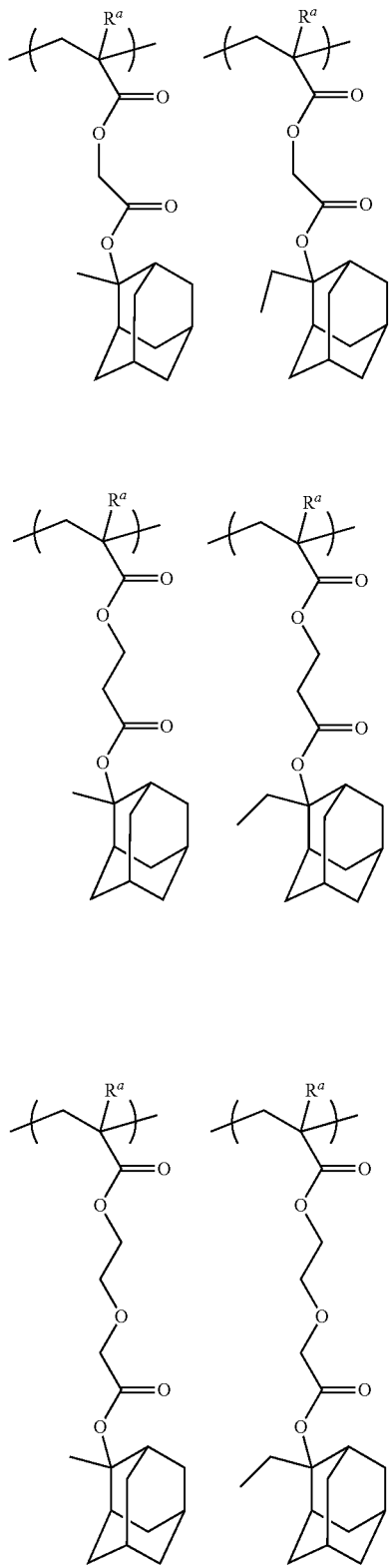

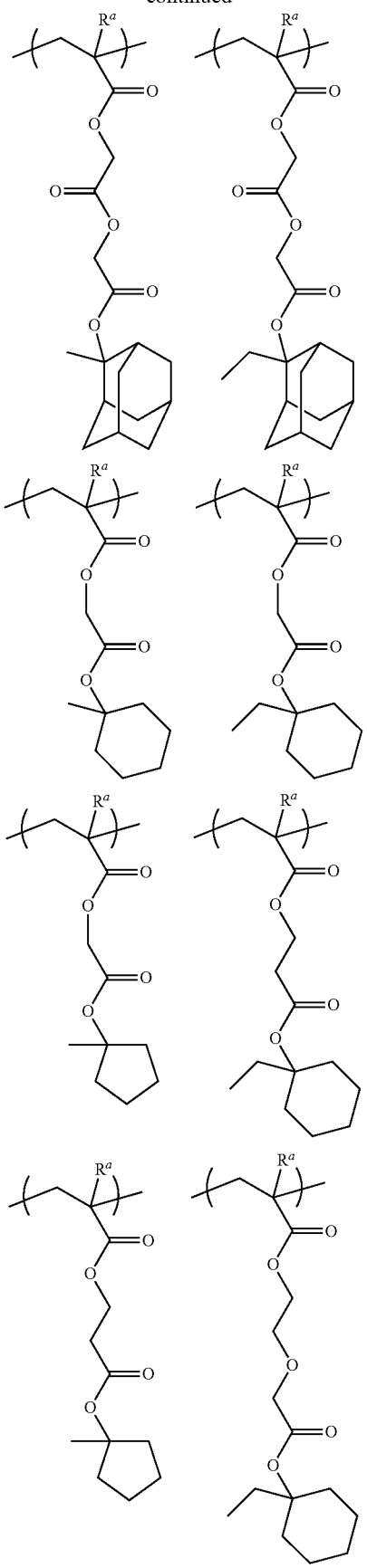
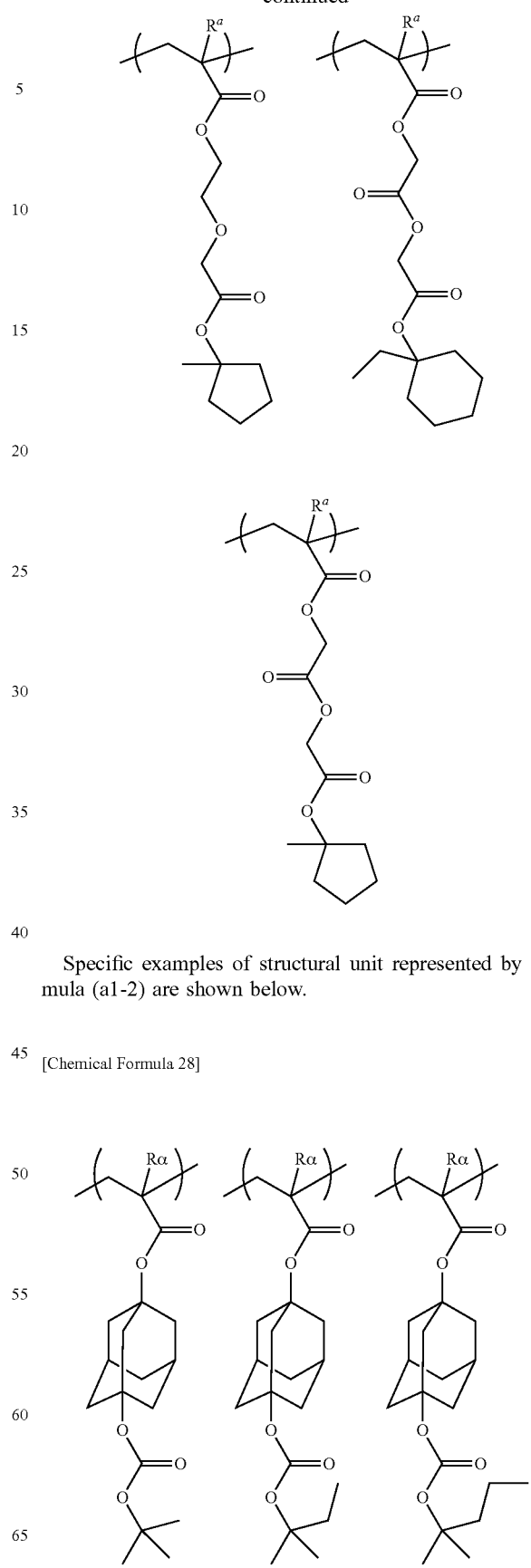
Specific examples of structural unit represented by formula (a1-2) are shown below.
[Chemical Formula 28]

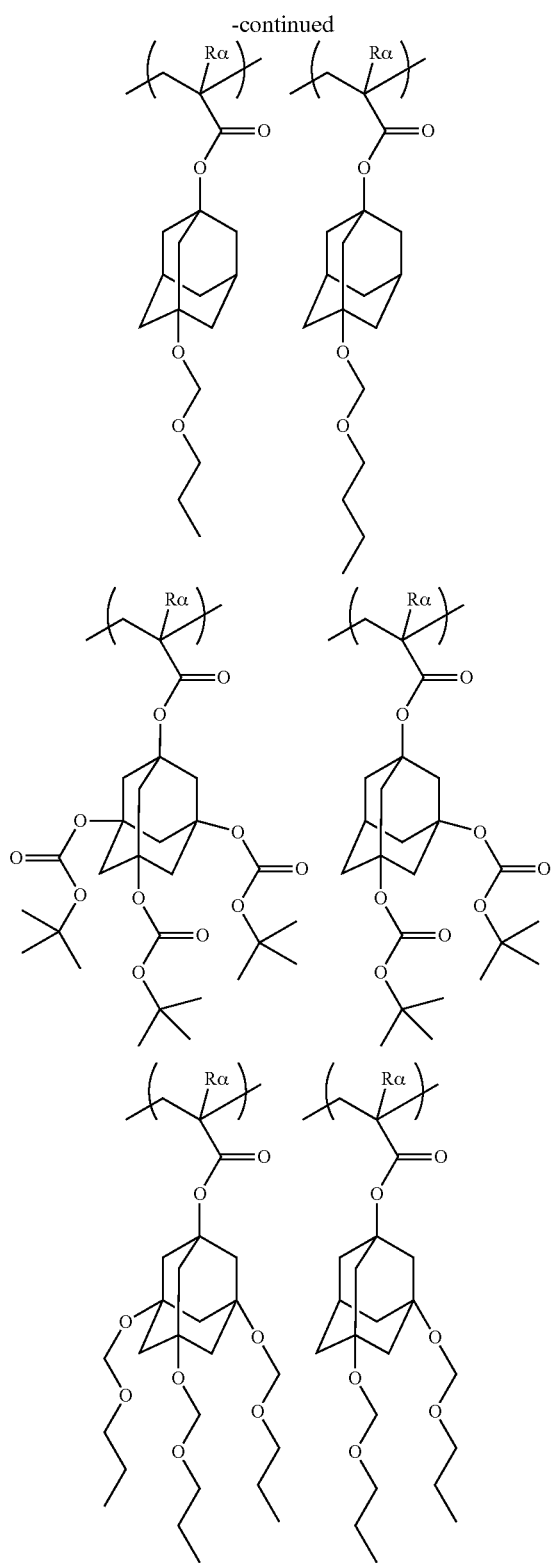

ably 10 to 80 mol %, more preferably 20 to 70 mol %, and still more preferably 25 to 60 mol %.

When the amount of the structural unit (a1) is at least as large as the lower limit of the above-mentioned range, a resist pattern can be reliably obtained, and various lithography properties such as resolution and roughness are further improved. On the other hand, when the amount of the structural unit (a1) is no more than the upper limit of the above-mentioned range, a good balance can be achieved with the other structural units.

(Structural Unit (a2))

The component (A1) may further include a structural unit (a2) which contains a lactone-containing cyclic group, an —$SO_2$— containing cyclic group or a carbonate-containing cyclic group (provided that structural units which fall under the definition of the structural unit (a1) are excluded).

When the component (A1) is used for forming a resist film, the lactone-containing cyclic group, the —$SO_2$— containing cyclic group or the carbonate-containing cyclic group within the structural unit (a2) is effective in improving the adhesion between the resist film and the substrate. Further, by virtue of including the structural unit (a2), in an alkali developing process, during developing, the solubility of the resist film in an alkali developing is enhanced.

The term "lactone-containing cyclic group" refers to a cyclic group including a ring containing a —O—C(=O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

The lactone-containing cyclic group for the structural unit (a2) is not particularly limited, and an arbitrary structural unit may be used. Specific examples include groups represented by general formulae (a2-r-1) to (a2-r-7) shown below.

[Chemical Formula 29]

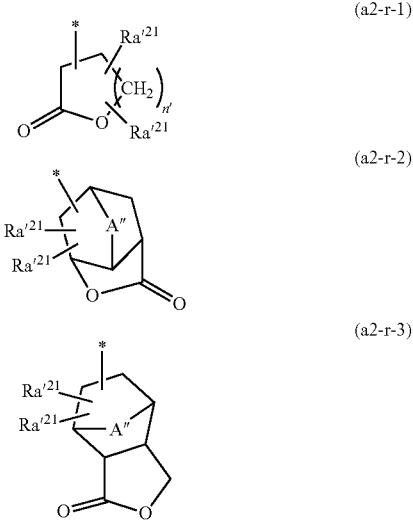

As the structural unit (a1) contained in the component (A1), 1 type of structural unit may be used, or 2 or more types may be used.

In the component (A1), the amount of the structural unit (a1) based on the combined total (100 mol %) of all structural units constituting the component (A1) is prefer-

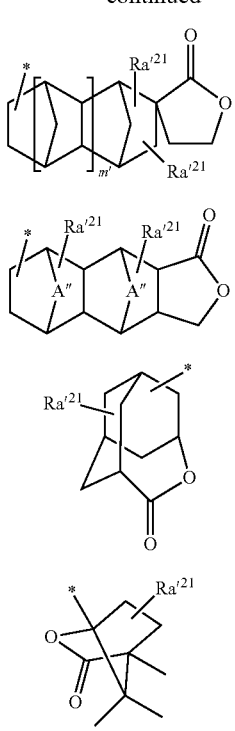

(a2-r-4)

(a2-r-5)

(a2-r-6)

(a2-r-7)

In the formulae, each $Ra'^{21}$ independently represents a hydrogen atom, an alkyl group, an alkoxy group, a halogen atom, a halogenated alkyl group, a hydroxy group, —COOR", —OC(═O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom (—O—), a sulfur atom (—S—) or an alkylene group of 1 to 5 carbon atoms which may contain an oxygen atom or a sulfur atom; n' represents an integer of 0 to 2; and m' represents 0 or 1.

In formulae (a2-r-1) to (a2-r-7), the alkyl group for $Ra'^{21}$ is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

The alkoxy group for $Ra'^{21}$ is preferably an alkoxy group of 1 to 6 carbon atoms.

Further, the alkoxy group is preferably a linear or branched alkoxy group. Specific examples of the alkoxy groups include the aforementioned alkyl groups for $Ra'^{21}$ having an oxygen atom (—O—) bonded thereto.

As examples of the halogen atom for $Ra'^{21}$, a fluorine atom, chlorine atom, bromine atom and iodine atom can be given. Among these, a fluorine atom is preferable.

Examples of the halogenated alkyl group for $Ra'^{21}$ include groups in which part or all of the hydrogen atoms within the aforementioned alkyl group for $Ra'^{21}$ has been substituted with the aforementioned halogen atoms. As the halogenated alkyl group, a fluorinated alkyl group is preferable, and a perfluoroalkyl group is particularly desirable.

With respect to —COOR" and —OC(═O)R" for $Ra'^{21}$, R" represents a hydrogen atom, an alkyl group, a lactone-containing cyclic group, a carbonate-containing cyclic group or an —SO$_2$— containing cyclic group.

The alkyl group for R" may be linear, branched or cyclic, and preferably has 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. Specific examples include groups in which one or more hydrogen atoms have been removed from a monocycloalkane or a polycycloalkane such as a bicycloalkane, tricycloalkane or tetracycloalkane which may or may not be substituted with a fluorine atom or a fluorinated alkyl group. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

Examples of the lactone-containing cyclic group for R" include groups represented by the aforementioned general formulae (a2-r-1) to (a2-r-7).

The carbonate-containing cyclic group for R" is the same as defined for the carbonate-containing cyclic group described later. Specific examples of the carbonate-containing cyclic group include groups represented by general formulae (ax3-r-1) to (ax3-r-3).

The —SO$_2$— containing cyclic group for R" is the same as defined for the —SO$_2$— containing cyclic group described later. Specific examples of the —SO$_2$— containing cyclic group include groups represented by general formulae (a5-r-1) to (a5-r-4).

The hydroxyalkyl group for $Ra'^{21}$ preferably has 1 to 6 carbon atoms, and specific examples thereof include the alkyl groups for $Ra'^{21}$ in which at least one hydrogen atom has been substituted with a hydroxy group.

In formulae (a2-r-2), (a2-r-3) and (a2-r-5), as the alkylene group of 1 to 5 carbon atoms represented by A", a linear or branched alkylene group is preferable, and examples thereof include a methylene group, an ethylene group, an n-propylene group and an isopropylene group. Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—CH$_2$—, —CH$_2$—O—CH$_2$—, —S—CH$_2$— and —CH$_2$—S—CH$_2$—. As A", an alkylene group of 1 to 5 carbon atoms or —O— is preferable, more preferably an alkylene group of 1 to 5 carbon atoms, and most preferably a methylene group.

Specific examples of the groups represented by the aforementioned general formulae (a2-r-1) to (a2-r-7) are shown below.

[Chemical Formula 30]

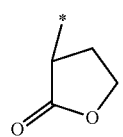

(r-lc-1-1)

-continued
(r-lc-1-2)
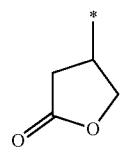
(r-lc-1-3)
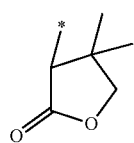
(r-lc-1-4)
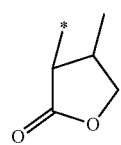
(r-lc-1-5)
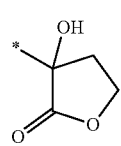
(r-lc-1-6)
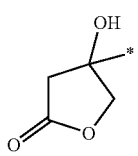
(r-lc-1-7)
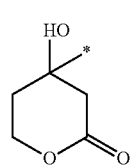
(r-lc-2-1)
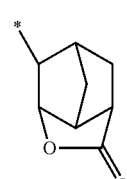
(r-lc-2-2)
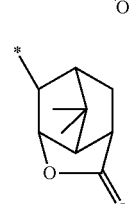
(r-lc-2-3)
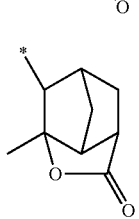
-continued
(r-lc-2-4)
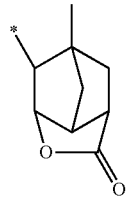
(r-lc-2-5)
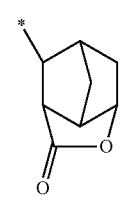
(r-lc-2-6)
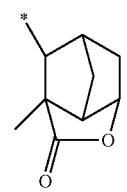
(r-lc-2-7)
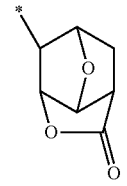
(r-lc-2-8)
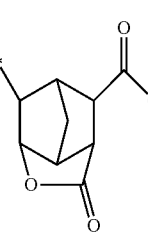
(r-lc-2-9)
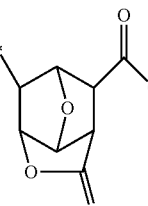
(r-lc-2-10)
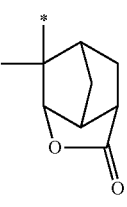

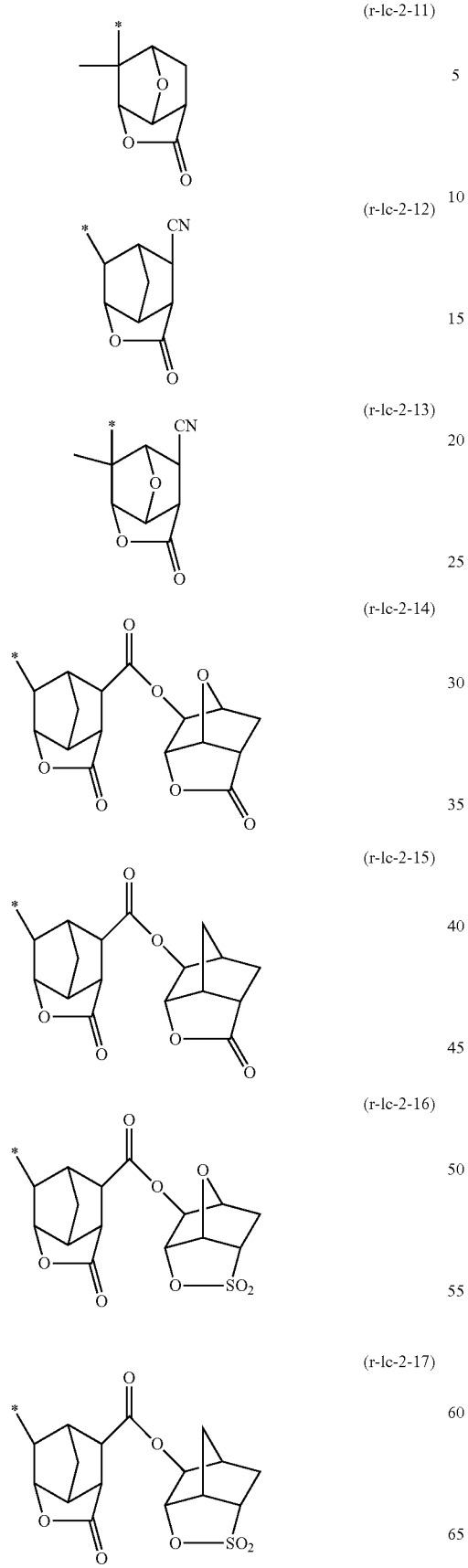
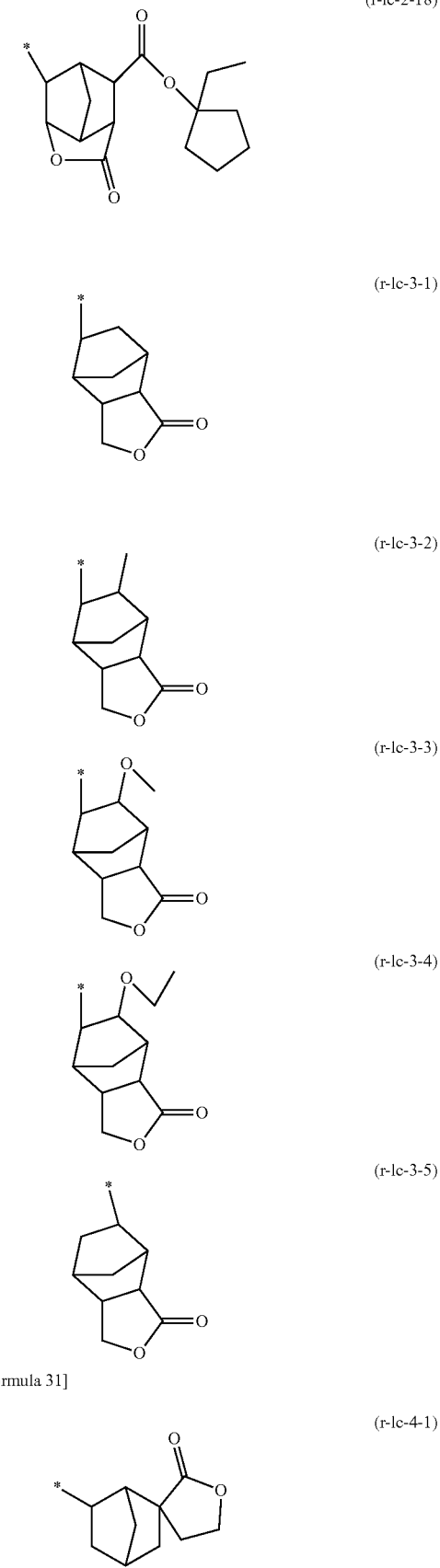
[Chemical Formula 31]

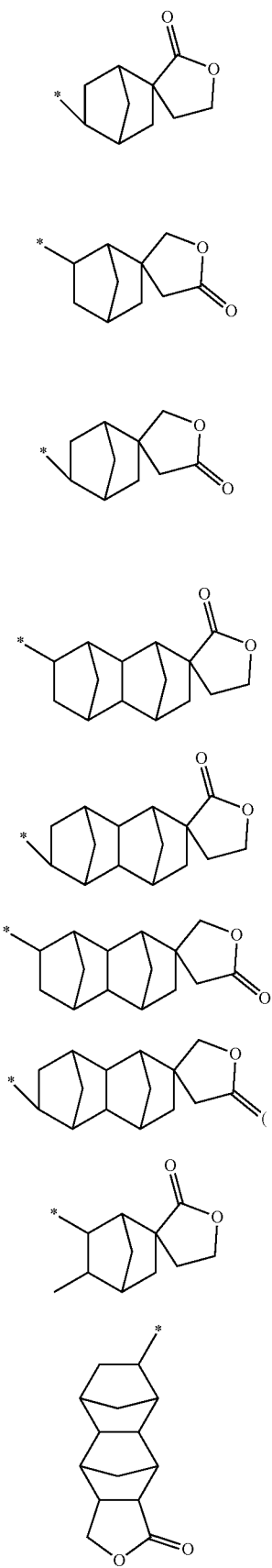

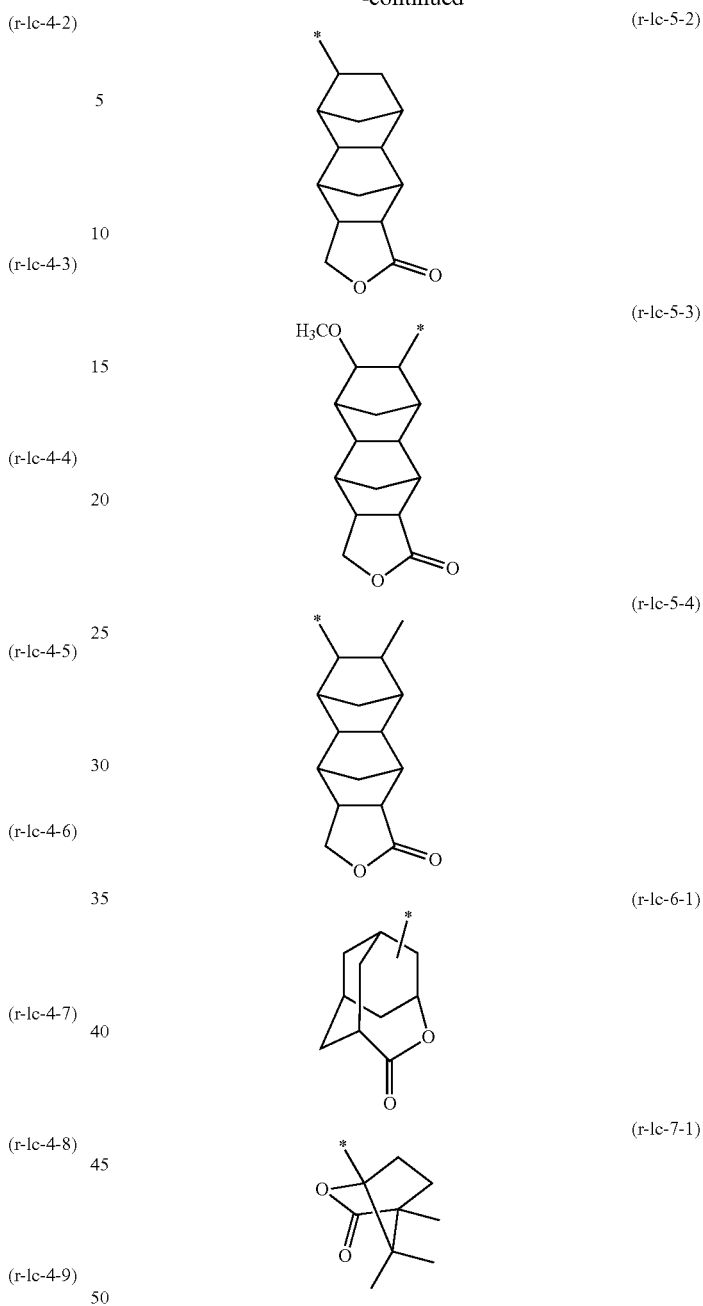

An "—SO₂— containing cyclic group" refers to a cyclic group having a ring containing —SO₂— within the ring structure thereof, i.e., a cyclic group in which the sulfur atom (S) within —SO₂— forms part of the ring skeleton of the cyclic group. The ring containing —SO₂— within the ring skeleton thereof is counted as the first ring. A cyclic group in which the only ring structure is the ring that contains —SO₂— in the ring skeleton thereof is referred to as a monocyclic group, and a group containing other ring structures is described as a polycyclic group regardless of the structure of the other rings. The —SO₂— containing cyclic group may be either a monocyclic group or a polycyclic group.

As the —SO₂— containing cyclic group, a cyclic group containing —O—SO₂— within the ring skeleton thereof, i.e., a cyclic group containing a sultone ring in which —O—S— within the —O—SO$_2$— group forms part of the ring skeleton thereof is particularly desirable.

More specific examples of the —SO$_2$— containing cyclic group include groups represented by general formulas (a5-r-1) to (a5-r-4) shown below.

[Chemical Formula 32]

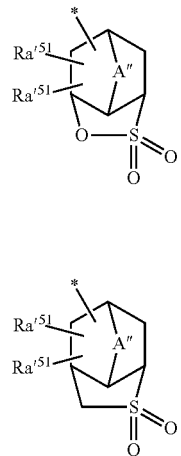

(a5-r-1)

(a5-r-2)

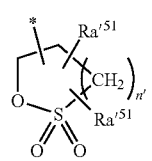

(a5-r-3)

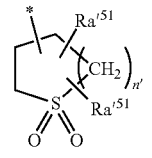

(a5-r-4)

In the formulae, each Ra'$^{51}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom or an alkylene group of 1 to 5 carbon atoms which may contain an oxygen atom or a sulfur atom; and n' represents an integer of 0 to 2.

In general formulae (a5-r-1) and (a5-r-2), A" is the same as defined for A" in general formulae (a2-r-2), (a2-r-3) and (a2-r-5).

Examples of the alkyl group, alkoxy group, halogen atom, halogenated alkyl group, —COOR", —OC(=O)R" and hydroxyalkyl group for Ra'$^{51}$ include the same groups as those described above in the explanation of Ra'$^{21}$ in the general formulas (a2-r-1) to (a2-r-7).

Specific examples of the groups represented by the aforementioned general formulae (a5-r-1) to (a5-r-4) are shown below. In the formulae shown below, "Ac" represents an acetyl group.

[Chemical Formula 33]

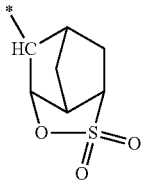

(r-s1-1-1)

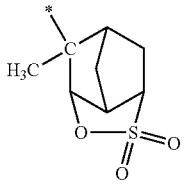

(r-s1-1-2)

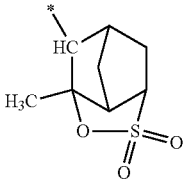

(r-s1-1-3)

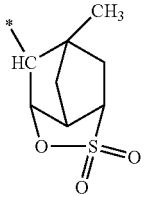

(r-s1-1-4)

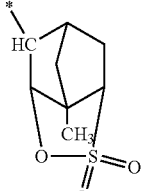

(r-s1-1-5)

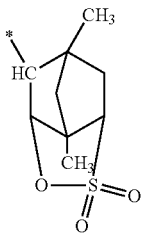

(r-s1-1-6)

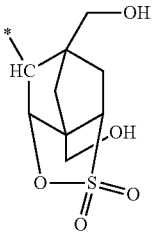

(r-s1-1-7)

[Chemical Formula 34]

(r-s1-1-23) 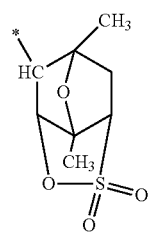
(r-s1-1-24) 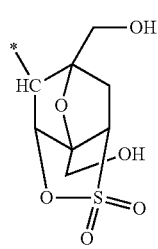
(r-s1-1-25) 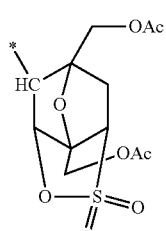
(r-s1-1-26) 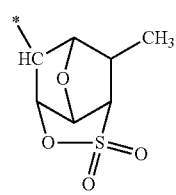
(r-s1-1-27) 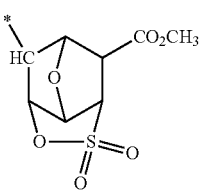
(r-s1-1-28) 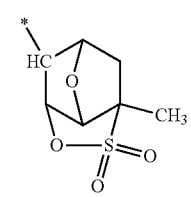
(r-s1-1-29) 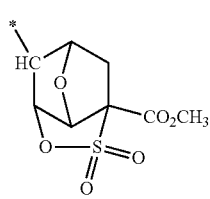
(r-s1-1-30) 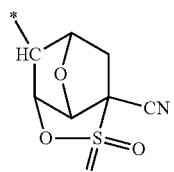
(r-s1-1-31) 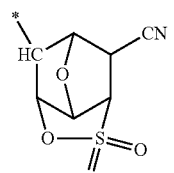
(r-s1-1-32) 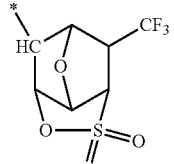
(r-s1-1-33) 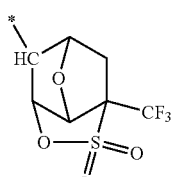
[Chemical Formula 35]
(r-s1-2-1) 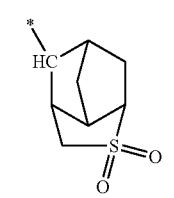
(r-s1-2-2) 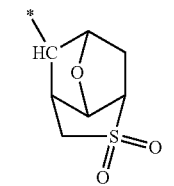
(r-s1-3-1) 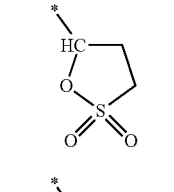
(r-s1-4-1) 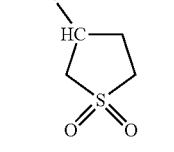
The term "carbonate-containing cyclic group" refers to a cyclic group including a ring containing a —O—C(=O)—O— structure (carbonate ring). The term "carbonate ring" refers to a single ring containing a —O—C(=O)—O— structure, and this ring is counted as the first ring. A carbonate-containing cyclic group in which the only ring structure is the carbonate ring is referred to as a monocyclic group, and groups containing other ring structures are described as polycyclic groups regardless of the structure of the other rings. The carbonate-containing cyclic group may be either a monocyclic group or a polycyclic group.

The carbonate-containing cyclic group is not particularly limited, and an arbitrary group may be used. Specific examples include groups represented by general formulae (ax3-r-1) to (ax3-r-3) shown below.

[Chemical Formula 36]

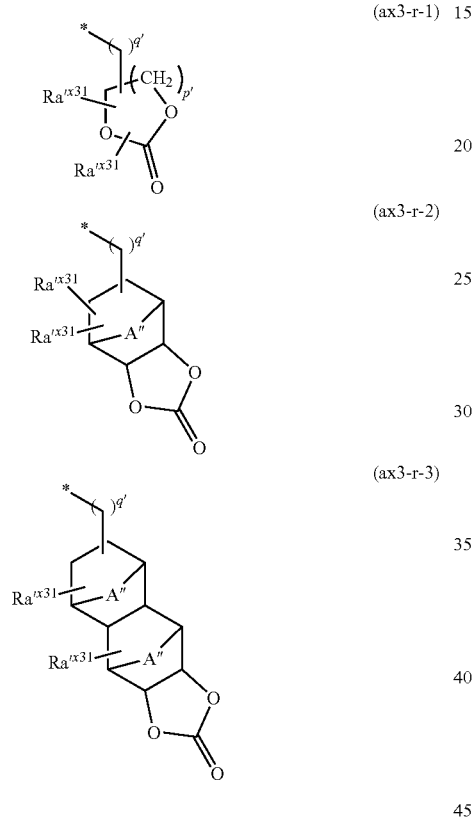

In the formulae, each $Ra'^{x31}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —$SO_2$— containing cyclic group; A" represents an oxygen atom, a sulfur atom or an alkylene group of 1 to 5 carbon atoms which may contain an oxygen atom or a sulfur atom; p' represents an integer of 0 to 3; and q' represents 0 or 1.

In general formulae (ax3-r-2) and (ax3-r-3), A" is the same as defined for A" in general formulae (a2-r-2), (a2-r-3) and (a2-r-5).

Examples of the alkyl group, alkoxy group, halogen atom, halogenated alkyl group, —COOR", —OC(=O)R" and hydroxyalkyl group for $Ra'^{31}$ include the same groups as those described above in the explanation of $Ra'^{21}$ in the general formulas (a2-r-1) to (a2-r-7).

Specific examples of the groups represented by the aforementioned general formulae (ax3-r-1) to (ax3-r-3) are shown below.

[Chemical Formula 37]

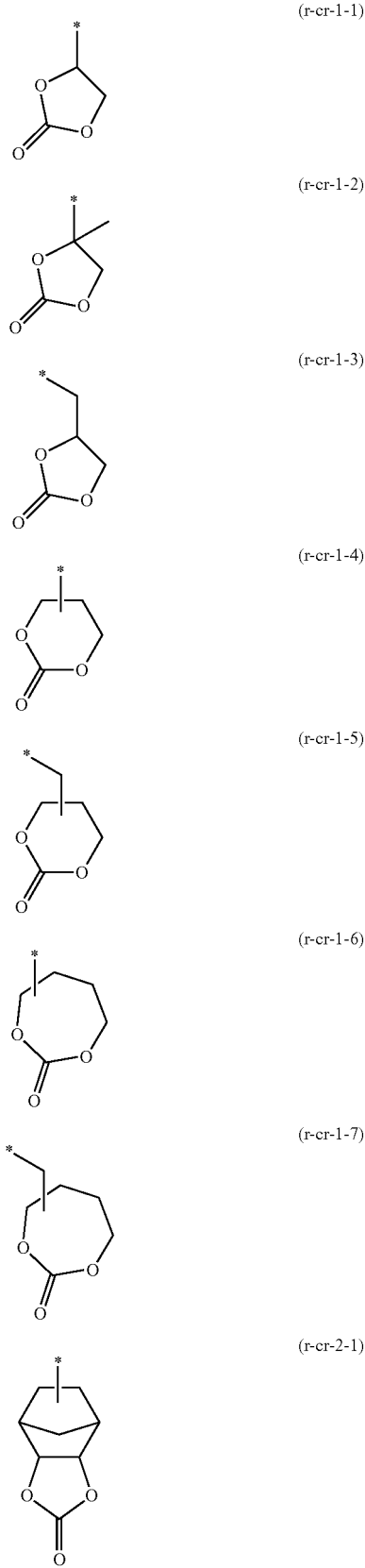

(r-cr-2-2)

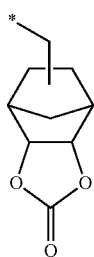

(r-cr-2-3)

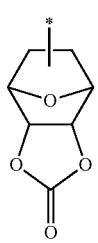

(r-cr-2-4)

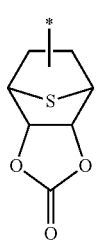

(r-cr-3-1)

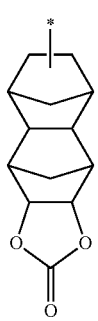

(r-cr-3-2)

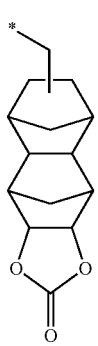

(r-cr-3-3)

[structure]

(r-cr-3-4)

[structure]

(r-cr-3-5)

[structure]

As the structural unit (a2), a structural unit derived from an acrylate ester which may have the hydrogen atom bonded to the carbon atom on the α-position substituted with a substituent is preferable.

The structural unit (a2) is preferably a structural unit represented by general formula (a2-1) shown below.

[Chemical Formula 38]

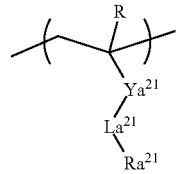

(a-2-1)

In the formula, R represents a hydrogen atom, an alkyl group of 1 to 5 carbon atoms or a halogenated alkyl group of 1 to 5 carbon atoms; $Ya^{21}$ represents a single bond or a divalent linking group; $La^{21}$ represents —O—, —COO—, —CON(R')—, —OCO—, —CONHCO— or —CONHCS—; and R' represents a hydrogen atom or a methyl group; provided that, when $La^{21}$ represents —O—, $Ya^{21}$ does not represents —CO—; and $Ra^{21}$ represents a lactone-containing cyclic group, a carbonate-containing cyclic group or an —$SO_2$— containing cyclic group.

In the formula (a2-1), R is the same as defined above.

The divalent linking group for $Ya^{21}$ is not particularly limited, and preferable examples thereof include a divalent hydrocarbon group which may have a substituent and a divalent linking group containing a hetero atom.

Divalent Hydrocarbon Group which May have a Substituent:

In the case where $Ya^{21}$ is a divalent linking group which may have a substituent, the hydrocarbon group may be either an aliphatic hydrocarbon group or an aromatic hydrocarbon group.

Aliphatic Hydrocarbon Group for $Ya^{21}$

The "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof can be given.

Linear or Branched Aliphatic Hydrocarbon Group

The linear aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

The branched aliphatic hydrocarbon group preferably has 3 to 10 carbon atoms, more preferably 3 to 6 carbon atoms, still more preferably 3 or 4 carbon atoms, and most preferably 3 carbon atoms.

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group may or may not have a substituent. Examples of the substituent include a fluorine atom, a fluorinated alkyl group of 1 to 5 carbon atoms, and a carbonyl group.

Aliphatic Hydrocarbon Group Containing a Ring in the Structure Thereof

As examples of the hydrocarbon group containing a ring in the structure thereof, a cyclic aliphatic hydrocarbon group containing a hetero atom in the ring structure thereof and may have a substituent (a group in which two hydrogen atoms have been removed from an aliphatic hydrocarbon ring), a group in which the cyclic aliphatic hydrocarbon group is bonded to the terminal of the aforementioned chain-like aliphatic hydrocarbon group, and a group in which the cyclic aliphatic group is interposed within the aforementioned linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, isopropoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

The cyclic aliphatic hydrocarbon group may have part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

Aromatic Hydrocarbon Group for $Ya^{21}$

The aromatic hydrocarbon group is a hydrocarbon group having at least one aromatic ring.

The aromatic ring is not particularly limited, as long as it is a cyclic conjugated compound having (4n+2)π (electrons, and may be either monocyclic or polycyclic. The aromatic ring preferably has 5 to 30 carbon atoms, more preferably 5 to 20, still more preferably 6 to 15, and most preferably 6 to 12. Here, the number of carbon atoms within a substituent(s) is not included in the number of carbon atoms of the aromatic hydrocarbon group. Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hetero ring include a pyridine ring and a thiophene ring.

Specific examples of the aromatic hydrocarbon group include a group in which two hydrogen atoms have been removed from the aforementioned aromatic hydrocarbon ring or aromatic hetero ring (arylene group or heteroarylene group); a group in which two hydrogen atoms have been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (a group in which one hydrogen atom has been removed from the aryl group within the aforementioned arylalkyl group such as a benzyl group, a phenethyl group, a 1-naphthylmethyl group, a 2-naphthylmethyl group, a 1-naphthylethyl group, or a 2-naphthylethyl group, or a heteroarylalkyl group). The alkylene group which is bonded to the aforementioned aryl group or heteroaryl group preferably has 1 to 4 carbon atoms, more preferably 1 or 2 carbon atoms, and most preferably 1 carbon atom.

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group of 1 to 5 carbon atoms, and a methyl group, an ethyl group, a propyl group, an n-butyl group or a tert-butyl group is particularly desirable.

As the alkoxy group, the halogen atom and the halogenated alkyl group for the substituent, the same groups as the aforementioned substituent groups for substituting a hydrogen atom within the cyclic aliphatic hydrocarbon group can be used.

Divalent Linking Group Containing a Hetero Atom

In the case where $Ya^{21}$ represents a divalent linking group containing a hetero atom, preferable examples of the linking group include —O—, —C(=O)—O—, —C(=O)—, —O—C(=O)—O—, —C(=O)—NH—, —NH—, —NH—C(=NH)— (may be substituted with a substituent such as an alkyl group, an acyl group or the like), —S—, —S(=O)$_2$—, —S(=O)$_2$—O—, and a group represented by general formula: —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$— or —$Y^{21}$—S(=O)$_2$—O—$Y^{22}$— [in the formulae, $Y^{21}$ and $Y^{22}$ each independently represents a divalent hydrocarbon group which may have a substituent, 0 represents an oxygen atom, and m' represents an integer of 0 to 3].

In the case where the divalent linking group containing a hetero atom is —C(=O)—NH—, —C(=O)—NH—C(=O)—, —NH— or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In general formulae —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$— or —$Y^{21}$—S(=O)$_2$—O—$Y^{22}$—, $Y^{21}$ and $Y^{22}$ each independently represents a divalent hydrocarbon group which may have a substituent. Examples of the divalent hydrocarbon group include the same groups as those described above as the "divalent hydrocarbon group which may have a substituent" in the explanation of the aforementioned divalent linking group.

As $Y^{21}$, a linear aliphatic hydrocarbon group is preferable, more preferably a linear alkylene group, still more preferably a linear alkylene group of 1 to 5 carbon atoms, and a methylene group or an ethylene group is particularly desirable.

As $Y^{22}$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula —[$Y^{21}$—C(=O)—O]$_{m''}$—$Y^{22}$—, m" represents an integer of 0 to 3, preferably an integer of 0 to 2, more preferably 0 or 1, and most preferably 1. Namely, it is particularly desirable that the group represented by the formula —[$Y^{21}$—C(=O)—O] m"—$Y^{22}$— is a group represented by the formula —$Y^{21}$—C(=O)—O—$Y^{22}$—. Among these, a group represented by the formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

$Ya^{21}$ preferably represents an ester bond [—C(=O)—O—], an ether bond (—O—), a linear or branched alkylene group, a combination of these, or a single bond.

In the formula (a2-1), $Ra^{21}$ represents a lactone-containing cyclic group, an —SO$_2$— containing cyclic group or a carbonate-containing cyclic group.

Preferable examples of the lactone-containing cyclic group, the —SO$_2$— containing cyclic group and the carbonate-containing cyclic group for $Ra^{21}$ include groups represented by general formulae (a2-r-1) to (a2-r-7), groups represented by general formulae (a5-r-1) to (a5-r-4) and groups represented by general formulae (ax3-r-1) to (ax3-r-3).

Among the above examples, a lactone-containing cyclic group or a —SO$_2$— containing cyclic group is preferable, and a group represented by general formula (a2-r-1), (a2-r-2), (a2-r-6) or (a5-r-1) is more preferable. Specifically, a group represented by any of chemical formulae (r-1c-1-1) to (r-1c-1-7), (r-1c-2-1) to (r-1c-2-18), (r-1c-6-1), (r-s1-1-1) and (r-s1-1-18) is still more preferable.

As the structural unit (a2) contained in the component (A1), 1 kind of structural unit may be used, or 2 or more kinds may be used.

When the component (A1) contains the structural unit (a2), the amount of the structural unit (a2) based on the combined total (100 mol %) of all structural units constituting the component (A1) is preferably 1 to 80 mol %, more preferably 10 to 70 mol %, still more preferably 10 to 65 mol %, and most preferably 10 to 60 mol %.

When the amount of the structural unit (a2) is at least as large as the lower limit of the above preferable range, the effect of using the structural unit (a2) can be satisfactorily achieved. On the other hand, when the amount of the structural unit (a2) is no more than the upper limit of the above preferable range, a good balance can be achieved with the other structural units, and various lithography properties and pattern shape can be improved.

(Structural Unit (a3))

The structural unit (a3) is a structural unit containing a polar group-containing aliphatic hydrocarbon group (provided that the structural units that fall under the definition of structural units (a1) and (a2) are excluded).

When the component (A) includes the structural unit (a3), it is presumed that the hydrophilicity of the component (A) is enhanced, thereby contributing to improvement in resolution.

Examples of the polar group include a hydroxyl group, cyano group, carboxyl group, or hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups can be selected appropriately from the multitude of groups that have been proposed for the resins of resist compositions designed for use with ArF excimer lasers. The cyclic group is preferably a polycyclic group, more preferably a polycyclic group of 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

As the structural unit (a3), there is no particular limitation as long as it is a structural unit containing a polar group-containing aliphatic hydrocarbon group, and an arbitrary structural unit may be used.

The structural unit (a3) is preferably a structural unit derived from an acrylate ester which may have the hydrogen atom bonded to the carbon atom on the α-position substituted with a substituent and contains a polar group-containing aliphatic hydrocarbon group.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 39]

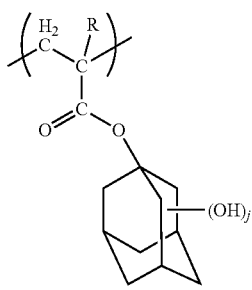
(a3-1)

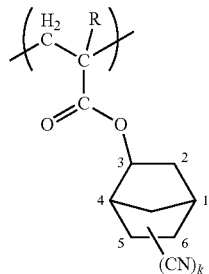
(a3-2)

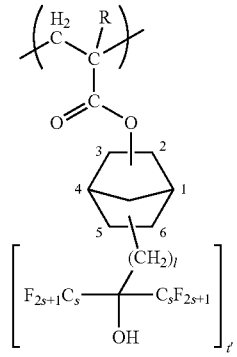
(a3-3)

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1.1 is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3) contained in the component (A), 1 kind of structural unit may be used, or 2 or more kinds may be used.

When the component (A1) includes the structural unit (a3), the amount of the structural unit (a3) based on the combined total (100 mol %) of all structural units constituting the component (A1) is preferably 5 to 50 mol %, more preferably 5 to 40 mol %, and still more preferably 5 to 25 mol %.

When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

(Structural Unit (a4))

The structural unit (a4) is a structural unit containing an acid non-dissociable, aliphatic cyclic group.

When the component (A1) includes the structural unit (a4), dry etching resistance of the resist pattern to be formed is improved. Further, the hydrophobicity of the component (A) is further improved. Increase in the hydrophobicity contributes to improvement in terms of resolution, shape of the resist pattern and the like, particularly in a solvent developing process.

An "acid non-dissociable, aliphatic cyclic group" in the structural unit (a4) refers to a cyclic group which is not dissociated by the action of the acid (e.g., acid generated from the component (B) described later) upon exposure, and remains in the structural unit.

As the structural unit (a4), a structural unit which contains a non-acid-dissociable aliphatic cyclic group, and is also derived from an acrylate ester is preferable. As the cyclic group, any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecyl group, adamantyl group, tetracyclododecyl group, isobornyl group, and norbornyl group is particularly desirable. These polycyclic groups may be substituted with a linear or branched alkyl group of 1 to 5 carbon atoms.

Specific examples of the structural unit (a4) include structural units represented by general formulae (a4-1) to (a4-7) shown below.

[Chemical Formula 40]

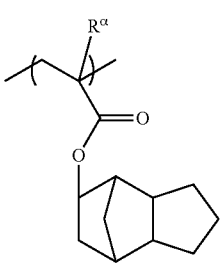
(a4-1)

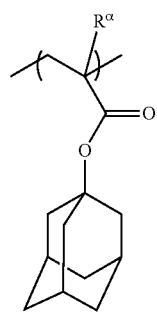
(a4-2)

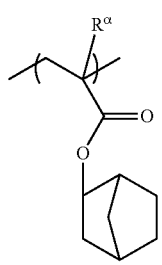
(a4-3)

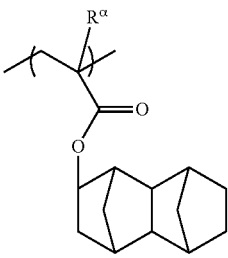
(a4-4)

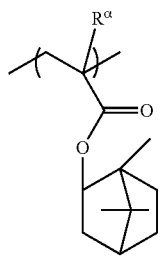
(a4-5)

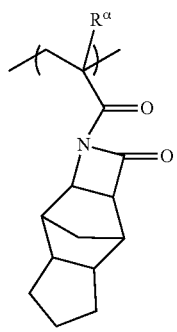
(a4-6)

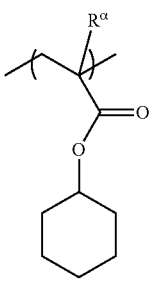
(a4-7)

In the formulae, $R^{\alpha}$ is the same as defined above.

As the structural unit (a4) contained in the component (A1), 1 type of structural unit may be used, or 2 or more types may be used.

When the component (A1) includes the structural unit (a4), the amount of the structural unit (a4) based on the combined total of all structural units constituting the component (A1) is preferably 1 to 30 mol %, and more preferably 3 to 20 mol %.

When the amount of the structural unit (a4) is at least as large as the lower limit of the above-mentioned preferable range, the effect of using the structural unit (a4) can be satisfactorily achieved. On the other hand, when the amount of the structural unit (a4) is no more than the upper limit of the above-mentioned preferable range, a good balance can be achieved with the other structural units.

The component (A) can be obtained, for example, by a conventional radical polymerization or the like of the monomers corresponding with each of the structural units, using a radical polymerization initiator such as azobisisobutyronitrile (AIBN) or dimethyl 2,2'-azobis(isobutyrate).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

In the present invention, the weight average molecular weight (Mw) (the polystyrene equivalent value determined by gel permeation chromatography) of the component (A) is not particularly limited, but is preferably 1,000 to 50,000, more preferably 1,500 to 30,000, and most preferably 2,000 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

In the resist composition of the present invention, as the component (A), one type may be used, or two or more types of compounds may be used in combination.

In the resist composition of the present invention, the amount of the component (A) can be appropriately adjusted depending on the thickness of the resist film to be formed, and the like.

<Component (F)>

In the present embodiment, the component (F) includes a fluorine resin component (F1) (hereafter, sometimes referred to as "component (F1)") having a structural unit (f1) derived from a compound represented by general formula (f1-1) shown below.

[Chemical Formula 41]

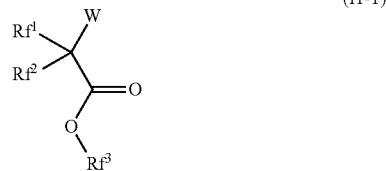

(f1-1)

In the formula, W represents a polymerizable group-containing group; $Rf^1$ and $Rf^2$ each independently represents a hydrogen atom or an electron-withdrawing group; $Rf^3$ represents a hydrocarbon group which may have a substituent; provided that at least one of $Rf^1$ to $Rf^3$ has a fluorine atom; in the case where $Rf^3$ is an aliphatic hydrocarbon group which may have a substituent, $Rf^3$ has 5 or more carbon atoms; and in the case where $Rf^3$ is an aromatic hydrocarbon group which may have a substituent, 3 or more hydrogen atoms of the aromatic ring are substituted with electron-withdrawing groups, and at least one of $Rf^1$ and $Rf^2$ is an electron-withdrawing group.

(Structural Unit (f1))

The structural unit (f1) is a structural unit derived from a compound represented by the aforementioned general formula (f1-1).

In general formula (f1-1), W represents a polymerizable group-containing group. A "polymerizable group" refers to a group that renders a compound containing the group polymerizable by a radical polymerization or the like, for example, a group having a carbon-carbon multiple bond such as an ethylenic double bond.

Examples of the polymerizable group include a vinyl group, an allyl group, an acryloyl group, a methacryloyl group, a fluorovinyl group, a difluorovinyl group, a trifluorovinyl group, a difluorotrifluoromethylvinyl group, a trifluoroallyl group, a perfluoroallyl group, a trifluoromethylacryloyl group, a nonylfluorobutylacryloyl group, a vinyl ether group, a fluorine-containing vinyl ether group, an allyl ether group, an fluorine-containing allyl ether group, a styryl group, a vinylnaphthyl group, a fluorine-containing styryl group, a fluorine-containing vinylnaphthyl group, a norbornyl group, a fluorine-containing norbornyl group, and a silyl group.

The polymerizable group-containing group for W may be a group constituted of only a polymerizable group, or constituted of a polymerizable group and a group other than a polymerizable group. As the polymerizable group-containing group, a group represented by the formula $Rw^2$-$Lw^1$- [in the formula, $Rw^2$ represents a hydrocarbon group which contains an ethylenic double bond and which may have a substituent, and $Lw^1$ represents a divalent linking group containing a hetero atom or a single bond] is preferable.

The hydrocarbon group for $Rw^2$ is not particularly limited, as long as it contains an ethylenic double bond, and may be a chain-like hydrocarbon group, or a hydrocarbon group containing a ring in the structure thereof.

As the chain-like hydrocarbon group for $Rw^2$, a chain-like alkenyl group is preferable. The chain-like alkenyl group may be linear or branched, and preferably has 2 to 10 carbon atoms, more preferably 2 to 5 carbon atoms, still more preferably 2 to 4 carbon atoms, and particularly preferably 2 or 3 carbon atoms.

Examples of linear alkenyl groups include a vinyl group, a propenyl group (an allyl group) and a butynyl group. Examples of branched alkenyl groups include a 1-methylpropenyl group and a 2-methylpropenyl group. Of these, a vinyl group or a propenyl group is preferable.

Examples of the hydrocarbon group for $Rw^2$ which contains a ring the structure thereof include an unsaturated alicyclic group containing an ethylenic double bond in the ring skeleton, a group in which such unsaturated alicyclic group is bonded to a terminal of a linear or branched aliphatic hydrocarbon group, and a group in which a chain-like alkenyl group is bonded to a terminal of a cyclic hydrocarbon group.

As the unsaturated aliphatic hydrocarbon cyclic group which contains an ethylenic double bond in the ring structure thereof, for example, a group in which one hydrogen atom has been removed from a monocyclic or polycycic cycloolefine can be mentioned. The cycloolefine preferably has 3 to 20 carbon atoms, and more preferably 3 to 12 carbon atoms. Examples of the cycloolefine include cyclopropene, cyclobutene, cyclopentene, cyclohexene, cycloheptene, cyclooctene, norbornene, 7-oxanorbornene, tetracyclododecene. Among these examples, norbornene is preferable.

With respect to the group in which the unsaturated aliphatic hydrocarbon cyclic group is bonded to the terminal of the aforementioned linear or branched aliphatic hydrocarbon group, the linear or branched aliphatic hydrocarbon group to which the unsaturated aliphatic hydrocarbon cyclic group is to be bonded may be saturated or unsaturated. In general, the linear or branched aliphatic hydrocarbon group is preferably saturated.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—CH$_2$—], an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

As the branched aliphatic hydrocarbon group, branched alkylene groups are preferred, and specific examples include various alkylalkylene groups, including alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —C(CH$_2$CH$_3$)$_2$—CH$_2$—; alkyltrimethylene groups such as —CH(CH$_3$)CH$_2$CH$_2$—, and —CH$_2$CH(CH$_3$)CH$_2$—; and alkyltetramethylene groups such as —CH(CH$_3$)CH$_2$CH$_2$CH$_2$—, and —CH$_2$CH(CH$_3$)CH$_2$CH$_2$—. As the alkyl group within the alkylalkylene group, a linear alkyl group of 1 to 5 carbon atoms is preferable.

With respect to the group in which a chain-like alkenyl group is bonded to the terminal of the a cyclic hydrocarbon group, as the chain-like alkenyl group, the same groups as those described above can be mentioned.

The cyclic hydrocarbon group to which the chain-like alkenyl group is to be bonded may be a cyclic aliphatic hydrocarbon group (aliphatic cyclic group) or a cyclic aromatic hydrocarbon group (aromatic cyclic group).

The cyclic aliphatic hydrocarbon group may be either saturated or unsaturated. In general, the cyclic aliphatic hydrocarbon group is preferably saturated.

The aliphatic cyclic group preferably has 3 to 20 carbon atoms, and more preferably 3 to 12 carbon atoms.

The aliphatic cyclic group may be either a monocyclic group or a polycyclic group. As the monocyclic aliphatic hydrocarbon group, a group in which one hydrogen atoms have been removed from a monocycloalkane is preferable. The monocycloalkane preferably has 3 to 6 carbon atoms, and specific examples thereof include cyclopentane and cyclohexane. As the polycyclic aliphatic cyclic group, a group in which 2 hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aromatic cyclic group is a group in which one hydrogen atom has been removed from an aromatic ring.

The aromatic hydrocarbon ring preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group for RV include a group in which 1 hydrogen atom has been removed from the aforementioned aromatic hydrocarbon ring or aromatic hetero ring (an aryl group or a hetero aryl group); a group in which 1 hydrogen atom has been removed from an aromatic compound containing 2 or more aromatic rings (such as biphenyl and fluorene); and a group in which 1 hydrogen atom of the aforementioned aromatic hydrocarbon ring or aromatic hetero ring has been substituted with an alkylene group (such as a benzyl group, a phenethyl group, a 1-naphthylmethyl group, a 2-naphthylmethyl group, a 1-naphthylethyl group or a 2-naphthylethyl group). The alkylene group bonded to the aforementioned aromatic hydrocarbon ring or the aromatic hetero ring preferably has 1 to 4 carbon atoms, more preferably 1 or 2 carbon atoms, and most preferably 1 carbon atom.

Among these examples, as the aromatic hydrocarbon group for Rf$^3$, an arylalkyl group is preferable, a benzyl group, a phenethyl group, a 1-naphthylmethyl group, a 2-naphthylmethyl group, a 1-naphthylethyl group or a 2-naphthylethyl group is more preferable, and a benzyl group is still more preferable.

In general formula (f1-1), Rf$^1$ and Rf$^2$ each independently represents a hydrogen atom or an electron-withdrawing group.

Examples of the electron-withdrawing group include a halogen atom, a halogenated alkyl group, a halogenated alkoxy group, a halogenated aryloxy group, a halogenated alkylamino group, a halogenated alkylthio group, an alkyloxycarbonyl group, an aryloxycarbonyl group, a cyano group, a nitro group, a dialkylphosphono group, a diarylphosphono group, an alkylsulfonyl group, an arylsulfonyl group, a sulfonyloxy group, acylthio group, a sulfamoyl group, a thiocyanate group and a thiocarbonyl group.

Among these examples, a halogen atom or a halogenated alkyl group is preferable.

As the halogenated alkyl group, a halogenated alkyl group of 1 to 10 carbon atoms is preferable. The halogenated alkyl group of 1 to 10 carbon atoms represented by R is a group in which part or all of the hydrogen atoms of the aforementioned alkyl group of 1 to 10 carbon atoms have been substituted with halogen atoms. Examples of the halogen atom include a fluorine atom, a chlorine atom, a bromine atom and an iodine atom, and a fluorine atom is particularly desirable.

Among these examples, as Rf$^1$ and Rf$^2$, a trifluoromethyl group, a fluorine atom or a hydrogen atom is preferable.

In general formula (f1-1), Rf$^3$ represents an aliphatic hydrocarbon group which may have a substituent. The hydrocarbon group for Rf$^3$ may be either an aliphatic hydrocarbon group, or an aromatic hydrocarbon group.

In the case where Rf$^3$ is an aliphatic hydrocarbon group which may have a substituent, Rf$^3$ has 5 or more carbon atoms.

The aliphatic hydrocarbon group as the hydrocarbon group for Rf$^3$ may be either saturated or unsaturated. In general, the aliphatic hydrocarbon group is preferably saturated.

Specific examples of the aliphatic hydrocarbon group include a hydrocarbon group having 5 or more carbon atoms represented by general formula (f1-r-1') shown below.

[Chemical Formula 42]

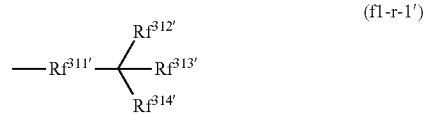

(f1-r-1')

In the formula, $Rf^{311'}$ represents an alkylene group; $Rf^{312'}$ to $Rf^{314'}$ each independently represents a hydrogen atom, an alkyl group, a fluorine atom or a fluorinated alkyl group.

In general formula (f1-r-1'), $Rf^{311'}$ represents an alkylene group. The alkylene group for $Rf^{311'}$ may be linear, branched or cyclic, or a combination thereof.

The linear alkylene group for $Rf^{311'}$ preferably has 1 to 10 carbon atoms, more preferably 1 to 6 carbon atoms, still more preferably 1 to 4 carbon atoms, and most preferably 1 to 3 carbon atoms.

Specific examples of the linear alkylene group include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

The branched alkylene group for $Rf^{311'}$ preferably has 3 to 10 carbon atoms, more preferably 3 to 6 carbon atoms, still more preferably 3 or 4 carbon atoms, and most preferably 3 carbon atoms.

Specific examples of the alkylene group for $Rf^{311'}$ include an alkylmethylene group, such as —$CH(CH_3)$—, —$CH(CH_2CH_3)$—, —$C(CH_3)_2$—, —$C(CH_3)(CH_2CH_3)$—, $C(CH_3)(CH_2CH_2CH_3)$— or —$C(CH_2CH_3)_2$—; an alkylethylene group, such as —$CH(CH_3)CH_2$—, —$CH(CH_3)CH(CH_3)$—, —$C(CH_3)_2CH_2$—, —$CH(CH_2CH_3)CH_2$— or —$C(CH_2CH_3)_2$—$CH_2$—; an alkyltrimethylene group, such as —$CH(CH_3)CH_2CH_2$— or —$CH_2CH(CH_3)CH_2$—; and an alkyltetramethylene group, such as —$CH(CH_3)CH_2CH_2CH_2$— or —$CH_2CH(CH_3)CH_2CH_2$—. As the alkyl group within the alkylalkylene group, a linear alkyl group of 1 to 5 carbon atoms is preferable.

The cyclic alkylene group for $Rf^{311'}$ preferably has 3 to 20 carbon atoms, and more preferably 3 to 12 carbon atoms.

The cyclic alkylene group for $Rf^{311'}$ may be polycyclic or monocyclic. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

Among these examples, as the alkylene group for $Rf^{311'}$, a linear alkylene group is preferable, and a methylene group [—$CH_2$—], an ethylene group [—$(CH_2)_2$—] or a trimethylene group [—$(CH_2)_3$—] is more preferable.

In general formula (f1-r-1'), $Rf^{312'}$ to $Rf^{314'}$ each independently represents a hydrogen atom, an alkyl group, a fluorine atom or a fluorinated alkyl group.

The alkyl group for $Rf^{312'}$ to $Rf^{314'}$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group.

Examples of the fluorinated alkyl group for $Rf^{312'}$ to $Rf^{314'}$ include a group in which part or all of the hydrogen atoms within the aforementioned alkyl group has substituted with fluorine.

Among these examples, as $Rf^{312'}$ to $Rf^{314'}$, a hydrogen atom, a linear alkyl group, a fluorine atom or a linear fluorinated alkyl group is preferable, and a hydrogen atom, a methyl group, a fluorine atom or a trifluoromethyl group is more preferable.

The aliphatic hydrocarbon group for $Rf^3$ may have a substituent. Examples of the substituent include —$R^{P1}$, —$R^{P2}$—O—$R^{P1}$, —$R^{P2}$—CO—$R^{P1}$, —$R^{P2}$—CO—$OR^{P1}$, —$R^{P2}$—O—CO—$R^{P1}$, —$R^{P2}$—OH, —$R^{P2}$—CN or —$R^{P2}$—COOH (hereafter, these substituents are sometimes collectively referred to as "$Ra^{05}$"). $R^{P1}$ and $R^{P2}$ are the same as defined above.

In general formula (f1-1), in the case where $Rf^3$ is an aromatic hydrocarbon group which may have a substituent, 3 or more hydrogen atoms of the aromatic ring are substituted with electron-withdrawing groups, and at least one of $Rf^1$ and $Rf^2$ is an electron-withdrawing group. In the case where $Rf^3$ is an aromatic hydrocarbon group which may have a substituent, it is preferable that all hydrogen atoms of the aromatic ring are substituted with electron-withdrawing groups.

Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group for $Rf^3$ include a group in which 1 hydrogen atom has been removed from the aforementioned aromatic hydrocarbon ring or aromatic hetero ring (an aryl group or a hetero aryl group); a group in which 1 hydrogen atom has been removed from an aromatic compound containing 2 or more aromatic rings (such as biphenyl and fluorene); and a group in which 1 hydrogen atom of the aforementioned aromatic hydrocarbon ring or aromatic hetero ring has been substituted with an alkylene group (such as a benzyl group, a phenethyl group, a 1-naphthylmethyl group, a 2-naphthylmethyl group, a 1-naphthylethyl group or a 2-naphthylethyl group). The alkylene group bonded to the aforementioned aromatic hydrocarbon ring or the aromatic hetero ring preferably has 1 to 4 carbon atoms, more preferably 1 or 2 carbon atoms, and most preferably 1 carbon atom.

Among these examples, as the aromatic hydrocarbon group for $Rf^3$, an arylalkyl group is preferable, a benzyl group, a phenethyl group, a 1-naphthylmethyl group, a 2-naphthylmethyl group, a 1-naphthylethyl group or a 2-naphthylethyl group is more preferable, and a benzyl group is still more preferable.

Examples of the substituent for the aromatic hydrocarbon group represented by $Rf^3$ include a methyl group, an ethyl group, a propyl group, a hydroxyl group, a carboxyl group, a halogen atom (a fluorine atom, a chlorine atom, a bromine atom, or the like), an alkoxy group (a methoxy group, an ethoxy group, a propoxy group, a butoxy group, or the like), and an alkyloxycarbonyl group.

The electron-withdrawing group which the aromatic hydrocarbon group for $Rf^3$ has is the same as defined for the electron-withdrawing group for the aforementioned $Rf^1$ and $Rf^2$. Among these examples, as the electron-withdrawing group which the aromatic hydrocarbon group for $Rf^3$ has, a halogen atom or a halogenated alkyl group is preferable, a fluorine atom or a fluorinated alkyl group is more preferable, and a fluorine atom or a trifluoromethyl group is still more preferable.

In the present embodiment, the structural unit (f1) is preferably a structural unit represented by general formula (f1-1-1) shown below or a structural unit represented by general formula (f1-1-2) shown below.

[Chemical Formula 43]

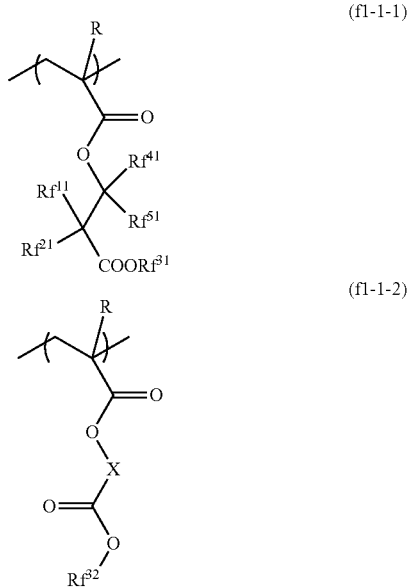

In the formula, each R independently represents a hydrogen atom, an alkyl group of 1 to 5 carbon atoms or a halogenated alkyl group of 1 to 5 carbon atoms; $Rf^{11}$ and $Rf^{21}$ each independently represents a hydrogen atom or an electron-withdrawing group; provided that at least one of $Rf^{11}$ and $Rf^{21}$ is an electron-withdrawing group; $Rf^{31}$ is a hydrocarbon group of 5 or more carbon atoms represented by general formula (f1-r-1) shown below or an aromatic hydrocarbon group which may have a substituent; in the case where $Rf^{31}$ is an aromatic hydrocarbon group which may have a substituent, 3 or more hydrogen atoms of the aromatic ring are substituted with electron-withdrawing groups, and at least one of $Rf^{11}$ and $Rf^{31}$ has a fluorine atom; $Rf^{41}$ and $Rf^{51}$ a hydrogen atom, an alkyl group or a fluorinated alkyl group; X represents a divalent linking group having no acid dissociable portion; and $Rf^{32}$ is a hydrocarbon group of 5 or more carbon atoms represented by general formula (f1-r-1) shown below.

[Chemical Formula 44]

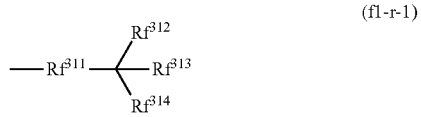

In the formula, $Rf^{311}$ represents an alkylene group; $Rf^{312}$ to $Rf^{314}$ each independently represents a hydrogen atom, an alkyl group, a fluorine atom or a fluorinated alkyl group; provided that at least one of $Rf^{312}$ to $Rf^{314}$ is a fluorine atom or a fluorinated alkyl group.

In general formulae (f1-1-1) and (f1-1-2), R is the same as defined above.

In general formula (f1-1-1), $Rf^{11}$ and $Rf^{21}$ each independently represents a hydrogen atom or an electron-withdrawing group, provided that at least one of $Rf^{11}$ and $Rf^{21}$ is an electron-withdrawing group; The electron-withdrawing group for $Rf^{11}$ and $Rf^{21}$ is the same as defined for the electron-withdrawing group for $Rf^{1}$ and $Rf^{2}$. Among these examples, as $Rf^{11}$ and $Rf^{21}$ a hydrogen atom, a halogen atom or a halogenated alkyl group is preferable, a hydrogen atom, a fluorine atom or a fluorinated alkyl group is more preferable, and a fluorine atom is still more preferable.

In general formula (f1-1-1), $Rf^{31}$ is a hydrocarbon group of 5 or more carbon atoms represented by general formula (f1-r-1) shown below or an aromatic hydrocarbon group which may have a substituent.

In general formula (f1-r-1), $Rf^{311}$ represents an alkylene group, and is the same as defined for the alkylene group for the aforementioned $Rf^{311'}$. Among these examples, as the alkylene group for $Rf^{311}$, a linear alkylene group is preferable, a methylene group [—$CH_2$—], an ethylene group [—$(CH_2)_2$—] or a trimethylene group [—$(CH_2)_3$—] is more preferable.

In general formula (f1-r-1), $Rf^{312}$ to $Rf^{314}$ each independently represents a hydrogen atom, an alkyl group, a fluorine atom or a fluorinated alkyl group. However, at least one of $Rf^{312}$ to $Rf^{314}$ is a fluorine atom or a fluorinated alkyl group. The alkyl group and the fluorinated alkyl group for $Rf^{312}$ to $Rf^{314}$ are the same as defined for the alkyl group and the fluorinated alkyl group for $Rf^{312'}$ to $Rf^{314'}$. Among these examples, as $Rf^{312}$ to $Rf^{314}$, a hydrogen atom, a linear alkyl group of 1 to 5 carbon atoms, a fluorine atom or a linear fluorinated alkyl group of 1 to 5 carbon atoms is preferable, and a hydrogen atom, a methyl group, a fluorine atom or a trifluoromethyl group is more preferable.

The aromatic hydrocarbon group for $Rf^{31}$ (which may have a substituent) is the same as defined for the aromatic hydrocarbon group for $Rf^{3}$ (which may have a substituent). Among these examples, as the aromatic hydrocarbon group for $Rf^{31}$, an arylalkyl group is preferable, a benzyl group, a phenethyl group, a 1-naphthylmethyl group, a 2-naphthylmethyl group, a 1-naphthylethyl group or a 2-naphthylethyl group is more preferable, and a benzyl group is still more preferable.

In general formula (f1-r-1), $Rf^{41}$ and $Rf^{51}$ each independently represents a hydrogen atom, an alkyl group or a fluorinated alkyl group. The alkyl group and the fluorinated alkyl group for $Rf^{41}$ and $Rf^{51}$ are the same as defined for the alkyl group and the fluorinated alkyl group for $Rf^{312'}$ to $Rf^{314'}$. Among these examples, as $Rf^{41}$ and $Rf^{51}$, a hydrogen atom, a linear alkyl group of 1 to 3 carbon atoms or a linear fluorinated alkyl group of 1 to 3 carbon atoms is preferable, and it is more preferable that at least one of $Rf^{41}$ and $Rf^{51}$ is a hydrogen atom, and the other is a linear alkyl group of 1 to 3 carbon atoms.

In general formula (f1-r-2), X represents a divalent linking group having no acid dissociable portion.

An "acid dissociable portion" refers to a portion within the organic group which is dissociated from the organic group by the action of acid generated upon exposure.

Examples of the divalent linking group having no acid dissociable portion for X include a divalent hydrocarbon group which may have a substituent, and a divalent group containing a hetero atom.

(Hydrocarbon Group which May have a Substituent)

With respect to the group other than the polymerizable group, the hydrocarbon group may "have a substituent" means that part or all of the hydrogen atoms of the hydrocarbon group may be substituted with groups or atoms other than hydrogen atoms.

The hydrocarbon group may be either an aliphatic hydrocarbon group or an aromatic hydrocarbon group.

An "aliphatic hydrocarbon group" refers to a hydrocarbon group that has no aromaticity. The aliphatic hydrocarbon group may be either saturated or unsaturated, but in general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 8, still more preferably 1 to 5, still more preferably 1 to 3, and most preferably 2.

As a linear aliphatic hydrocarbon group, a linear alkylene group is preferable, and specific examples include a methylene group, an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

As a branched aliphatic hydrocarbon group, a branched alkylene group is preferable, and specific examples include alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —CH(CH$_2$CH$_3$)CH$_2$—; alkyltrimethylene groups such as —CH(CH$_3$)CH$_2$CH$_2$—, and —CH$_2$CH(CH$_3$)CH$_2$—; and alkyltetramethylene groups such as —CH(CH$_3$)CH$_2$CH$_2$CH$_2$—, and —CH$_2$CH(CH$_3$)CH$_2$CH$_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated lower alkyl group of 1 to 5 carbon atoms, and an oxygen atom (=O).

As examples of the aliphatic hydrocarbon group containing a ring, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include a lower alkyl group of 1 to 5 carbon atoms, a fluorine atom, a fluorinated lower alkyl group of 1 to 5 carbon atoms, and an oxygen atom (=O).

Examples of aromatic hydrocarbon groups include a divalent aromatic hydrocarbon group in which one hydrogen atom has been removed from a benzene ring of a monovalent aromatic hydrocarbon group such as a phenyl group, a biphenyl group, a fluorenyl group, a naphthyl group, an anthryl group or a phenanthryl group;

an aromatic hydrocarbon group in which part of the carbon atoms constituting the ring of the aforementioned divalent aromatic hydrocarbon group has been substituted with a hetero atom such as an oxygen atom, a sulfur atom or a nitrogen atom; and an aromatic hydrocarbon group in which one hydrogen atom has been removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

Among these examples, the aforementioned divalent aromatic hydrocarbon group is preferable, and an aromatic hydrocarbon group in which one hydrogen atom has been removed from a phenyl group, or an aromatic hydrocarbon group in which one hydrogen atom has been removed from a naphthyl group is particularly desirable.

The alkyl chain within the arylalkyl group preferably has 1 to 4 carbon atom, more preferably 1 or 2, and most preferably 1.

The aromatic hydrocarbon group may or may not have a substituent. Examples of the substituent include a lower alkyl group of 1 to 5 carbon atoms, a fluorine atom, a fluorinated lower alkyl group of 1 to 5 carbon atoms, and an oxygen atom (=O).

Among the above-mentioned examples, as the hydrocarbon group which may have a substituent, a linear, branched or cyclic aliphatic hydrocarbon group or a divalent aromatic hydrocarbon group is preferable, and a methylene group, and ethylene group, —CH(CH$_3$)—, a group in which one hydrogen atom has been removed from a tetracyclododecyl group, or an aromatic hydrocarbon group in which one hydrogen atom has been removed from a phenyl group is particularly desirable.

(Divalent Linking Group Containing a Hetero Atom)

A hetero atom is an atom other than carbon and hydrogen, and examples thereof include an oxygen atom, a nitrogen atom, a sulfur atom and a halogen atom.

Examples of the divalent linking group containing a hetero atom include —O—, —C(=O)—, —C(=O)—O—, a carbonate bond (—O—C(=O)—O—), —NH—, —NR$^{04}$— (wherein R$^{04}$ represents an alkyl group), —NH—C(=O)—, =N—, and a combination of any of these "groups" with a divalent hydrocarbon group.

As examples of the divalent hydrocarbon group, the same groups as those described above for the hydrocarbon group which may have a substituent can be given, and a linear or branched aliphatic hydrocarbon group is preferable.

Among the above-mentioned examples, as the divalent linking group containing a hetero atom, a combination of any of the aforementioned "groups" with a divalent hydrocarbon group is preferable. More specifically, it is particularly desirable to use a combination of any of the aforementioned "groups" with the aforementioned aliphatic hydrocarbon group, or a combination of the aforementioned aliphatic hydrocarbon group, any of the aforementioned "groups" and the aforementioned aliphatic hydrocarbon group.

In general formula (f1-1-2), Rf$^{32}$ is a hydrocarbon group of 5 or more carbon atoms represented by general formula (f1-r-1), and is the same as defined above.

Specific examples of the structural unit (f1) are shown below. In the formulae, R is the same as defined above.

[Chemical Formula 45]

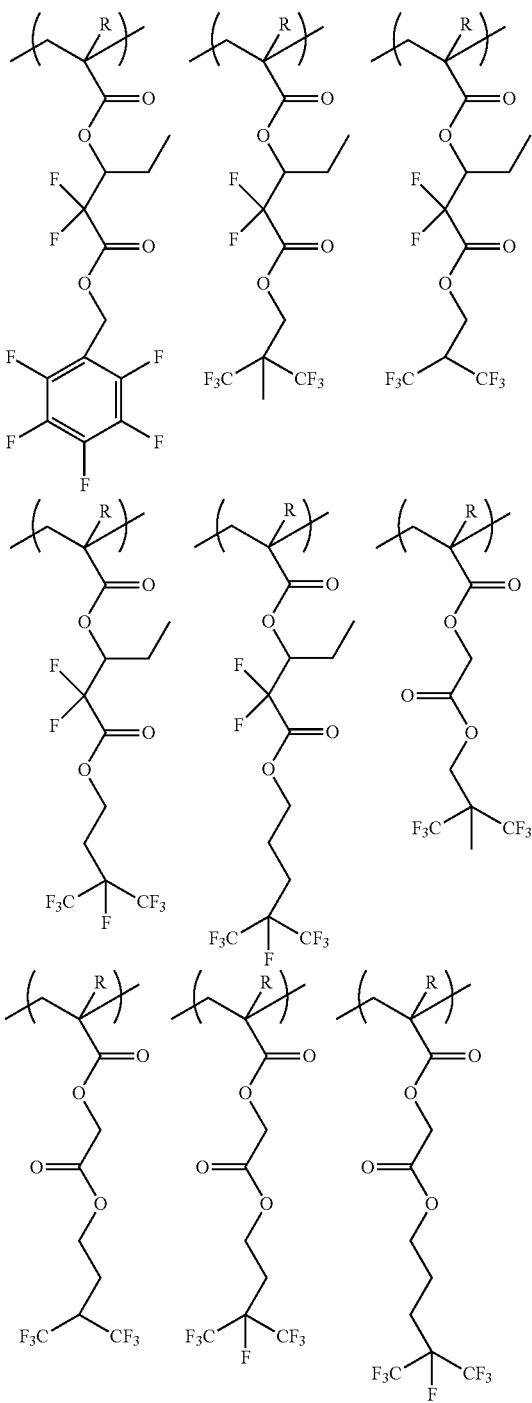

As the structural unit (f1) contained in the component (F1), 1 kind of structural unit may be used, or 2 or more kinds of structural units may be used.

In the component (F1), the amount of the structural unit (f1) based on the combined total (100 mol %) of all structural units constituting the component (F1) is preferably 20 to 100 mol %, more preferably 30 to 100 mol %, and most preferably 40 to 100 mol %.

When the amount of the structural unit (f1) is at least as large as the lower limit of the above-mentioned range, the hydrophobicity of the resist film surface may be enhanced in the formation of a resist pattern. Also, the hydrophilicity of the resist film after exposure is enhanced. Furthermore, a resist film exhibiting excellent lithography properties can be obtained.

When the amount of the structural unit (f1) is no more than the upper limit of the above-mentioned range, a good balance may be achieved with the other structural units.

(Other Structural Units)

The component (F1) may have a structural unit other than structural unit (f1) (hereafter, sometimes referred to as "structural unit (f2)"). Examples of the structural unit (f2) include at least one member selected from the group consisting of the aforementioned structural unit (a1), the aforementioned structural unit (a2), the aforementioned structural unit (a3) and the aforementioned structural unit (a4).

As the structural unit (f2) contained in the component (F1), 1 kind of structural unit may be used, or 2 or more kinds may be used.

When the component (F1) includes the structural unit (f2), the amount of the structural unit (f2) based on the combined total (100 mol %) of all structural units constituting the component (F1) is preferably 1 to 80 mol %, more preferably 1 to 70 mol %, and still more preferably 10 to 60 mol %.

When the amount of the structural unit (f2) is at least as large as the lower limit of the above-mentioned range, a high hydrophobicity may be achieved during formation of a resist pattern, and a resist film exhibiting excellent lithography properties may be obtained. When the amount of the structural unit (f2) is no more than the upper limit of the above-mentioned range, a good balance may be achieved with the other structural units.

The component (F) can be obtained, for example, by a conventional radical polymerization or the like of the monomers corresponding with the desired structural units, using a radical polymerization initiator such as azobisisobutyronitrile (AIBN) or dimethyl 2,2'-azobis(isobutyrate).

The weight average molecular weight (Mw) (the polystyrene equivalent value determined by gel permeation chromatography) of the component (F) is not particularly limited, but is preferably 2,000 to 100,000, more preferably 3,000 to 100,000, still more preferably 4,000 to 60,000, and most preferably 5,000 to 60,000.

When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, a high hydrophobicity may be obtained.

Further, the dispersity (Mw/Mn) is preferably 1.0 to 5.0, more preferably 1.0 to 3.0, and most preferably 1.0 to 2.5.

In the resist composition of the present invention, the amount of the component (F) relative to 100 parts by weight of the component (A) is in the range of 0.1 to 20 parts by weight, preferably 1 to 10 parts by weight, and more preferably 1 to 5 parts by weight. When the amount of the component (F) is no more than the upper limit of the above-mentioned range, the hydrophobicity of a resist film formed using the resist film is enhanced. Further, generation of defects may be suppressed. Furthermore, a favorable hydrophobicity suitable for immersion lithography can be achieved. On the other hand, when the amount of the component (F) is no more than the upper limit of the above-mentioned range, lithography properties are improved.

<<Acid Generator Component; Component (B)>>

In the present embodiment, the resist composition may include an acid generator component (B) (hereafter, referred to as "component (B)") which generates acid upon exposure.

As the component (B), there is no particular limitation, and any of the known acid generators used in conventional chemically amplified resist compositions can be used.

Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators. Among these, it is preferable to use an onium salt acid generator.

As the onium salt acid generator, a compound represented by general formula (b-1) below (hereafter, sometimes referred to as "component (b-1)"), a compound represented by general formula (b-2) below (hereafter, sometimes referred to as "component (b-2)") or a compound represented by general formula (b-3) below (hereafter, sometimes referred to as "component (b-3)") may be used.

[Chemical Formula 46]

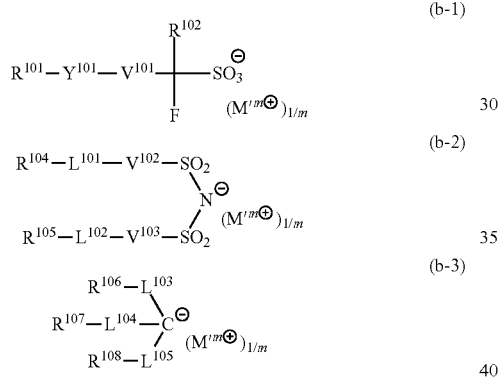

In the formulae, $R^{101}$ and $R^{104}$ to $R^{108}$ each independently represents a cyclic group which may have a substituent, a chain-like alkyl group which may have a substituent or a chain-like alkenyl group which may have a substituent, provided that $R^{104}$ and $R^{105}$ may be mutually bonded to form a ring; two of $R^{106}$ to $R^{108}$ may be mutually bonded to form a ring; $R^{102}$ represents a fluorine atom or a fluorinated alkyl group of 1 to 5 carbon atoms; $Y^{101}$ represents a single bond or a divalent linking group containing an oxygen atom; $V^{101}$ to $V^{103}$ each independently represents a single bond, an alkylene group or a fluorinated alkylene group; $L^{101}$ and $L^{102}$ each independently represents a single bond or an oxygen atom; $L^{103}$ to $L^{105}$ each independently represents a single bond, —CO— or —SO$_2$—; and $M'^{m+}$ represents an organic cation having a valency of m.

{Anion Moiety}

Anion Moiety of Component (b-1)

In the formula (b-1), $R^{101}$ represents a cyclic group which may have a substituent, a chain-like alkyl group which may have a substituent or a chain-like alkenyl group which may have a substituent.

Cyclic Group which May have a Substituent for $R^{101}$

The cyclic group is preferably a cyclic hydrocarbon group, and the cyclic hydrocarbon group may be either an aromatic hydrocarbon group or an aliphatic hydrocarbon group.

As the aromatic hydrocarbon group for $R^{101}$, groups in which one hydrogen atom has been removed from an aromatic hydrocarbon ring described above in relation to the divalent aromatic hydrocarbon group for $Va^1$ in the formula (a1-1) or an aromatic compound containing two or more aromatic ring can be mentioned, and a phenyl group or a naphthyl group is preferable.

As the cyclic aliphatic hydrocarbon group for $R^{101}$, groups in which one hydrogen atom has been removed from a monocycloalkane or a polycycloalkane exemplified above in the explanation of the divalent aliphatic hydrocarbon group for $Va^1$ in the formula (a1-1) can be mentioned, and an adamantyl group or a norbornyl group is preferable.

Further, the cyclic hydrocarbon group for $R^{101}$ may contain a hetero atom like as a heterocycle, and specific examples thereof include lactone-containing cyclic groups represented by the aforementioned general formulas (a2-r-1) to (a2-r-7), —SO$_2$— containing cyclic groups represented by the aforementioned formulas (a5-r-1) to (a5-r-4) and heterocyclic groups (r-hr-1) to (r-hr-16) shown below.

[Chemical Formula 47]

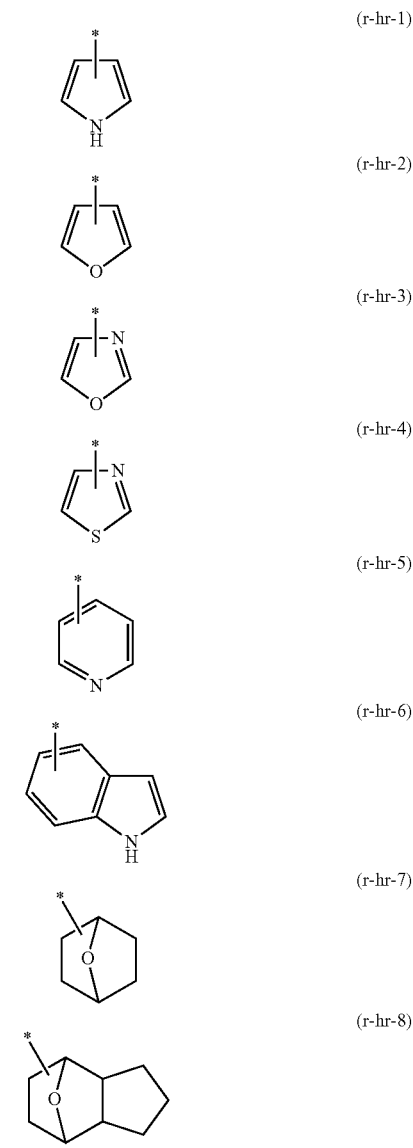

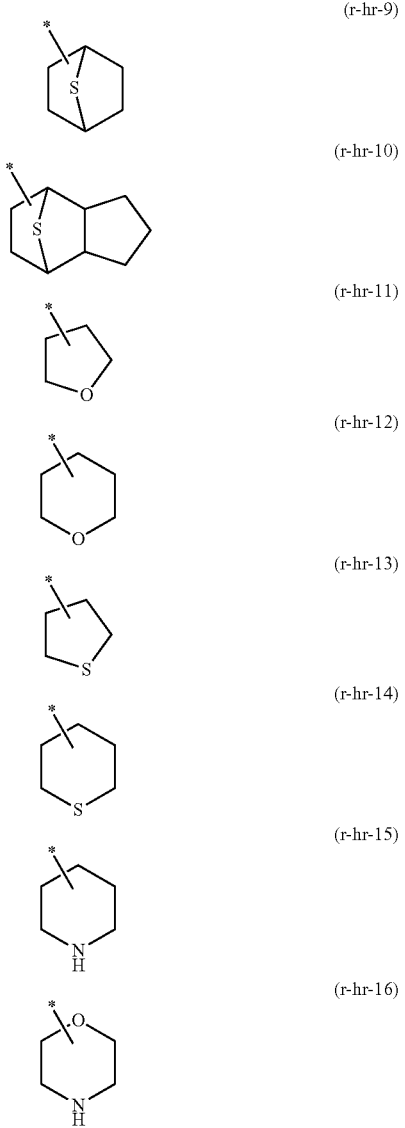

(r-hr-9)
(r-hr-10)
(r-hr-11)
(r-hr-12)
(r-hr-13)
(r-hr-14)
(r-hr-15)
(r-hr-16)

As the substituent for the cyclic hydrocarbon group for $R^{101}$, an alkyl group, an alkoxy group, a halogen atom, a halogenated alkyl group, a hydroxyl group, a carbonyl group, a nitro group or the like can be used.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Example of the aforementioned halogenated alkyl group includes a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

Chain-Like Alkyl Group which May have a Substituent for $R^{101}$

The chain-like alkyl group for $R^{101}$ may be linear or branched.

The linear alkyl group preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched alkyl group preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

Chain-Like Alkenyl Group which May have a Substituent for $R^{101}$

The chain-like alkenyl group for $R^{101}$ may be linear or branched, and preferably has 2 to 10 carbon atoms, more preferably 2 to 5 carbon atoms, still more preferably 2 to 4 carbon atoms, and most preferably 3 carbon atoms. Examples of linear alkenyl groups include a vinyl group, a propenyl group (an allyl group) and a butynyl group. Examples of branched alkenyl groups include a 1-methylpropenyl group and a 2-methylpropenyl group.

Among the above-mentioned examples, as the chain-like alkenyl group, a propenyl group is particularly desirable.

As the substituent for the chain-like alkyl group or alkenyl group for $R^{101}$, an alkoxy group, a halogen atom, a halogenated alkyl group, a hydroxyl group, a carbonyl group, a nitro group, an amino group, a cyclic group for $R^{101}$ or the like can be used.

Among these examples, as $R^{101}$, a cyclic group which may have a substituent is preferable, and a cyclic hydrocarbon group which may have a substituent is more preferable. Specifically, a phenyl group, a naphthyl group, a group in which one or more hydrogen atoms have been removed from a polycycloalkane, a lactone-containing cyclic group represented by any one of the aforementioned formula (a2-r-1) to (a2-r-7), and an —$SO_2$— containing cyclic group represented by any one of the aforementioned formula (a5-r-1) to (a5-r-4).

In formula (b-1), $Y^{101}$ represents a single bond or a divalent linking group containing an oxygen atom.

In the case where $Y^{101}$ is a divalent linking group containing an oxygen atom, $Y^{101}$ may contain an atom other than an oxygen atom. Examples of atoms other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an oxycarbonyl group (—O—C(=O)—), an amido bond (—C(=O)—NH—), a carbonyl group (—C(=O)—) and a carbonate bond (—O—C(=O)—O—); and combinations of the aforementioned non-hydrocarbon, hetero atom-containing linking groups with an alkylene group. Furthermore, the combinations may have a sulfonyl group (—$SO_2$—) bonded thereto. As the combination, the linking group represented by formulas (y-a1-1) to (y-a1-7) shown below can be mentioned.

[Chemical Formula 48]

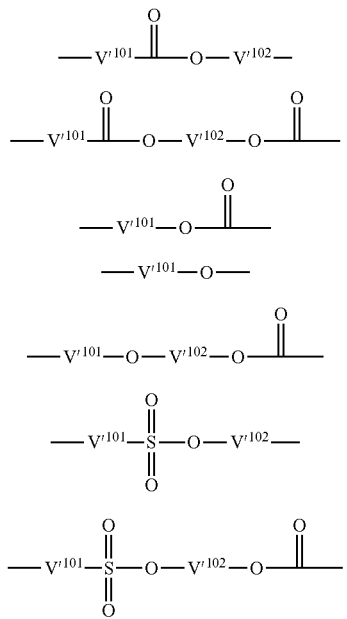

In the formulae, $V'^{101}$ represents a single bond or an alkylene group of 1 to 5 carbon atoms; $V'^{102}$ represents a divalent saturated hydrocarbon group of 1 to 30 carbon atoms.

The divalent saturated hydrocarbon group for $V'^{102}$ is preferably an alkylene group of 1 to 30 carbon atoms.

The alkylene group for $V'^{101}$ and $V'^{102}$ may be a linear alkylene group or a branched alkylene group, and a linear alkylene group is preferable.

Specific examples of the alkylene group for $V'^{101}$ and $V'^{102}$ include a methylene group [—$CH_2$—]; an alkylmethylene group, such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$— and —$C(CH_2CH_3)_2$—; an ethylene group [—$CH_2CH_2$—]; an alkylethylene group, such as —$CH(CH_3)CH_2$—, —$CH(CH_3)CH(CH_3)$—, —$C(CH_3)_2CH_2$— and —$CH(CH_2CH_3)CH_2$—; a trimethylene group (n-propylene group) [—$CH_2CH_2CH_2$—]; an alkyltrimethylene group, such as —$CH(CH_3)CH_2CH_2$— and —$CH_2CH(CH_3)CH_2$—; a tetramethylene group [—$CH_2CH_2CH_2CH_2$—]; an alkyltetramethylene group, such as —$CH(CH_3)CH_2CH_2CH_2$—, —$CH_2CH(CH_3)CH_2CH_2$—; and a pentamethylene group [—$CH_2CH_2CH_2CH_2CH_2$—].

Further, part of methylene group within the alkylene group for $V'^{101}$ and $V'^{102}$ may be substituted with a divalent aliphatic cyclic group of 5 to 10 carbon atoms. The aliphatic cyclic group is preferably a divalent group in which one hydrogen atom has been removed from the cyclic aliphatic hydrocarbon group for $Ra'^3$ in the aforementioned formula (a1-r-1), and a cyclohexylene group, 1,5-adamantylene group or 2,6-adamantylene group is preferable.

$Y^{101}$ is preferably a divalent linking group containing an ether bond or an ester bond, and groups represented by the aforementioned formulas (y-a1-1) to (y-a1-5) are preferable.

In formula (b-1), $V^{101}$ represents a single bond, an alkylene group or a fluorinated alkylene group. The alkylene group and the fluorinated alkylene group for $V^{101}$ preferably has 1 to 4 carbon atoms. Examples of the fluorinated alkylene group for $V^{101}$ include a group in which part or all of the hydrogen atoms within the alkylene group for $V^{101}$ have been substituted with fluorine. Among these examples, as $V^{101}$, a single bond or a fluorinated alkylene group of 1 to 4 carbon atoms is preferable.

In formula (b-1), $R^{102}$ represents a fluorine atom or a fluorinated alkyl group of 1 to 5 carbon atoms. $R^{102}$ is preferably a fluorine atom or a perfluoroalkyl group of 1 to 5 carbon atoms, and more preferably a fluorine atom.

As a specific example of the anion moiety for the component (b-1), in the case where $Y^{101}$ a single bond, a fluorinated alkylsulfonate anion such as a trifluoromethanesulfonate anion or a perfluorobutanesulfonate anion can be mentioned; and in the case where $Y^{101}$ represents a divalent linking group containing an oxygen atom, anions represented by formulae (an-1) to (an-3) shown below can be mentioned.

[Chemical Formula 49]

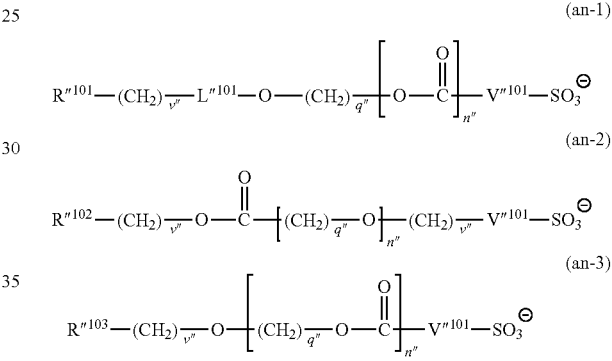

In the formulae, $R''^{101}$ represents an aliphatic cyclic group which may have a substituent, a group represented by any one of the aforementioned formulae (r-hr-1) to (r-hr-6) or a chain-like alkyl group which may have a substituent; $R''^{102}$ represents an aliphatic cyclic group which may have a substituent, a lactone-containing cyclic group represented by any one of the aforementioned general formulae (a2-r-1) to (a2-r-7) or an —$SO_2$— containing cyclic group represented by any one of the aforementioned general formulae (a5-r-1) to (a5-r-4); $R''^{103}$ represents an aromatic cyclic group which may have a substituent, an aliphatic cyclic group which may have a substituent or a chain-like alkenyl group which may have a substituent; $V''^{101}$ represents a fluorinated alkylene group; $L''^{101}$ represents —C(=O)— or —$SO_2$—; $v''$ represents an integer of 0 to 3; $q''$ represents an integer of 1 to 20; and $n''$ represents 0 or 1.

As the aliphatic cyclic group for $R''^{101}$, $R''^{102}$ and $R''^{103}$ which may have a substituent, the same groups as the cyclic aliphatic hydrocarbon group for $R^{104}$ described above are preferable. As the substituent, the same groups as those described above for substituting the cyclic aliphatic hydrocarbon group for $R^{104}$ can be mentioned.

As the aromatic cyclic group for $R''^{103}$ which may have a substituent, the same groups as the aromatic hydrocarbon group for the cyclic hydrocarbon group represented by $R^{101}$ described above are preferable. The substituent is the same as defined for the substituent for the aromatic hydrocarbon group represented by $R^{101}$.

As the chain-like alkyl group for $R'''^{101}$ which may have a substituent, the same groups as those described above for $R^{101}$ are preferable. As the chain-like alkenyl group for $R'''^{103}$ which may have a substituent, the same groups as those described above for $R^{101}$ are preferable. $V''^{101}$ is preferably a fluorinated alkylene group of 1 to 3 carbon atoms, and most preferably —$CF_2$—, —$CF_2CF_2$—, —$CHFCF_2$—, —$CF(CF_3)CF_2$— or —$CH(CF_3)CF_2$—.

Anion Moiety of Component (b-2)

In formula (b-2), $R^{104}$ and $R^{105}$ each independently represents a cyclic group which may have a substituent, a chain-like alkyl group which may have a substituent or a chain-like alkenyl group which may have a substituent, and is the same as defined for $R^{101}$ in formula (b-1). $R^{104}$ and $R^{105}$ may be mutually bonded to form a ring.

As $R^{104}$ and $R^{105}$, a chain-like alkyl group which may have a substituent is preferable, and a linear or branched alkyl group or a linear or branched fluorinated alkyl group is more preferable.

The chain-like alkyl group preferably has 1 to 10 carbon atoms, more preferably 1 to 7 carbon atoms, and still more preferably 1 to 3 carbon atoms. The smaller the number of carbon atoms of the chain-like alkyl group for $R^{104}$ and $R^{105}$, the more the solubility in a resist solvent is improved. Further, in the chain-like alkyl group for $R^{104}$ and $R^{105}$, it is preferable that the number of hydrogen atoms substituted with fluorine atoms is as large as possible because the acid strength increases and the transparency to high energy radiation of 200 nm or less or electron beam is improved. The fluorination ratio of the chain-like alkyl group is preferably from 70 to 100%, more preferably from 90 to 100%, and it is particularly desirable that the chain-like alkyl group be a perfluoroalkyl group in which all hydrogen atoms are substituted with fluorine atoms.

In formula (b-2), $V^{102}$ and $V^{103}$ each independently represents a single bond, an alkylene group or a fluorinated alkylene group, and is the same as defined for $V^{101}$ in formula (b-1).

In formula (b-2), $L^{101}$ and $L^{102}$ each independently represents a single bond or an oxygen atom.

Anion Moiety of Component (b-3)

In formula (b-3), $R^{106}$ to $R^{108}$ each independently represents a cyclic group which may have a substituent, a chain-like alkyl group which may have a substituent or a chain-like alkenyl group which may have a substituent, and is the same as defined for $R^{101}$ in formula (b-1).

$L^{103}$ to $L^{105}$ each independently represents a single bond, —CO— or —$SO_2$—.

{Cation Moiety}

In formulae (b-1), (b-2) and (b-3), $M'^{m+}$ represents an organic cation having a valency of m, preferably a sulfonium cation or an iodonium cation, and most preferably a cation represented by any one of formulae (ca-1) to (ca-4) shown below.

[Chemical Formula 50]

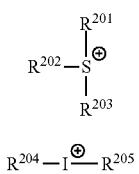

(ca-1)

(ca-2)

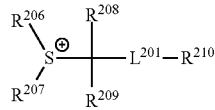

(ca-3)

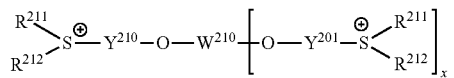

(ca-4)

In the formulae, $R^{201}$ to $R^{207}$, $R^{211}$ and $R^{212}$ each independently represents an aryl group, an alkyl group or an alkenyl group, provided that two of $R^{201}$ to $R^{203}$, $R^{206}$ and $R^{207}$, or $R^{211}$ and $R^{212}$ may be mutually bonded to form a ring with the sulfur atom; $R^{208}$ and $R^{209}$ each independently represents a hydrogen atom or an alkyl group of 1 to 5 carbon atoms; $R^{210}$ represents an aryl group which may have a substituent, an alkyl group which may have a substituent, an alkenyl group which may have a substituent or an —$SO_2$— containing cyclic group which may have a substituent; $L^{201}$ represents —C(=O)— or —C(=O)—O—; $Y^{201}$ each independently represents an arylene group, an alkylene group or an alkenylene group; x represents 1 or 2; and $W^{201}$ represents a linking group having a valency of (x+1).

As the aryl group for $R^{201}$ to $R^{207}$, $R^{211}$ and $R^{212}$, an unsubstituted aryl group of 6 to 20 carbon atoms can be mentioned, and a phenyl group or a naphthyl group is preferable.

The alkyl group for $R^{201}$ to $R^{207}$, $R^{211}$ and $R^{212}$ is preferably a chain-like or cyclic alkyl group having 1 to 30 carbon atoms.

The alkenyl group for $R^{201}$ to $R^{207}$, $R^{211}$ and $R^{212}$ preferably has 2 to 10 carbon atoms.

Specific examples of the substituent which $R^{201}$ to $R^{207}$ and $R^{210}$ to $R^{212}$ may have include an alkyl group, a halogen atom, a halogenated alkyl group, a carbonyl group, a cyano group, an amino group, an aryl group, an arylthio group and groups represented by formulae (ca-r-1) to (ca-r-7) shown below.

The aryl group within the arylthio group as the substituent is the same as defined for $R^{101}$, and specific examples include a phenylthio group and a biphenylthio group.

[Chemical Formula 51]

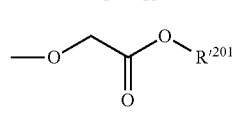

[ca-r-1]

[ca-r-2]

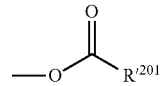

[ca-r-3]

[ca-r-4]

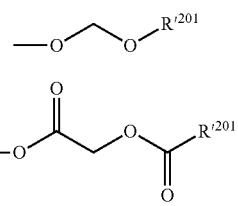

[ca-r-5]

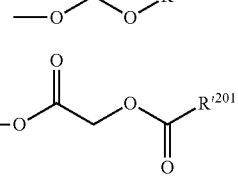

-continued

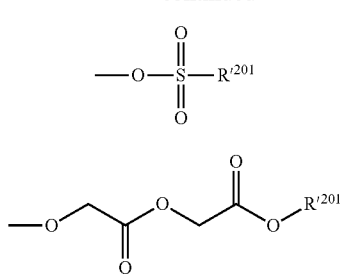

[ca-r-6]

[ca-r-7]

In the formulae, $R'^{201}$ each independently represents a hydrogen atom, a cyclic group which may have a substituent, a chain-like alkyl group which may have a substituent or a chain-like alkenyl group which may have a substituent.

As the cyclic group which may have a substituent, the chain-like alkyl group which may have a substituent and the chain-like alkenyl group which may have a substituent for $R'^{201}$, the same groups as those described above for $R^{101}$ can be mentioned. As the cyclic group which may have a substituent and chain-like alkyl group which may have a substituent, the same groups as those described above for the acid dissociable group represented by the aforementioned formula (a1-r-2) can be also mentioned.

When $R^{201}$ to $R^{203}$, $R^{206}$, $R^{207}$, $R^{211}$ and $R^{212}$ are mutually bonded to form a ring with the sulfur atom, these groups may be mutually bonded via a hetero atom such as a sulfur atom, an oxygen atom or a nitrogen atom, or a functional group such as a carbonyl group, —SO—, —SO$_2$—, —SO$_3$—, —COO—, —CONH— or —N(R$_N$)— (wherein R$_N$ represents an alkyl group of 1 to 5 carbon atoms). The ring containing the sulfur atom in the skeleton thereof is preferably a 3 to 10-membered ring, and most preferably a 5 to 7-membered ring. Specific examples of the ring formed include a thiophene ring, a thiazole ring, a benzothiophene ring, a thianthrene ring, a benzothiophene ring, a dibenzothiophene ring, a 9H-thioxanthene ring, a thioxanthone ring, a phenoxathiin ring, a tetrahydrothiophenium ring, and a tetrahydrothiopyranium ring.

$R^{208}$ and $R^{209}$ each independently represents a hydrogen atom or an alkyl group of 1 to 5 carbon atoms, preferably a hydrogen atom or an alkyl group of 1 to 3 carbon atoms, and when $R^{208}$ and $R^{209}$ each represents an alkyl group, $R^{208}$ and $R^{209}$ may be mutually bonded to form a ring.

$R^{210}$ represents an aryl group which may have a substituent, an alkyl group which may have a substituent, an alkenyl group which may have a substituent, or an —SO$_2$— containing cyclic group which may have a substituent.

Examples of the aryl group for $R^{210}$ include an unsubstituted aryl group of 6 to 20 carbon atoms, and a phenyl group or a naphthyl group is preferable.

As the alkyl group for $R^{210}$, a chain-like or cyclic alkyl group having 1 to 30 carbon atoms is preferable.

The alkenyl group for $R^{210}$ preferably has 2 to 10 carbon atoms.

As the —SO$_2$— containing cyclic group for $R^{210}$ which may have a substituent, the same "—SO$_2$— containing cyclic groups" as those described above may be mentioned, and a group represented by the aforementioned general formula (a5-r-1) is preferable.

Each $Y^{201}$ independently represents an arylene group, an alkylene group or an alkenylene group.

Examples of the arylene group for $Y^{201}$ include groups in which one hydrogen atom has been removed from an aryl group given as an example of the aromatic hydrocarbon group for $R^{104}$ in the aforementioned formula (b-1).

The alkylene group and the alkenylene group for $Y^{201}$ is the same as defined for the aliphatic hydrocarbon group as the divalent linking group represented by Va$^1$ in the aforementioned general formula (a1-1).

In the formula (ca-4), x represents 1 or 2.

$W^{201}$ represents a linking group having a valency of (x+1), i.e., a divalent or trivalent linking group.

As the divalent linking group for $W^{201}$, a divalent hydrocarbon group which may have a substituent is preferable, and as examples thereof, the same hydrocarbon groups as those described above for Ya$^{21}$ in the general formula (a2-1) can be mentioned. The divalent linking group for $W^{201}$ may be linear, branched or cyclic, and cyclic is more preferable. Among these, an arylene group having two carbonyl groups, each bonded to the terminal thereof is preferable. Examples of the arylene group include a phenylene group and a naphthylene group, and a phenylene group is particularly desirable.

As the trivalent linking group for $W^{201}$, a group in which one hydrogen atom has been removed from the aforementioned divalent linking group for $W^{201}$ and a group in which the divalent linking group has been bonded to another divalent linking group can be mentioned. The trivalent linking group for $W^{201}$ is preferably a group in which 2 carbonyl groups are bonded to an arylene group.

Specific examples of preferable cations represented by formula (ca-1) include cations represented by formulae (ca-1-1) to (ca-1-63) shown below.

[Chemical Formula 52]

(ca-1-1)

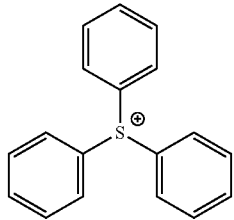

(ca-1-2)

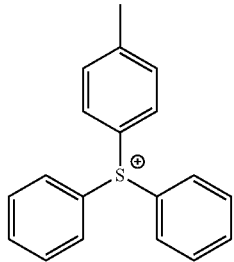

(ca-1-3)

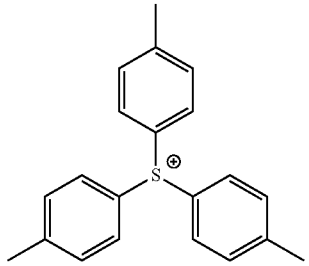

(ca-1-4)
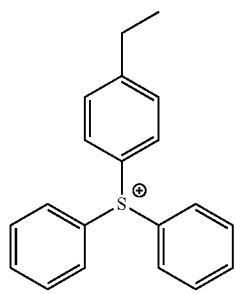
(ca-1-5)
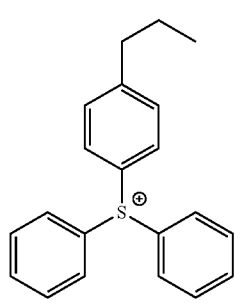
(ca-1-6)
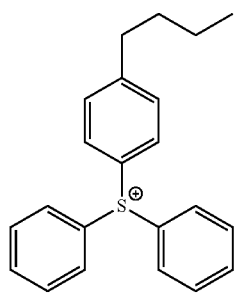
(ca-1-7)
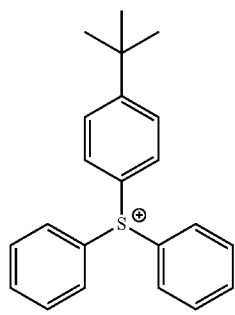
(ca-1-8)
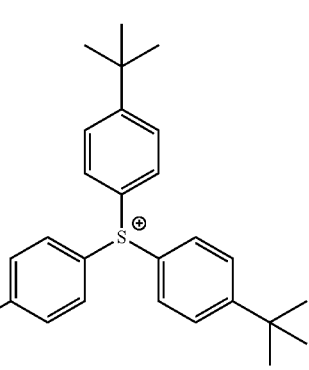
(ca-1-9)
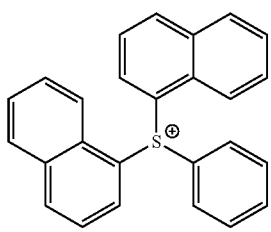
(ca-1-10)
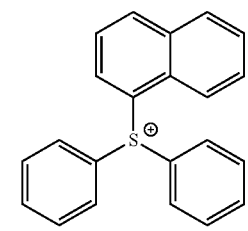
(ca-1-11)
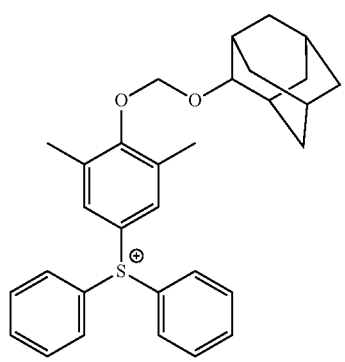
(ca-1-12)
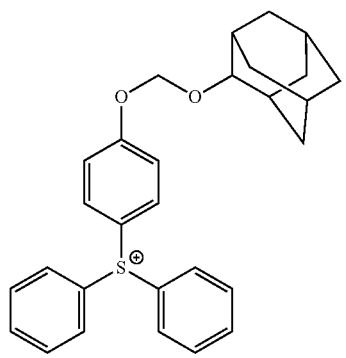
(ca-1-13)
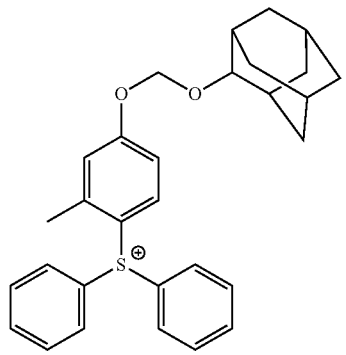

(ca-1-14)
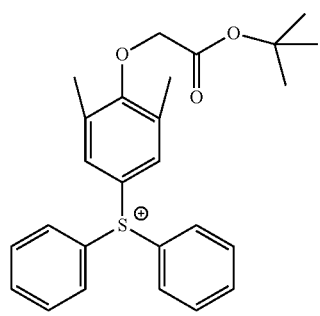
(ca-1-15)
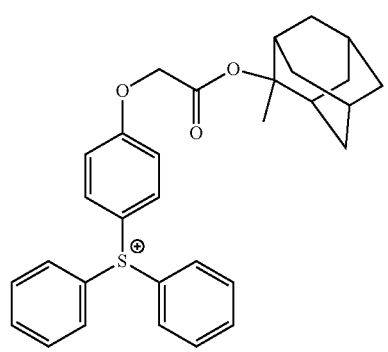
(ca-1-16)
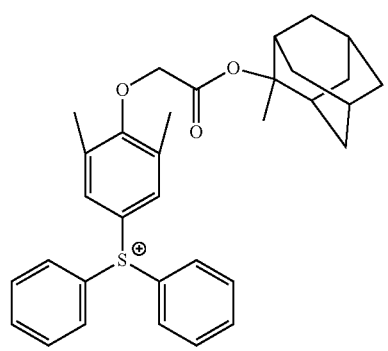
[Chemical Formula 53]
(ca-1-17)
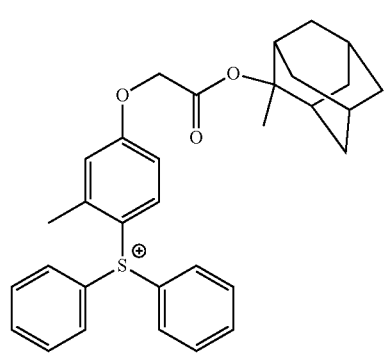
(ca-1-18)
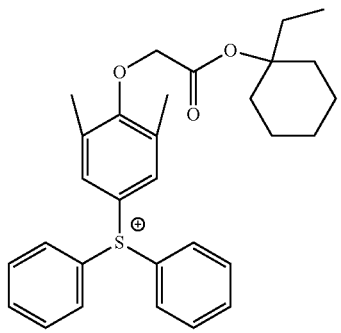
(ca-1-19)
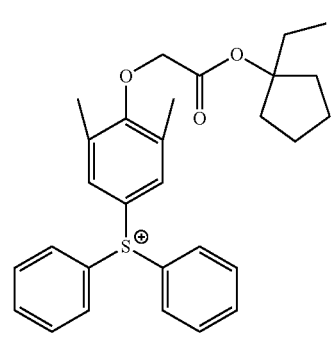
(ca-1-20)
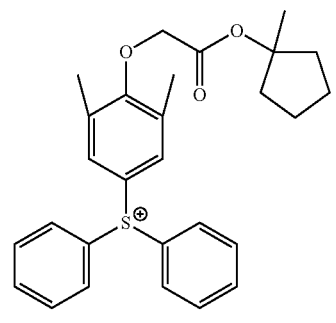
(ca-1-21)
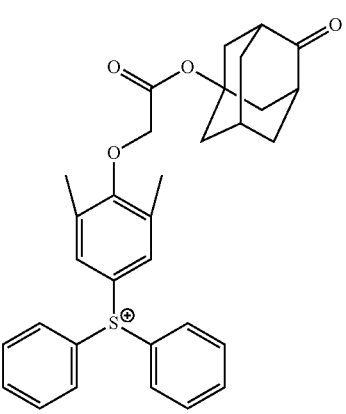

(ca-1-22)
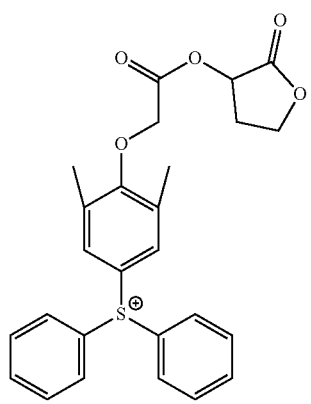
(ca-1-26)
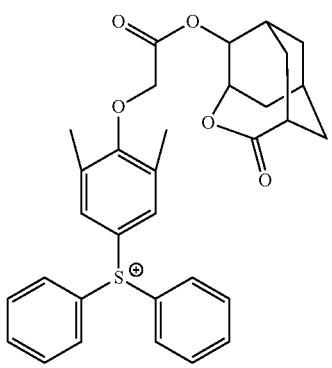
(ca-1-23)
(ca-1-27)
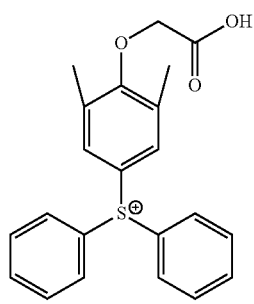
(ca-1-24)
(ca-1-28)
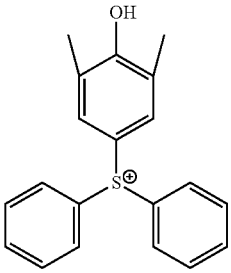
(ca-1-29)
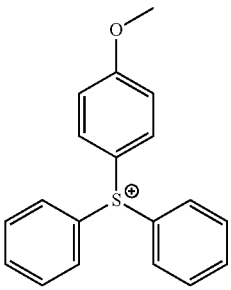
(ca-1-25)
(ca-1-30)
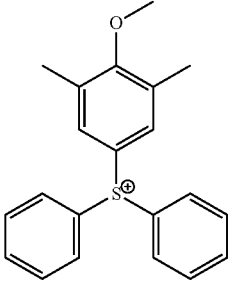

(ca-1-31)
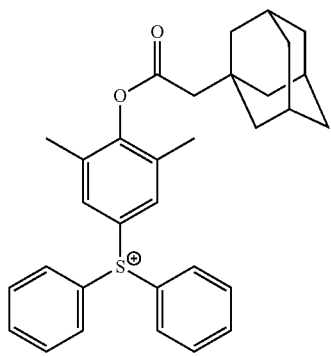
(ca-1-35)
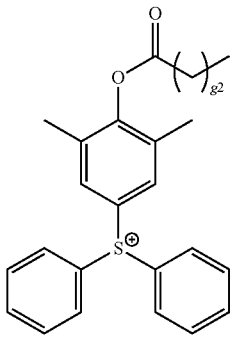
(ca-1-32)
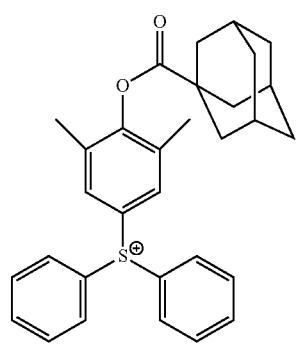
(ca-1-36)
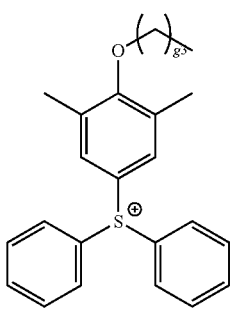
(ca-1-33)
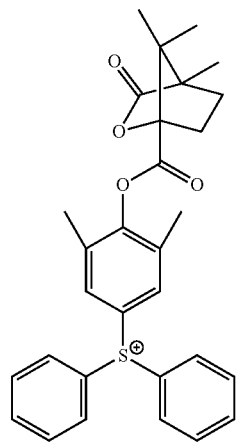
(ca-1-37)
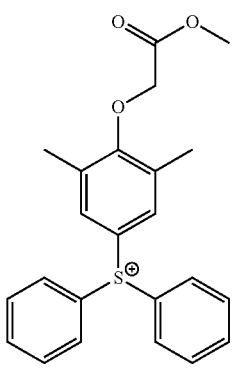
[Chemical Formula 54]
(ca-1-34)
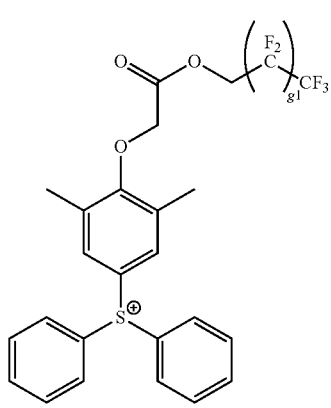
(ca-1-38)

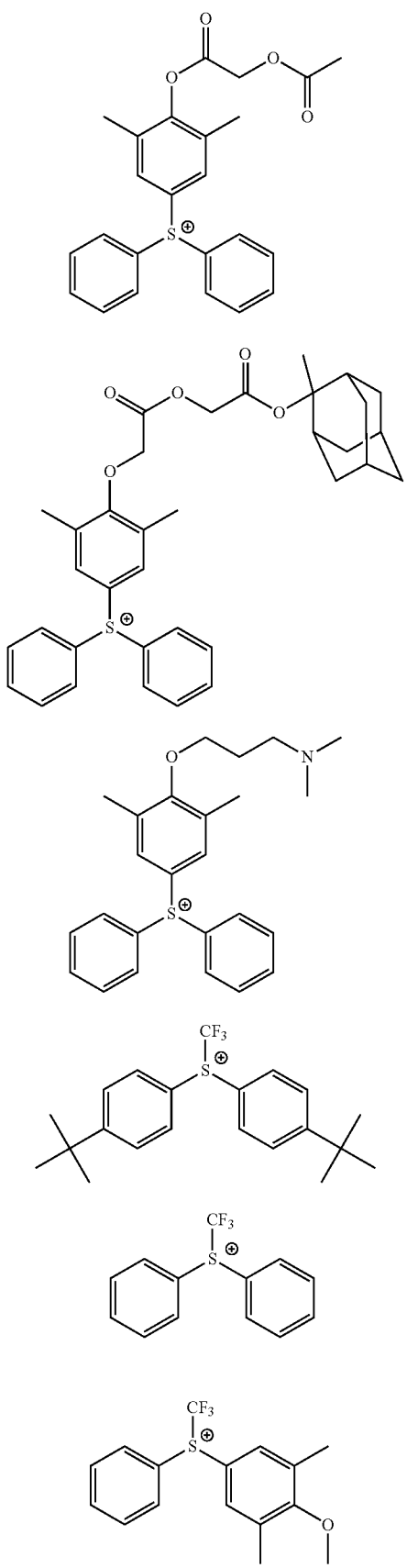
(ca-1-39)
(ca-1-40)
(ca-1-41)
(ca-1-42)
(ca-1-43)
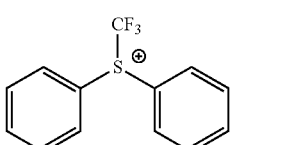
(ca-1-44)
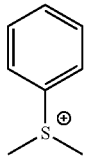
(ca-1-45)
(ca-1-46)
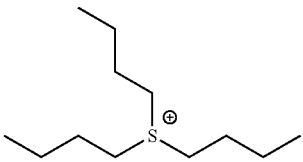
(ca-1-47)
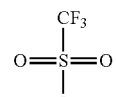
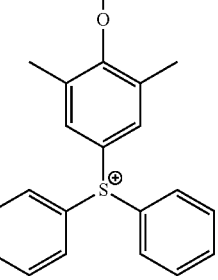
(ca-1-48)
In the formulae, g1, g2 and g3 represent recurring numbers, wherein g1 is an integer of 1 to 5, g2 is an integer of 0 to 20, and g3 is an integer of 0 to 20.
[Chemical Formula 55]
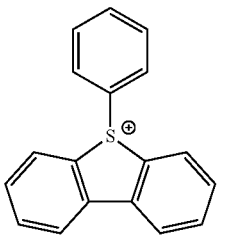
(ca-1-49)
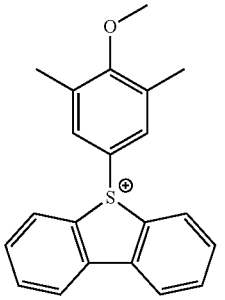
(ca-1-50)

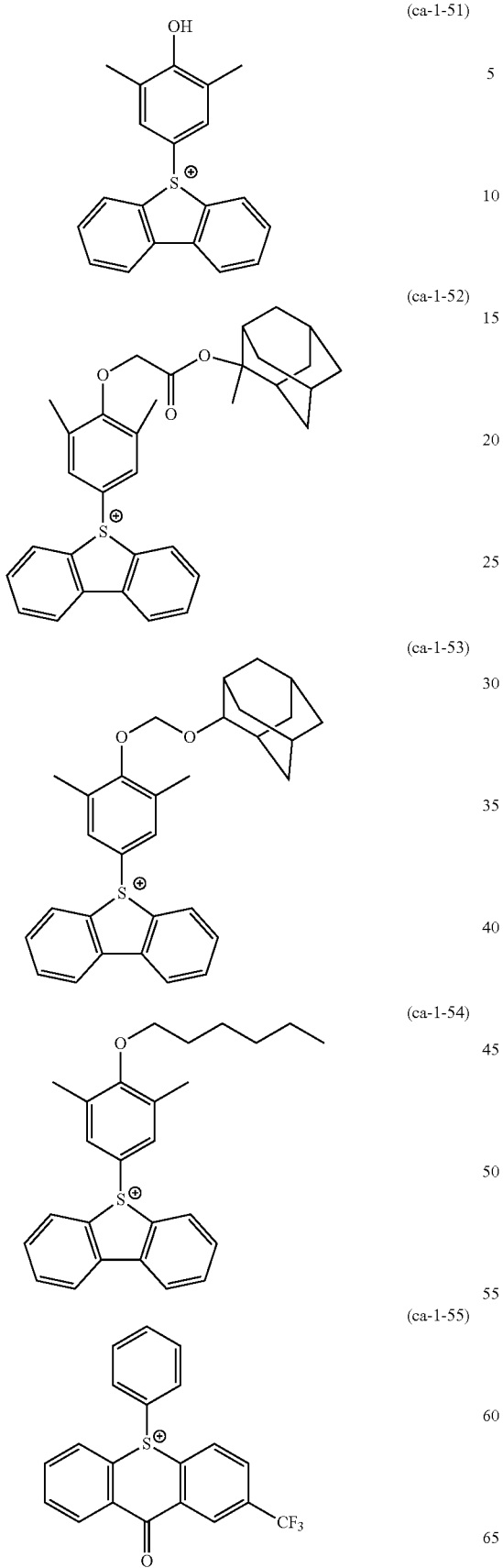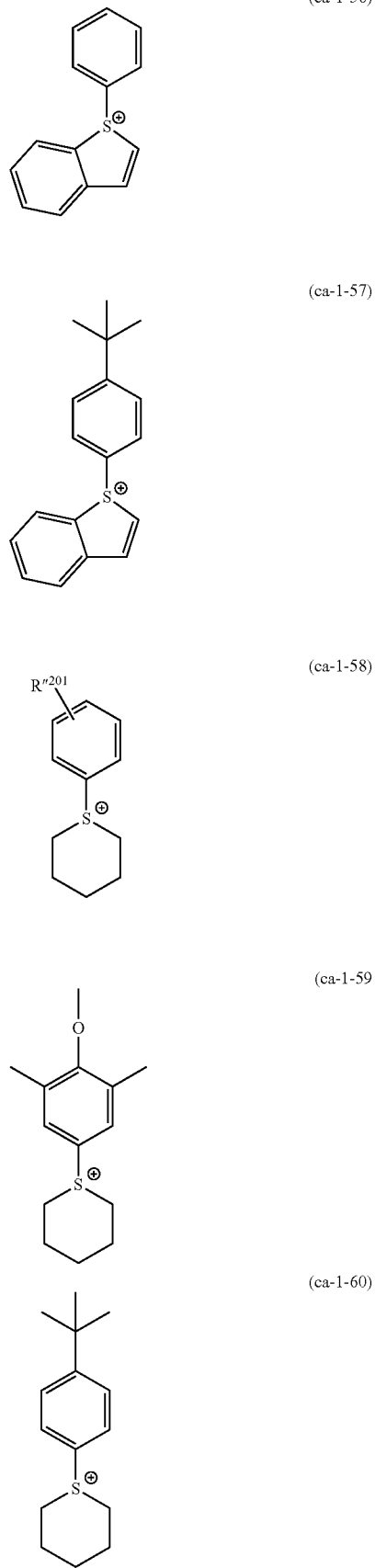

-continued (ca-1-61)

(ca-1-62)

(ca-1-63)

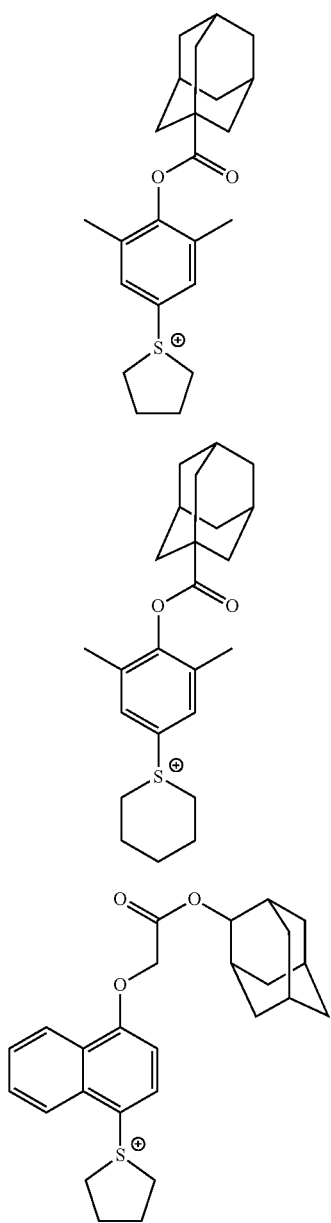

[Chemical Formula 56]

(ca-3-1)

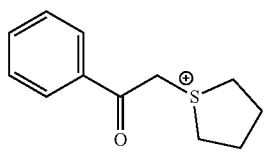

-continued (ca-3-2)

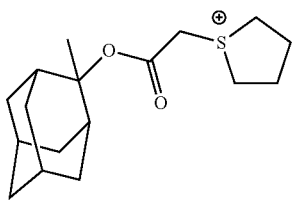

(ca-3-3)

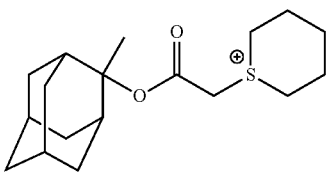

(ca-3-4)

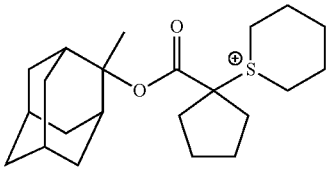

(ca-3-5)

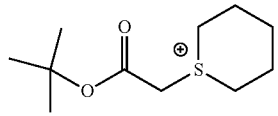

(ca-3-6)

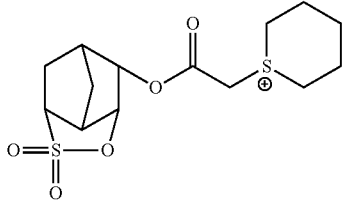

In the formulae, $R''^{201}$ represents a hydrogen atom or a substituent, and as the substituent, the same groups as those described above for substituting $R^{201}$ to $R^{207}$ and $R^{210}$ to $R^{212}$ can be mentioned.

Specific examples of preferable cations represented by formula (ca-3) include cations represented by formulae (ca-3-1) to (ca-3-6) shown below.

Specific examples of preferable cations represented by formula (ca-4) include cations represented by formulae (ca-4-1) and (ca-4-2) shown below.

[Chemical Formula 57]

(ca-4-1)

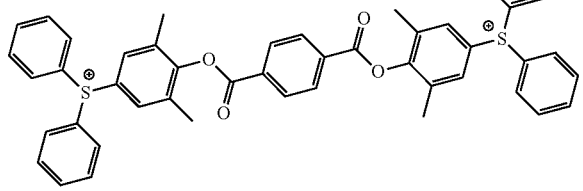

(ca-4-2)

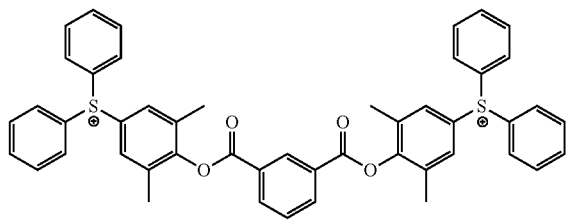

As the component (B), one type of these acid generators may be used alone, or two or more types may be used in combination.

In the present embodiment, when the resist composition contains the component (B), the amount of the component (B) relative to 100 parts by weight of the component (A) is preferably within a range from 0.5 to 60 parts by weight, more preferably from 1 to 50 parts by weight, and still more preferably from 1 to 40 parts by weight.

When the amount of the component (B) is within the above-mentioned range, formation of a resist pattern can be satisfactorily performed. Further, by virtue of the above-mentioned range, when each of the components are dissolved in an organic solvent, a uniform solution can be obtained and the storage stability becomes satisfactory.

<<Other Components>>

In the present embodiment, the resist composition may further contain, in addition to the component (A), or in addition to the component (A) and (B), any other optional components.

Examples of the other components include the component (D), the component (E) and the component (S) described below.

Component (D):

In the present embodiment, the resist composition may further contain an acid diffusion control agent (hereafter, referred to as "component (D)").

The component (D) functions as an acid diffusion control agent, i.e., a quencher which traps the acid generated from the component (B) and the like upon exposure.

In the present embodiment, the component (D) may be a photodecomposable base (D1) (hereafter, referred to as "component (D1)") which is decomposed upon exposure and then loses the ability of controlling of acid diffusion, or a nitrogen-containing organic compound (D2) (hereafter, referred to as "component (D2)") which does not fall under the definition of component (D1).

Component (D1)

When a resist pattern is formed using a resist composition containing the component (D1), the contrast between exposed portions and unexposed portions is improved.

The component (D1) is not particularly limited, as long as it is decomposed upon exposure and then loses the ability of controlling of acid diffusion. As the component (D1), at least one compound selected from the group consisting of a compound represented by general formula (d1-1) shown below (hereafter, referred to as "component (d1-1)"), a compound represented by general formula (d1-2) shown below (hereafter, referred to as "component (d1-2)") and a compound represented by general formula (d1-3) shown below (hereafter, referred to as "component (d1-3)") is preferably used.

At exposed portions, the components (d1-1) to (d1-3) are decomposed and then lose the ability of controlling of acid diffusion (i.e., basicity), and therefore the components (d1-1) to (d1-3) cannot function as a quencher, whereas at unexposed portions, the components (d1-1) to (d1-3) functions as a quencher.

[Chemical Formula 58]

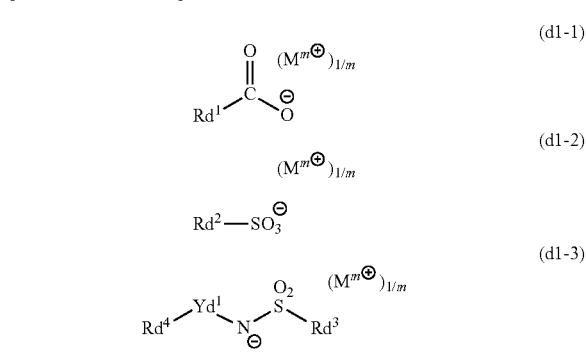

In the formulae, $Rd^1$ to $Rd^4$ represent a cyclic group which may have a substituent, a chain-like alkyl group which may have a substituent or a chain-like alkenyl group which may have a substituent, provided that, the carbon atom adjacent to the sulfur atom within the $Rd^2$ in the formula (d1-2) has no fluorine atom bonded thereto; $Yd^1$ represents a single bond or a divalent linking group; and $M^{m+}$ each independently represents a cation having a valency of m.

{Component (d1-1)}

Anion Moiety

In formula (d1-1), $Rd^1$ represents a cyclic group which may have a substituent, a chain-like alkyl group which may have a substituent or a chain-like alkenyl group which may have a substituent, and is the same groups as those defined above for $R^{101}$.

Among these, as the group for $Rd^1$, an aromatic hydrocarbon group which may have a substituent, an aliphatic cyclic group which may have a substituent and a chain-like hydrocarbon group which may have a substituent are preferable. As the substituents which these groups may have, a fluorine atom or a fluorinated alkyl group is preferable.

The aromatic hydrocarbon group is preferably a phenyl group or a naphthyl group.

Examples of the aliphatic cyclic group include groups in which one or more hydrogen atoms have been removed from a polycycloalkane such as adamantane, norbornane, isobornane, tricyclodecane or tetracyclododecane.

As the chain-like hydrocarbon group, a chain-like alkyl group is preferable. The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group.

In the case where the chain-like alkyl group is a fluorinated alkyl group having a fluorine atom or a fluorinated alkyl group, the fluorinated alkyl group preferably has 1 to 11 carbon atoms, more preferably 1 to 8 carbon atoms, and still more preferably 1 to 4 carbon atoms. The fluorinated alkyl group may contain an atom other than fluorine.

Examples of the atom other than fluorine include an oxygen atom, a carbon atom, a hydrogen atom, a sulfur atom and a nitrogen atom.

As $Rd^1$, a fluorinated alkyl group in which part or all of the hydrogen atoms constituting a linear alkyl group have been substituted with fluorine atom(s) is preferable, and a fluorinated alkyl group in which all of the hydrogen atoms constituting a linear alkyl group have been substituted with fluorine atoms (i.e., a linear perfluoroalkyl group) is more preferable.

Specific examples of preferable anion moieties for the component (d1-1) are shown below.

[Chemical Formula 59]

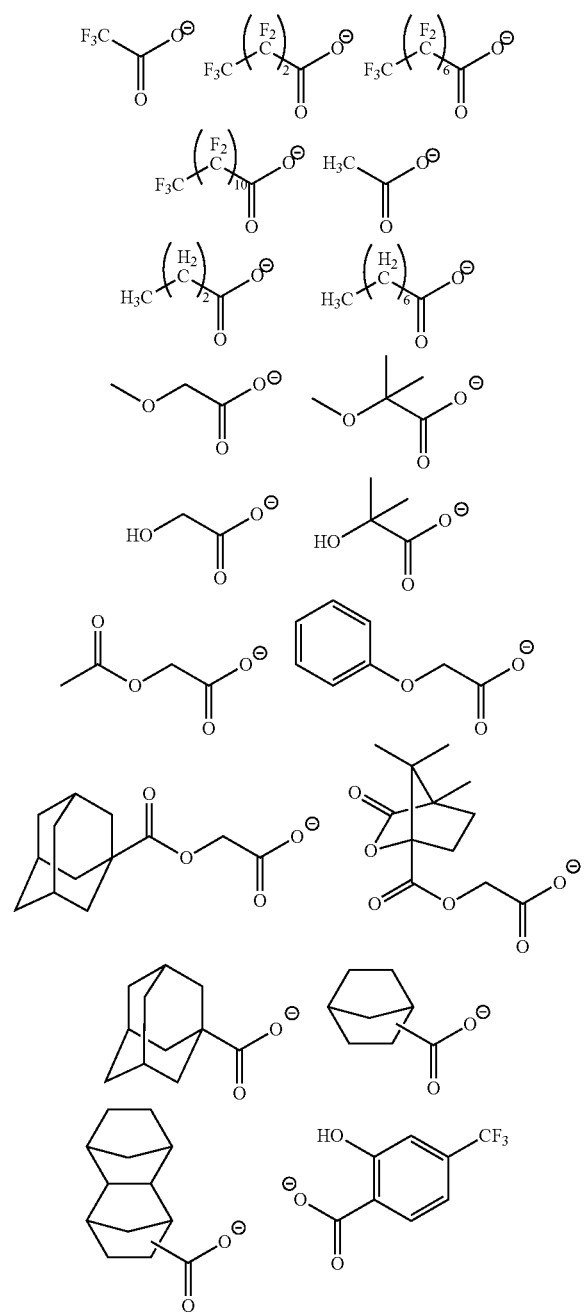
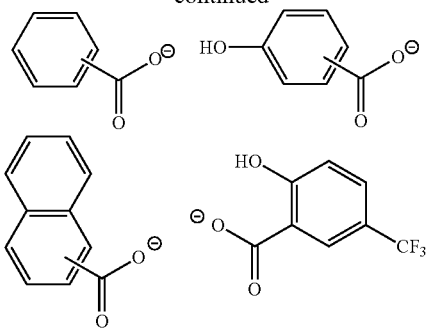

Cation Moiety

In formula (d1-1), $M^{m+}$ represents an organic cation having a valency of m.

The organic cation for $M^{m+}$ is not particularly limited, and examples thereof include the same cation moieties as those represented by the aforementioned formulas (ca-1) to (ca-4), and cation moieties represented by the aforementioned formulas (ca-1-1) to (ca-1-63) are preferable.

As the component (d1-1), one type of compound may be used, or two or more types of compounds may be used in combination.

{Component (d1-2)}

Anion Moiety

In formula (d1-2), $Rd^2$ represents a cyclic group which may have a substituent, a chain-like alkyl group which may have a substituent or a chain-like alkenyl group which may have a substituent, and is the same groups as those defined above for $R^{101}$, provided that, the carbon atom adjacent to the sulfur atom within $Rd^2$ group has no fluorine atom bonded thereto (i.e., the carbon atom adjacent to the sulfur atom within $Rd^2$ group does not substituted with a fluorine atom). As a result, the anion of the component (d1-2) becomes an appropriately weak acid anion, thereby improving the quenching ability of the component (D).

As $Rd^2$, an aliphatic cyclic group which may have a substituent is preferable, and a group in which one or more hydrogen atoms have been removed from adamantane, norbornane, isobornane, tricyclodecane, tetracyclododecane or camphor (which may have a substituent) is more preferable.

The hydrocarbon group for $Rd^2$ may have a substituent. As the substituent, the same groups as those described above for substituting the hydrocarbon group (e.g., aromatic hydrocarbon group, aliphatic hydrocarbon group) for $Rd^1$ in the formula (d1-1) can be mentioned.

Specific examples of preferable anion moieties for the component (d1-2) are shown below.

[Chemical Formula 60]

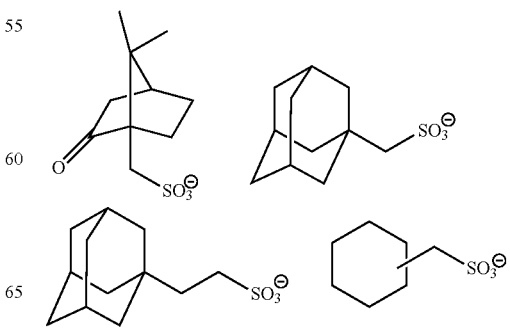

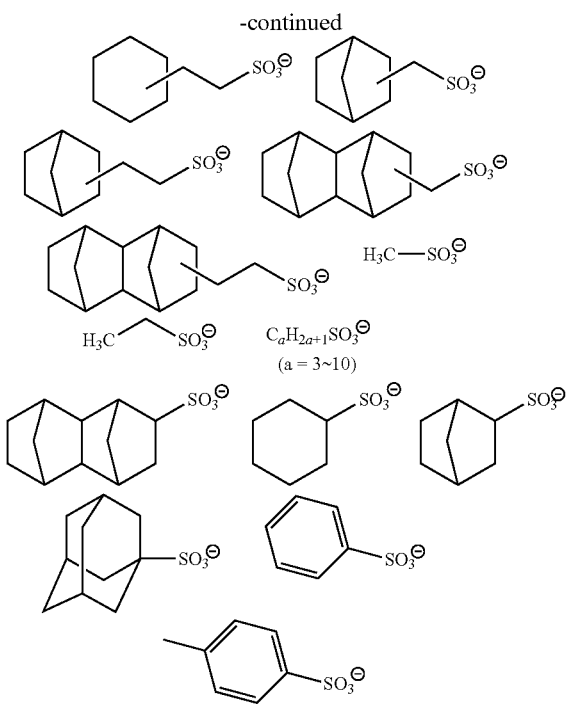

Cation Moiety

In formula (d1-2), $M^{m+}$ is an organic cation having a valency of m, and is the same as defined for $M^{m+}$ in the aforementioned formula (d1-1).

As the component (d1-2), one type of compound may be used, or two or more types of compounds may be used in combination.

{Component (d1-3)}

Anion Moiety

In formula (d1-3), $Rd^3$ represents a cyclic group which may have a substituent, a chain-like alkyl group which may have a substituent or a chain-like alkenyl group which may have a substituent, and is the same groups as those defined above for $R^{101}$, and a cyclic group containing a fluorine atom, a chain-like alkyl group or a chain-like alkenyl group is preferable. Among these, a fluorinated alkyl group is preferable, and more preferably the same fluorinated alkyl groups as those described above for $Rd^1$.

In formula (d1-3), $Rd^4$ represents a cyclic group which may have a substituent, a chain-like alkyl group which may have a substituent or a chain-like alkenyl group which may have a substituent, and is the same groups as those defined above for $R^{101}$.

Among these, an alkyl group which may have substituent, an alkoxy group which may have substituent, an alkenyl group which may have substituent or a cyclic group which may have substituent is preferable.

The alkyl group for $Rd^4$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for $Rd^4$ may be substituted with a hydroxy group, a cyano group or the like.

The alkoxy group for $Rd^4$ is preferably an alkoxy group of 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are preferable.

As the alkenyl group for $Rd^4$, the same groups as those described above for $R^{101}$ can be mentioned, and a vinyl group, a propenyl group (an allyl group), a 1-methylpropenyl group and a 2-methylpropenyl group are preferable. These groups may have an alkyl group of 1 to 5 carbon atoms or a halogenated alkyl group of 1 to 5 carbon atoms as a substituent.

As the cyclic group for $Rd^4$, the same groups as those described above for $R^{101}$ can be mentioned. Among these, as the cyclic group, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When $Rd^4$ is an alicyclic group, the resist composition can be satisfactorily dissolved in an organic solvent, thereby improving the lithography properties. Alternatively, when $Rd^4$ is an aromatic group, the resist composition exhibits an excellent photoabsorption efficiency in a lithography process using EUV or the like as the exposure source, thereby resulting in the improvement of the sensitivity and the lithography properties.

In formula (d1-3), $Yd^1$ represents a single bond or a divalent linking group.

The divalent linking group for $Yd^1$ is not particularly limited, and examples thereof include a divalent hydrocarbon group (aliphatic hydrocarbon group, or aromatic hydrocarbon group) which may have a substituent and a divalent linking group containing a hetero atom. As such groups, the same divalent linking groups as those described above for $Ya^{21}$ in the formula (a2-1) can be mentioned.

As $Yd^1$, a carbonyl group, an ester bond, an amide bond, an alkylene group or a combination of these is preferable. As the alkylene group, a linear or branched alkylene group is more preferable, and a methylene group or an ethylene group is still more preferable.

Specific examples of preferable anion moieties for the component (d1-3) are shown below.

[Chemical Formula 61]

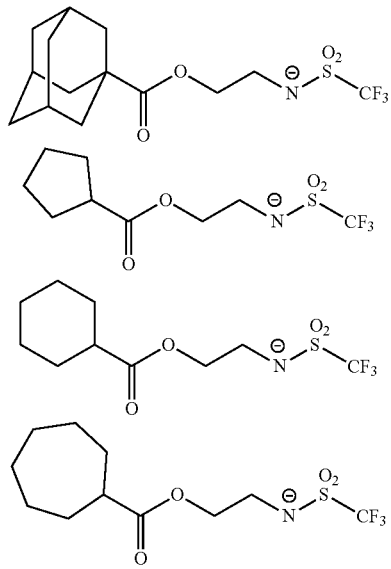

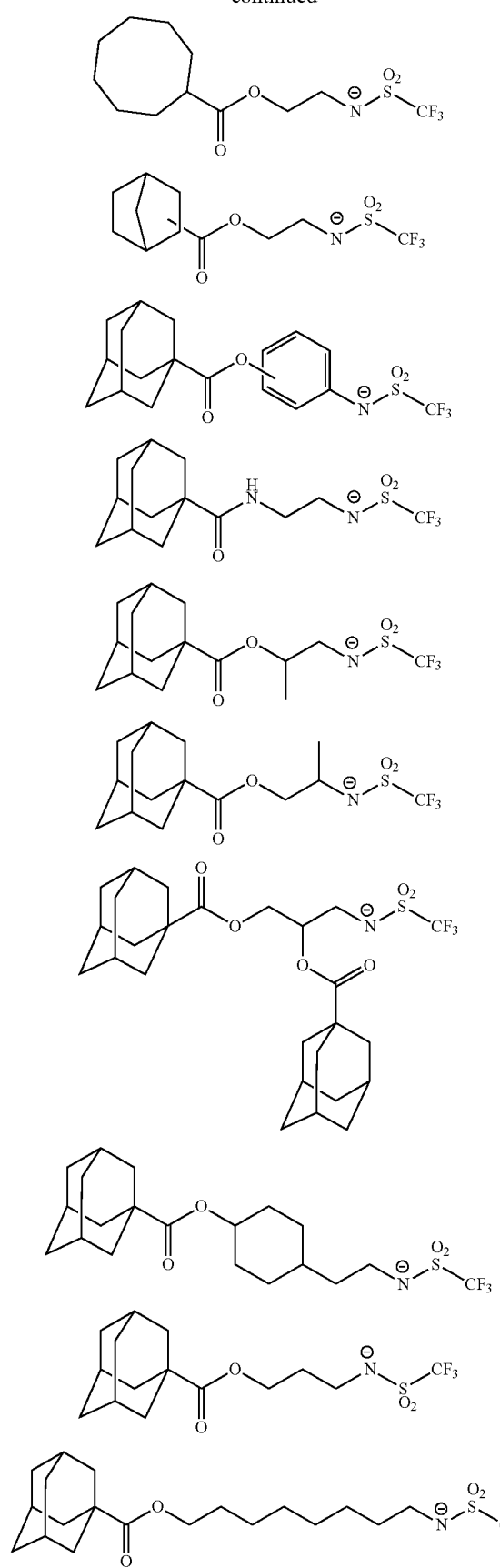
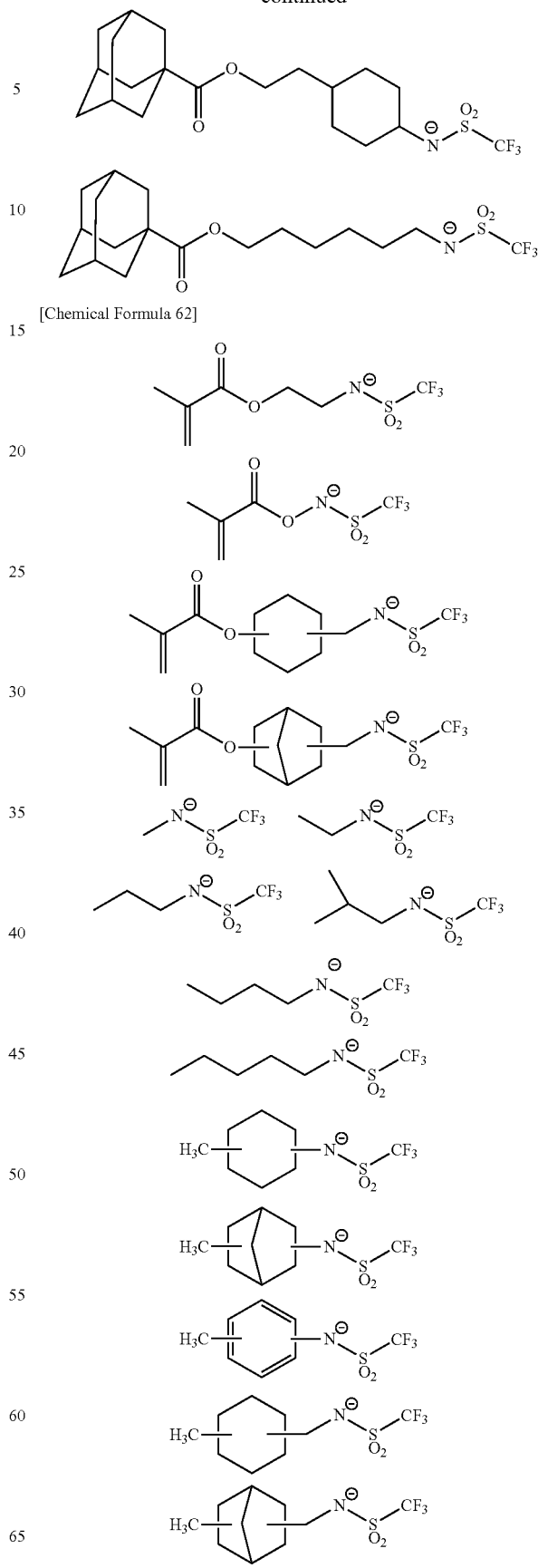

-continued

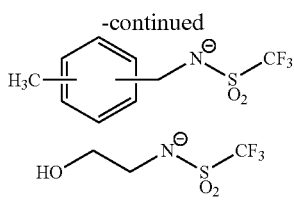

Cation Moiety

In formula (d1-3), $M^{m+}$ is an organic cation having a valency of m, and is the same as defined for $M^{m+}$ in the aforementioned formula (d1-1).

As the component (d1-3), one type of compound may be used, or two or more types of compounds may be used in combination.

As the component (D1), one type of the aforementioned components (d1-1) to (d1-3), or at least two types of the aforementioned components (d1-1) to (d1-3) can be used in combination.

The amount of the component (D1) relative to 100 parts by weight of the component (A) is preferably within a range from 0.5 to 10 parts by weight, more preferably from 0.5 to 8 parts by weight, and still more preferably from 1 to 8 parts by weight.

When the amount of the component (D1) is at least as large as the lower limit of the above-mentioned range, excellent lithography properties and excellent resist pattern shape can be obtained. On the other hand, when the amount of the component (D1) is no more than the upper limit of the above-mentioned range, sensitivity can be maintained at a satisfactory level, and through-put becomes excellent.

The production methods of the components (d1-1) and (d1-2) are not particularly limited, and the components (d1-1) and (d1-2) can be produced by conventional methods.

The amount of the component (D1) relative to 100 parts by weight of the component (A) is preferably within a range from 0.5 to 10.0 parts by weight, more preferably from 0.5 to 8.0 parts by weight, and still more preferably from 1.0 to 8.0 parts by weight. When the amount of at least as large as the lower limit of the above-mentioned range, excellent lithography properties and excellent resist pattern shape can be obtained. On the other hand, when the amount of the component (D) is no more than the upper limit of the above-mentioned range, sensitivity can be maintained at a satisfactory level, and through-put becomes excellent.

Component (D2)

The component (D) may contain a nitrogen-containing organic compound (D2) (hereafter, referred to as component (D2)) which does not fall under the definition of component (D1).

The component (D2) is not particularly limited, as long as it functions as an acid diffusion control agent, and does not fall under the definition of the component (D1). As the component (D2), any of the conventionally known compounds may be selected for use. Among these, an aliphatic amine, particularly a secondary aliphatic amine or tertiary aliphatic amine is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine)

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanolamine triacetate, and triethanolamine triacetate is preferable.

Further, as the component (D2), an aromatic amine may be used.

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonylpyrrolidine.

As the component (D2), one type of compound may be used alone, or two or more types may be used in combination.

The component (D2) is typically used in an amount within a range from 0.01 to 5.0 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

As the component (D), one type of compound may be used, or two or more types of compounds may be used in combination.

In the present embodiment, when the resist composition contains the component (D), the amount of the component (D) relative to 100 parts by weight of the component (A) is preferably within a range from 0.1 to 15 parts by weight, more preferably from 0.3 to 12 parts by weight, and still more preferably from 0.5 to 12 parts by weight.

When the amount of the component (D) is at least as large as the lower limit of the above-mentioned range, various lithography properties (such as LWR) of the resist composition are improved. Further, a resist pattern having an excellent shape can be obtained. On the other hand, when the amount of the component (D) is no more than the upper limit of the above-mentioned range, sensitivity can be maintained at a satisfactory level, and through-put becomes excellent.

Component (E):

Furthermore, in the resist composition of the present embodiment, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof may be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters and phenylphosphinic acid.

As the component (E), one type may be used alone, or two or more types may be used in combination.

The component (E) is typically used in an amount within a range from 0.01 to 5.0 parts by weight, relative to 100 parts by weight of the component (A).

Component (S):

In the present embodiment, the resist composition can be prepared by dissolving the materials for the resist composition in an organic solvent (hereafter, frequently referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples thereof include lactones such as γ-butyrolactone; ketones such as acetone, methyl ethyl ketone (MEK), cyclohexanone, methyl-n-pentyl ketone (2-heptanone), and methyl isopentyl ketone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

These solvents can be used individually, or in combination as a mixed solvent.

Among these, PGMEA, PGME, γ-butyrolactone and EL are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL or cyclohexanone is mixed as the polar solvent, the PGMEA:EL or cyclohexanone weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is appropriately adjusted to a concentration which enables coating of a coating solution to a substrate In general, the organic solvent is used in an amount such that the solid content of the resist composition becomes within the range from 1 to 20% by weight, and preferably from 2 to 15% by weight.

If desired, other miscible additives can also be added to the resist composition of the present invention. Examples of such miscible additives include additive resins for improving the performance of the resist film, dissolution inhibitors, plasticizers, stabilizers, colorants, halation prevention agents, and dyes.

(Method of Forming a Resist Pattern)

The method of forming a resist pattern according to the present embodiment includes: forming a resist film on a substrate using a resist composition of the aforementioned embodiment; conducting exposure of the resist film; and developing the resist film to form a resist pattern.

The method for forming a resist pattern according to the present embodiment can be performed, for example, as follows.

Firstly, a resist composition of the first aspect is applied to a substrate using a spinner or the like, and a bake treatment (post applied bake (PAB)) is conducted at a temperature of 80 to 150° C. for 40 to 120 seconds, preferably 60 to 90 seconds, to form a resist film.

Following selective exposure of the thus formed resist film, either by exposure through a mask having a predetermined pattern formed thereon (mask pattern) using an exposure apparatus such an electron beam lithography apparatus or an EUV exposure apparatus, or by patterning via direct irradiation with an electron beam without using a mask pattern, baking treatment (post exposure baking (PEB)) is conducted under temperature conditions of 80 to 150° C. for 40 to 120 seconds, and preferably 60 to 90 seconds.

Next, the resist film is subjected to a developing treatment. The developing treatment is conducted using an alkali developing solution in the case of an alkali developing process, and a developing solution containing an organic solvent (organic developing solution) in the case of a solvent developing process.

After the developing treatment, it is preferable to conduct a rinse treatment. The rinse treatment is preferably conducted using pure water in the case of an alkali developing process, and a rinse solution containing an organic solvent in the case of a solvent developing process.

In the case of a solvent developing process, after the developing treatment or the rinsing, the developing solution or the rinse liquid remaining on the pattern can be removed by a treatment using a supercritical fluid.

After the developing treatment or the rinse treatment, drying is conducted. If desired, bake treatment (post bake) can be conducted following the developing.

In this manner, a resist pattern can be formed.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present embodiment is effective to KrF excimer laser, ArF excimer laser, EB and EUV, and more effective to ArF excimer laser, EB and EUV, and most effective to EB and EUV.

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of the conventional organic solvents may be used which are capable of dissolving the component (A) (prior to exposure). Specific examples of the organic solvent include polar solvents such as ketone solvents, ester solvents, alcohol solvents, nitrile solvents, amide solvents and ether solvents, and hydrocarbon solvents.

A ketone solvent is an organic solvent containing C—C(=O)—C within the structure thereof. An ester solvent is an organic solvent containing C—C(=O)—O—C within the structure thereof. An alcohol solvent is an organic solvent containing an alcoholic hydroxy group in the structure thereof. An "alcoholic hydroxy group" refers to a hydroxy group bonded to a carbon atom of an aliphatic hydrocarbon group. A nitrile solvent is an organic solvent containing a nitrile group in the structure thereof. An amide solvent is an organic solvent containing an amide group within the structure thereof. An ether solvent is an organic solvent containing C—O—C within the structure thereof.

Some organic solvents have a plurality of the functional groups which characterizes the aforementioned solvents within the structure thereof. In such a case, the organic solvent can be classified as any type of the solvent having the characteristic functional group. For example, diethyleneglycol monomethylether can be classified as either an alcohol solvent or an ether solvent.

A hydrocarbon solvent consists of a hydrocarbon which may be halogenated, and does not have any substituent other than a halogen atom. Examples of the halogen atom include a fluorine atom, a chlorine atom, a bromine atom and an iodine atom, and a fluorine atom is preferable.

As the organic solvent contained in the organic developing solution, among these, a polar solvent is preferable, and ketone solvents, ester solvents and nitrile solvents are preferable.

Examples of ketone solvents include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonylalcohol, acetylcarbinol, acetophenone, methyl naphthyl ketone, isophorone, propylenecarbonate, γ-butyrolactone and methyl amyl ketone (2-heptanone). Among these examples, as a ketone solvent, methyl amyl ketone (2-heptanone) is preferable.

Examples of ester solvents include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate and propyl-3-methoxypropionate. Among these examples, as an ester solvent, butyl acetate is preferable.

Examples of nitrile solvents include acetonitrile, propionitrile, valeronitrile, butyronitrile and the like.

If desired, the organic developing solution may have a conventional additive blended. Examples of the additive include surfactants. The surfactant is not particularly limited, and for example, an ionic or non-ionic fluorine and/or silicon surfactant can be used.

As the surfactant, a non-ionic surfactant is preferable, and a non-ionic fluorine surfactant or a non-ionic silicon surfactant is more preferable.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in the case of a solvent developing process, any of the aforementioned organic solvents contained in the organic developing solution can be used which hardly dissolves the resist pattern. In general, at least one solvent selected from the group consisting of hydrocarbon solvents, ketone solvents, ester solvents, alcohol solvents, amide solvents and ether solvents is used. Among these, at least one solvent selected from the group consisting of hydrocarbon solvents, ketone solvents, ester solvents, alcohol solvents and amide solvents is preferable, more preferably at least one solvent selected from the group consisting of alcohol solvents and ester solvents, and an alcohol solvent is particularly desirable.

The alcohol solvent used for the rinse liquid is preferably a monohydric alcohol of 6 to 8 carbon atoms, and the monohydric alcohol may be linear, branched or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol and benzyl alcohol. Among these, 1-hexanol, 2-heptanol and 2-hexanol are preferable, and 1 hexanol and 2-hexanol are more preferable.

As the organic solvent, one kind of solvent may be used alone, or two or more kinds of solvents may be used in combination. Further, an organic solvent other than the aforementioned examples or water may be mixed together. However, in consideration of the development characteristics, the amount of water within the rinse liquid, based on the total amount of the rinse liquid is preferably 30% by weight or less, more preferably 10% by weight or less, still more preferably 5% by weight or less, and most preferably 3% by weight or less.

If desired, the rinse solution may have a conventional additive blended. Examples of the additive include surfactants. Examples of the additive include surfactants. As the surfactant, the same surfactants as those described above can be mentioned, a non-ionic surfactant is preferable, and a non-ionic fluorine surfactant or a non-ionic silicon surfactant is more preferable.

When a surfactant is added, the amount thereof based on the total amount of the rinse liquid is generally 0.001 to 5% by weight, preferably 0.005 to 2% by weight, and more preferably 0.01 to 0.5% by weight.

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

(Fluorine-Containing Polymeric Compound)

A third aspect of the present invention is a fluorine-containing polymeric compound having a structural unit (f1) derived from a compound represented by the aforementioned general formula (f1-1). The fluorine-containing polymeric compound is the same as defined for the component (F) in the first aspect.

The fluorine-containing polymeric compound according to the present embodiment may be preferably used as an additive in a resist composition for immersion exposure.

(Compound)

A fourth aspect of the present invention is a compound represented by general formula (f1-1) (hereafter, sometimes referred to as "compound (f1-1)"), and is the same as defined for the compound (f1-1) in the first aspect.

The compound according to the present embodiment is useful for producing the fluorine-containing polymeric compound of the third aspect.

(Production Method of Compound)

The compound (f1-1) according to the present embodiment may be obtained, for example, by reacting a compound (Car-1) represented by general formula (Car-1) with a compound (A1c-1) represented by general formula (A1c-1) in the presence of a base.

[Chemical Formula 63]

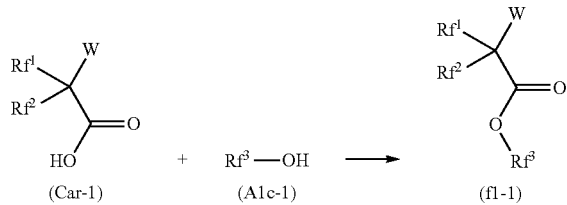

In general formula (Car-1), W, $Rf^{41}$ and $Rf^2$ are the same as defined for W, $Rf^1$ and $Rf^2$ in the aforementioned general formula (f1-1).

In general formula (A1c-1), $Rf^3$ is the same as defined for $Rf^3$ in the aforementioned general formula (f1-1).

As the compound (Car-1) and the compound (A1c-1), commercially available compounds may be used, or the compounds may be synthesized by a conventional method.

The reaction solvent may be any solvent which can dissolve the compounds (Car-1) and (A1c-1) and which do not react with the compounds. Examples of the reaction solvent include dichloromethane, dichloroethane, chloroform, tetrahydrofuran, N, N-dimethylformamide, acetonitrile and propionitrile.

Examples of the base include organic bases such as triethylamine, 4-dimethylaminopyridine (DMAP) and pyridine; and inorganic bases such as sodium hydride, $K_2CO_3$ and $Cs_2CO_3$.

Examples of condensation agents include carbodiimide reagents such as 1-ethyl-3-(3-dimethylaminopropyl)carbodiimide hydrochloride (WSC), ethyldiisopropylaminocarbodiimide hydrochloride (EDCI), dicyclohexylcarboxyimide (DCC), diisopropylcarbodiimide and carbodiimidazole; tetraethyl pyrophosphate; and benzotriazole-N-hydroxytrisdimethylaminophosphonium hexafluorophosphate (Bop reagent).

If desired, an acid may be used. As the acid, any acid generally used for dehydration/condensation may be used. Specific examples include inorganic acids such as hydrochloric acid, sulfuric acid and phosphoric acid; and organic acids such as methanesulfonic acid, trifluoromethanesulfonic acid, benzenesulfonic acid and p-toluenesulfonic acid. These acids can be used individually, or in a combination of two or more.

The amount of the compound (A1c-1) is preferably 1 to 3 equivalents, and more preferably 1 to 2 equivalents, based on the amount of the compound (Car-1).

The reaction temperature is preferably −20 to 40° C., more preferably 0 to 30° C.

The reaction time varies depending on factors such as the reactivity of the compound (Car-1) and the compound (A1c-1) and the reaction temperature. However, in general, the reaction time is preferably within a range from 30 to 480 minutes, and more preferably from 60 to 360 minutes.

The resist composition, the method of forming a resist pattern, the fluorine-containing polymeric compound and the compound according to the present embodiment described above is capable of achieving the effects of high water repellency and reducing generation of defects.

A resist film formed using the resist composition of the present embodiment contains the fluorine additive component (F) including the fluorine resin component (F1) having a structural unit (f1) derived from a compound represented by general formula (f1-1).

The structural unit (f1) contains a fluorine atom, and the ester bond "—C(=O)—O—" of the terminal group "—CO-OR$f^3$" is decomposed (hydrolyzed) by the action of a base (alkali developing solution) to form a hydrophilic group "—C(=O)—OH".

Therefore, as compared to a resist film formed using a resist composition which does not contain the component (F1), a resist film formed using a resist composition containing the component (F1) exhibits high hydrophobicity, and is decomposable in an alkali developing solution.

The expression "decomposable in an alkali developing solution" means that the group is decomposable by the action of an alkali developing solution (preferably decomposable by action of a 2.38% by weight aqueous solution of tetramethylammonium hydroxide (TMAH) at 23° C.), and exhibits increased alkali solubility in the alkali developing solution.

The component (F1) is hardly soluble in an alkali developing solution prior to being decomposed by the action of a base (alkali developing solution). When the component (F1) is decomposed by the action of an alkali developing solution, a carboxy group (hydrophilic group) is formed, and the solubility in a developing solution is increased.

According to the resist composition of the present embodiment containing the component (F1), in the formation of a resist pattern, a resist film may be formed which is hydrophobic prior to coming into contact with an alkali developing solution during immersion exposure or the like, and becomes hydrophilic during alkali developing.

By using a resist composition which exhibits enhanced hydrophilicity during alkali developing, generation of defects in (immersion) exposure (in particular, defects caused by deposited substance after developing process) can be effectively suppressed.

Especially in an immersion exposure process, it is preferable to enhance the hydrophobicity of the resist film so as to prevent the resist film from being affected by the immersion medium such as water. However, when the hydrophobicity of the resist film is high, it is disadvantageous in that the risk of defects caused by a deposit generated after the development process becomes high. The reason for this is that the deposit is a residue which could not be washed off the resist film by the hydrophilic developing solution and remaining on the resist film. Since this deposit is hydrophobic, the deposit becomes easier to be adhered to the resist film as the hydrophobicity of the resist film becomes higher.

In view of the above, the resist film is required to be hydrophobic during immersion exposure and become hydrophilic during alkali developing.

As described above, the fluorine-containing polymeric compound according to the present embodiment (component (F1)) is decomposed in an alkali developing solution. Therefore, the fluorine-containing polymeric compound according to the present embodiment is capable of forming a resist film which is hydrophobic prior to coming into contact with an alkali developing solution during immersion exposure or the like, and becomes hydrophilic during alkali developing.

The resist composition according to the present embodiment can effectively suppress generation of defects (in particular, defects caused by deposited substance after developing process), and is very useful in an immersion lithography process.

Further, a resist film formed using the resist composition according to the present embodiment exhibits higher hydrophobicity in immersion lithography than a conventional resist film. Therefore, the resist film formed using the resist composition according to the present embodiment exhibits an excellent water tracking ability which is required when immersion exposure is conducted using a scanning-type immersion exposure apparatus as described in Non-Patent Literature 1, and the scanning speed can be increased. In recent years, in the case where immersion lithography is conducted using a scan-type immersion lithography apparatus, due to the increase of the scanning speed, generation of watermark defects is becoming a problem. The resist composition according to the present embodiment is capable of exhibiting a satisfactory water repellency for responding to the increase in the scanning speed.

In a resist film formed using the resist composition according to the present embodiment, by virtue of using the component (F1), the hydrophobicity of the resist film is enhanced as compared to the case where a conventional resist composition is used, and the contact angles against water, e.g., the static contact angle (the contact angle between the surface of a water droplet on the resist film in a horizontal state and the resist film surface), the dynamic contact angle (the contact angle at which a water droplet starts to slide when the resist film is inclined, including the contact angle at the front-end point of the water droplet in the sliding direction (advancing angle) and the contact angle at the rear-end point of the water droplet in the sliding direction (receding angle)) and sliding angle (the inclination angle at which a water droplet starts to slide when the resist film is inclined) are changed. For example, the higher the hydrophobicity of a resist film, the higher the static contact angle and the dynamic contact angle and the smaller the sliding angle.

FIG. 1 is an explanatory diagram of an advancing angle ($\theta_1$), a receding angle ($\theta_2$) and a sliding angle ($\theta_3$).

As shown in FIG. 1, when a droplet 1 is placed on a plane 2 and the plane 2 is gradually inclined, the advancing angle is the angle $\theta_1$ formed between the lower end 1a of the droplet 1 and the plane 2 as the droplet 1 starts to move (slide) on the plane 2.

Further, at this point (the point when the liquid droplet 1 starts to move (slide) down the flat surface 2), the angle $\theta_2$ between the surface of the liquid droplet at the top edge 1b of the liquid droplet 1 and the flat surface 2 is the receding angle, and the inclination angle $\theta_3$ of the flat surface 2 is the sliding angle.

In the present description, the static contact angle, the dynamic contact angle and the sliding angle are measured in the following manner.

First, a resist composition solution is spin-coated onto a silicon substrate, and then heated under predetermined conditions, for example, at a temperature of 110° C. to 115° C. for 60 seconds to form a resist film.

Subsequently, the contact angles can be measured using commercially available measurement apparatuses such as DROP MASTER-700 (product name; manufactured by Kyowa Interface Science Co. Ltd.), AUTO SLIDING ANGLE: SA-30 DM (product name; manufactured by Kyowa Interface Science Co. Ltd.), and AUTO DISPENSER: AD-31 (product name; manufactured by Kyowa Interface Science Co. Ltd.).

With respect to the resist composition according to the present embodiment, the measured value of the receding angle of a resist film formed using the resist composition is not particularly limited, and is preferably 70 degrees)(° or more, and more preferably 80 to 105°. When the static contact angle is within the above-mentioned range, the hydrophobicity of the resist film surface becomes excellent, thereby enabling high-speed scanning during immersion exposure. Further, the effect of suppressing elution of a substance (leaching) can be improved. It is presumed that one of the main reasons why these effects can be achieved is related to the hydrophobicity of the resist film. More specifically, it is presumed that, since an aqueous substance such as water is used as the immersion medium, higher hydrophobicity has an influence on the swift removal of the immersion medium from the surface of the resist film after the immersion exposure.

For the same reasons as described above, with respect to a resist film formed using the resist composition according to the present embodiment, the receding angle as measured prior to conducting exposure and development is preferably 80° or more, more preferably 81° or more, and still more preferably 85° or more. The upper limit value of the receding angle is not particularly limited, and may be, for example, 90° or less.

Further, with respect to a resist film formed using the resist composition according to the present embodiment, the sliding angle as measured prior to exposure and development is preferably 25° or less, and more preferably 20° or less. When the sliding angle is no more than the upper limit of the above-mentioned range, the effect of suppressing the elution of a substance during immersion exposure is enhanced. The lower limit of the sliding angle is not particularly limited, and can be, for example, 5° or more.

Furthermore, with respect to a resist film formed using the resist composition according to the present embodiment, the advancing angle as measured prior to exposure and development is preferably 80 to 120°, and more preferably 80 to 110°. When the advancing angle is within the above-mentioned range, generation of defects can be suppressed, and various lithography properties can be improved.

The level of the above-mentioned various contact angles (static contact angle, dynamic contact angle and sliding angle) may be adjusted by the formulation of the resist composition, e.g., the kind of the component (F), the amount of the component (F), or the kind of the component (A1). For example, by increasing the amount of the component (F), the hydrophobicity of the formed resist film can be enhanced, and the static contact angle and the receding angle becomes large, in particular, the receding angle. Further, in particular, by adjusting the amount of the component (F) and the amount of fluorine contained in the structural unit(s), the advancing angle can be adjusted (the smaller the amount of fluorine, the smaller the advancing angle).

Moreover, the resist composition according to the present embodiment exhibits excellent storage stability over time. Some conventional fluorine additives had very high base dissociability, such that the fluorine additive was decomposed while storing the resist composition. In the resist composition according to the present embodiment, $Rf^3$ in the structural unit (f1) has a suitable electron-withdrawing property. Therefore, the structural unit (f1) is not decomposed during storage of the resist composition, and the structural unit (f1) exhibits a suitable electron-withdrawing property such that the structural unit (f1) is decomposed during alkali developing. For this reason, is presumed that the structural unit (f1) contributes to improvement in the storage stability of the resist composition over time.

In addition, by using the resist composition according to the present embodiment, elution of a substance (leaching) from the resist film during immersion exposure may be suppressed.

As described above, immersion exposure is a method in which exposure (immersion exposure) is conducted in a state where the region between the lens and the resist layer formed on a wafer (which was conventionally filled with air or an inert gas such as nitrogen) is filled with a solvent (an immersion medium) that has a larger refractive index than the refractive index of air. In immersion exposure, when the resist film comes into contact with the immersion medium, elution of substances within the resist film (component (B), component (D), and the like) into the immersion medium occurs. This elution of a substance causes phenomenon such as degeneration of the resist film and change in the refractive index of the immersion medium, thereby adversely affecting the lithography properties.

The amount of the eluted substance is affected by the properties of the resist film surface (e.g., hydrophilicity, hydrophobicity, and the like). Therefore, it is presumed that the amount of eluted substance can be reduced by enhancing the hydrophobicity of the resist film surface.

Since a resist film formed using the resist composition according to the present embodiment contains the component (F1), the hydrophobicity of the resist film prior to exposure and development is high as compared to the case where the resist film does not contain the component (F1). Therefore, according to the resist composition of the present embodiment, elution of substance during immersion exposure may be suppressed.

Since elution of substance may be suppressed, by using the resist composition according to the present embodiment, phenomenon such as degeneration of the resist film and change in the refractive index of the immersion medium, which occur during immersion exposure, may be suppressed. Further, as variation in the refractive index of the immersion medium can be suppressed, a resist pattern having an excellent shape can be formed. Furthermore, the level of contamination of the lens within the exposure apparatus can be lowered. Therefore, there is no need for protection against these disadvantages, and hence, the present invention can contribute to simplifying the process and the exposure apparatus.

In addition, a resist film formed using the resist composition according to the present embodiment hardly swells by water. Therefore, a very fine resist pattern may be formed with a high precision.

Also, the resist composition according to the present embodiment exhibits excellent lithography properties with respect to sensitivity, resolution, etching resistance and the like, and is capable of forming a resist pattern without any practical problems when used as a resist for immersion exposure. For example, by using a resist composition according to the present embodiment, a fine resist pattern having a size of 65 nm or less may be formed.

Thus, the resist composition according to the present embodiment not only is capable of suppressing generation of defects, but also exhibits excellent lithography properties which are generally required (such as sensitivity, resolution and etching resistance), and properties required for a resist material in immersion lithography (such as hydrophobicity, ability of suppressing elution of substance, and water tracking ability). Therefore, the resist composition according to the present embodiment is preferable for use in immersion exposure.

EXAMPLES

As follows is a description of examples of the present invention, although the scope of the present invention is by no way limited by these examples.

Monomer Synthesis Example: Example 1

23.17 g (108.24 mmol) of alcohol 1, 25.94 g (135.30 mmol) of 1-ethyl-3-(3-dimethylaminopropyl)carbodiimide hydrochloride (WSC) and 1.10 g (9.02 mmol) of 4-dimethylaminopuridine (DMAP) were dissolved in 306.8 g of dichloromethane ($CH_2Cl_2$). After cooling in an ice bath, 13.00 g (90.20 mmol) of carboxylic acid 1 dissolved in 130.0 g of dichloromethane was dropwise added, followed by stirring for 3 hours. The reaction liquid was added to 100 ml of a 5% aqueous HCl solution to stop the reaction, followed by washing the organic phase and concentration, so as to obtain 29.24 g of monomer 8 (yield: 95%).

[Chemical Formula 64]

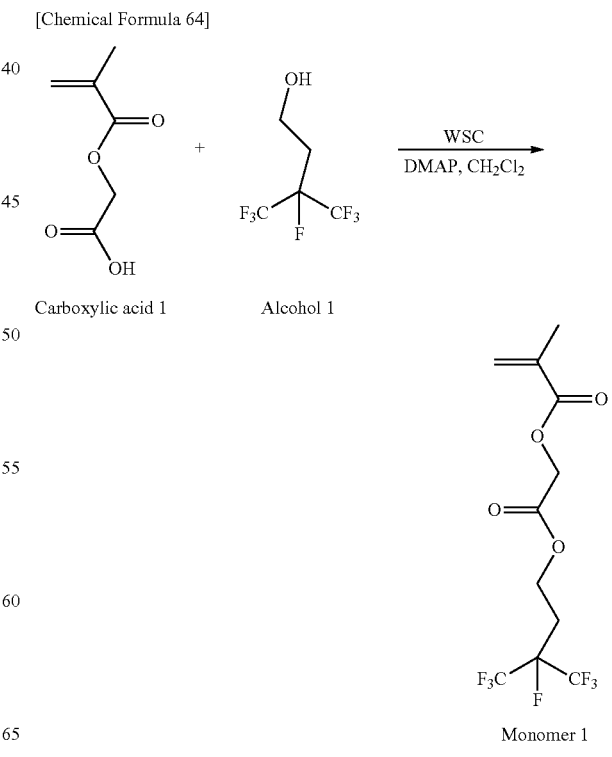

Monomer Synthesis Examples: Examples 2 to 9,
Comparative Examples 1 to 3

Monomers 2 to 12 were synthesized in the same manner as in Synthesis Example 1 using a carboxylic acid and an alcohol shown in Table 1.

TABLE 1

| | Monomer | Carboxylic acid | Alcohol |
|---|---|---|---|
| Example 1 | Monomer 1 | Carboxylic acid 1 | Alcohol 1 |
| Example 2 | Monomer 2 | Carboxylic acid 1 | Alcohol 2 |
| Example 3 | Monomer 3 | Carboxylic acid 1 | Alcohol 3 |
| Example 4 | Monomer 4 | Carboxylic acid 1 | Alcohol 4 |
| Example 5 | Monomer 5 | Carboxylic acid 2 | Alcohol 1 |
| Example 6 | Monomer 6 | Carboxylic acid 2 | Alcohol 2 |
| Example 7 | Monomer 7 | Carboxylic acid 2 | Alcohol 3 |
| Example 8 | Monomer 8 | Carboxylic acid 2 | Alcohol 4 |
| Example 9 | Monomer 9 | Carboxylic acid 2 | Alcohol 5 |
| Comparative Example 1 | Monomer 10 | Carboxylic acid 1 | Alcohol 6 |
| Comparative Example 2 | Monomer 11 | Carboxylic acid 2 | Alcohol 7 |
| Comparative Example 3 | Monomer 12 | Carboxylic acid 1 | Alcohol 5 |

[Chemical Formula 65]

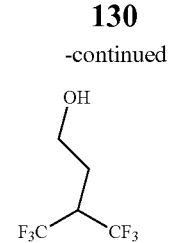

Carboxylic acid 1

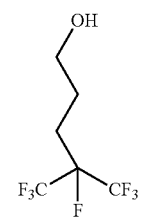

Carboxylic acid 2

[Chemical Formula 66]

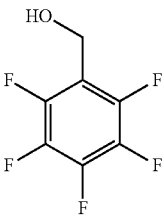

Alcohol 1

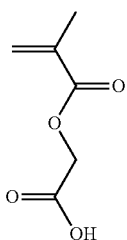

Alcohol 2

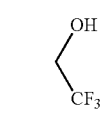

Alcohol 3

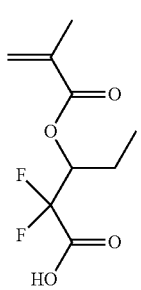

Alcohol 4

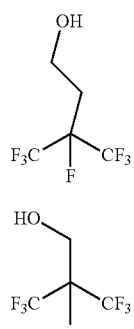

Alcohol 5

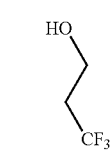

Alcohol 6

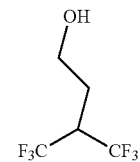

Alcohol 7

[Chemical Formula 67]

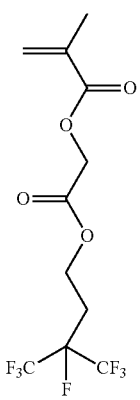

Monomer 1

Monomer 2
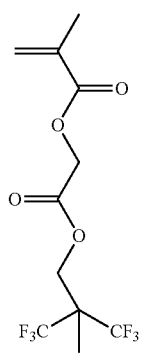
Monomer 3
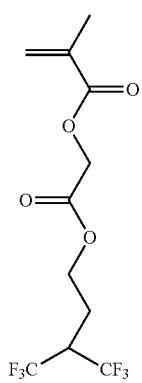
Monomer 4
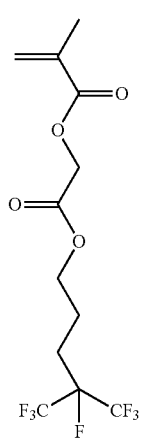
Monomer 5
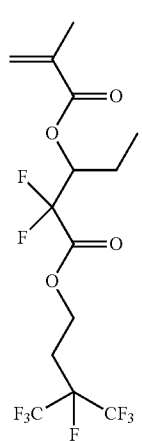
Monomer 6
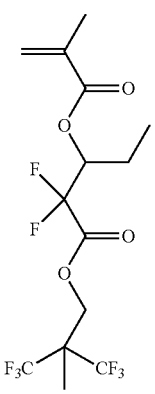
Monomer 7
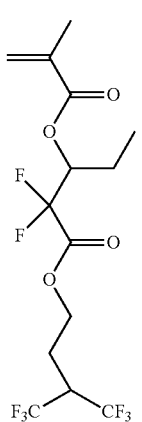
Monomer 8
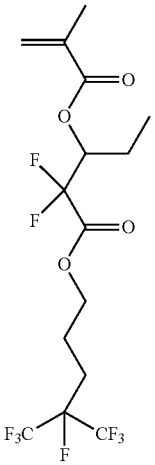

Monomer 9

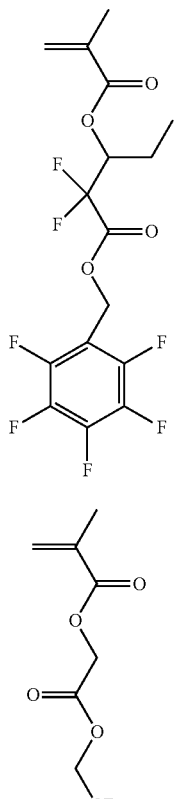

Monomer 10

Monomer 11

Monomer 12

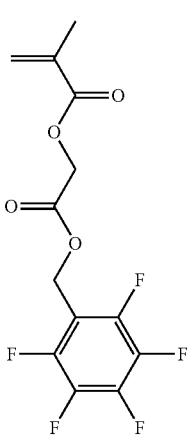

Synthesis Examples of Fluorine-Containing Polymer: Examples 10 to 18, Comparative Examples 4 to 6

A monomer shown in Table 2 was polymerized by a conventional method, so as to obtain fluorine-containing polymers (F)-1 to (F)-12. The weight average molecular weight (Mw) and the molecular weight dispersity (Mw/Mn) determined by the polystyrene equivalent value as measured by gel permeation chromatography (GPC) and the compositional ratios (ratio (molar ratio) of the respective structural units within the structural formula) of the copolymers as measured by $^{13}$C-NMR are shown in Table 2.

TABLE 2

| | Fluorine-containing polymer | Monomer | Mw | Mw/Mn |
|---|---|---|---|---|
| Example 10 | (F)-1 | Monomer 1 | 14,700 | 1.59 |
| Example 11 | (F)-2 | Monomer 2 | 18,100 | 1.63 |
| Example 12 | (F)-3 | Monomer 3 | 16,100 | 1.66 |
| Example 13 | (F)-4 | Monomer 4 | 15,500 | 1.52 |
| Example 14 | (F)-5 | Monomer 5 | 15,900 | 1.48 |
| Example 15 | (F)-6 | Monomer 6 | 19,200 | 1.59 |
| Example 16 | (F)-7 | Monomer 7 | 16,300 | 1.66 |
| Example 17 | (F)-8 | Monomer 8 | 17,400 | 1.73 |
| Example 18 | (F)-9 | Monomer 9 | 18,700 | 1.57 |
| Comparative Example 4 | (F)-10 | Monomer 10 | 19,200 | 1.72 |
| Comparative Example 5 | (F)-11 | Monomer 11 | 19,800 | 1.65 |
| Comparative Example 6 | (F)-12 | Monomer 12 | 18,200 | 1.78 |

<Production of Resist Composition>

The components shown in Table 3 were mixed together and dissolved to obtain each resist composition.

TABLE 3

| | Component (A) | Component (B) | Component (D) | Component (E) | Component (F) | Component (S) | |
|---|---|---|---|---|---|---|---|
| Ex. 19 | (A)-1 [100] | (B)-1 [9.0] | (D)-1 [4.5] | (E)-1 [1.0] | (F)-1 [3.0] | (S)-1 [100] | (S)-2 [3330] |
| Ex. 20 | (A)-1 [100] | (B)-1 [9.0] | (D)-1 [4.5] | (E)-1 [1.0] | (F)-2 [3.0] | (S)-1 [100] | (S)-2 [3330] |
| Ex. 21 | (A)-1 [100] | (B)-1 [9.0] | (D)-1 [4.5] | (E)-1 [1.0] | (F)-3 [3.0] | (S)-1 [100] | (S)-2 [3330] |
| Ex. 22 | (A)-1 [100] | (B)-1 [9.0] | (D)-1 [4.5] | (E)-1 [1.0] | (F)-4 [3.0] | (S)-1 [100] | (S)-2 [3330] |
| Ex. 23 | (A)-1 [100] | (B)-1 [9.0] | (D)-1 [4.5] | (E)-1 [1.0] | (F)-5 [3.0] | (S)-1 [100] | (S)-2 [3330] |
| Ex. 24 | (A)-1 [100] | (B)-1 [9.0] | (D)-1 [4.5] | (E)-1 [1.0] | (F)-6 [3.0] | (S)-1 [100] | (S)-2 [3330] |
| Ex. 25 | (A)-1 [100] | (B)-1 [9.0] | (D)-1 [4.5] | (E)-1 [1.0] | (F)-7 [3.0] | (S)-1 [100] | (S)-2 [3330] |
| Ex. 26 | (A)-1 [100] | (B)-1 [9.0] | (D)-1 [4.5] | (E)-1 [1.0] | (F)-8 [3.0] | (S)-1 [100] | (S)-2 [3330] |
| Ex. 27 | (A)-1 [100] | (B)-1 [9.0] | (D)-1 [4.5] | (E)-1 [1.0] | (F)-9 [3.0] | (S)-1 [100] | (S)-2 [3330] |
| Comp. Ex. 7 | (A)-1 [100] | (B)-1 [9.0] | (D)-1 [4.5] | (E)-1 [1.0] | (F)-10 [3.0] | (S)-1 [100] | (S)-2 [3330] |
| Comp. Ex. 8 | (A)-1 [100] | (B)-1 [9.0] | (D)-1 [4.5] | (E)-1 [1.0] | (F)-11 [3.0] | (S)-1 [100] | (S)-2 [3330] |
| Comp. Ex. 9 | (A)-1 [100] | (B)-1 [9.0] | (D)-1 [4.5] | (E)-1 [1.0] | (F)-12 [3.0] | (S)-1 [100] | (S)-2 [3330] |

In Table 3, the reference characters indicate the following. The values in brackets [ ] indicate the amount (in terms of parts by weight) of the component added.

(A)-1: Polymeric compound represented by chemical formula (A)-1 shown below. The weight average weight (Mw) and the dispersity (Mw/Mn) in terms of the polystyrene equivalent value measured by gel permeation chromatography (GPC) were 10,000 and 1.72, respectively. The composition of the copolymer (ratio (molar ratio) of the respective structural units within the structural formula) as determined by $^{13}$C-NMR was l/m/n=40/40/20.

(B)-1: an acid generator represented by chemical formula (B)-1 shown below (D)-1: acid diffusion control agent represented by chemical formula (D)-1 below (E)-1: salicylic acid (F)-1 to (F)-12: fluorine-containing polymers (F)-1 to (F)-12

(S)-1: γ-butyrolactone (S)-2: a mixed solvent of propylene glycol monomethyl ether acetate/propylene glycol monomethyl ether/cyclohexane=45/30/25 (weight ratio)

[Chemical Formula 68]

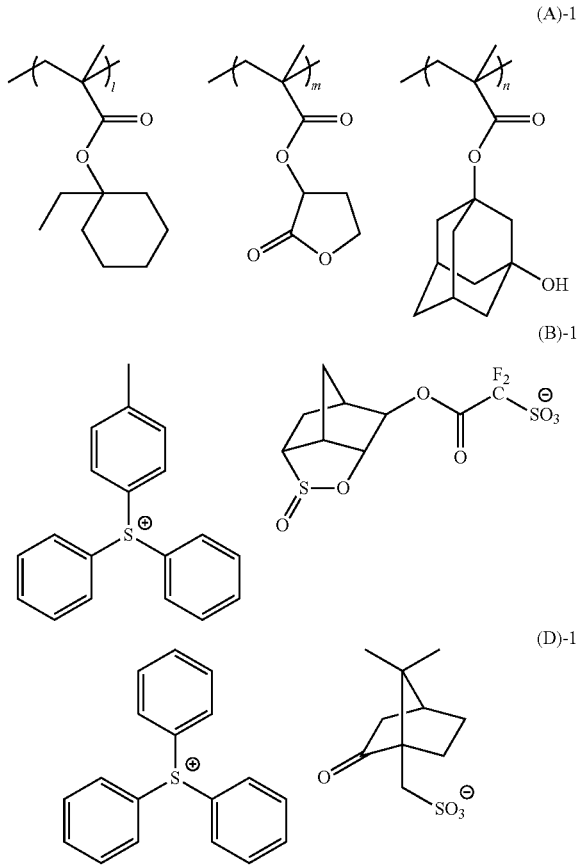

<Evaluation of Contact Angle (1)>

Each of the resist compositions of Examples 19 to 27 and Comparative Example 7 to 9 was applied to a silicon wafer using a spinner, and was then prebaked (PAB) on a hotplate at 120° C. for 60 seconds and dried, so as to form a resist film having a film thickness of 100 nm.

A water droplet was dripped onto the surface of each resist film, and a DROP MASTER-700 apparatus (product name; manufactured by Kyowa Interface Science Co. Ltd.) was used to measure the contact angle (receding angle) (contact angle measurement: water 50 μl). The results are shown in Table 4.

<Formation of Resist Pattern (1)>

An organic anti-reflection film composition (product name: ARC-29A, manufactured by Brewer Science Ltd.) was applied to an 12-inch silicon wafer using a spinner, and the composition was then baked at 205° C. for 60 seconds, thereby forming an organic anti-reflection film having a film thickness of 89 nm.

Then, each of the resist compositions of Examples 19 to 27 and Comparative Examples 7 to 9 was applied to the organic antireflection film, and was then prebaked (PAB) on a hotplate at 120° C. for 60 seconds and dried, so as to form a resist film having a film thickness of 100 nm.

Subsequently, the resist film was selectively irradiated with an ArF excimer laser (193 nm) through a mask, using an immersion lithography ArF exposure apparatus NSR-S609B (manufactured by Nikon Corporation; Cross-pole (0.98/0.78) w/P; immersion medium: water).

Then, a post exposure bake (PEB) treatment was conducted at 100° C. for 60 seconds.

Thereafter, alkali developing was conducted for 10 seconds using a 2.38 wt % aqueous tetramethylammonium hydroxide (TMAH) solution "NMD-3" (product name; manufactured by Tokyo Ohka Kogyo Co., Ltd.) at 23° C.

As a result, in each of the examples, a line and space pattern (LS pattern) having a line width of 50 nm and a pitch of 100 nm was formed.

<Evaluation of Defects at Unexposed Portions (1)>

The LS pattern obtained in the above "Formation of resist pattern (1)" was observed using a surface defect inspection device KLA2371 (a product name) manufactured by KLA Tencor Corporation. The number of development defects at unexposed portions per one silicon wafer was measured, and evaluation was made in accordance with the following criteria. The results are shown in Table 4.

(Criteria)

A: The number of development defect was less than 1,000.

B: The number of development defects was less than 10,000

C: The number of development defects was 10,000 or more

<Evaluation of Storage Stability Over Time (1)>

Each of the resist compositions of Examples 19 to 27 and Comparative Examples 7 to 9 were stored at room temperature for 3 month.

With respect to the resist composition stored for 3 month, the storage stability of the resist composition over time was evaluated in accordance with the following criteria. The results are shown in Table 4.

(Criteria)

A: No change in sensitivity (less than 1 mJ/cm$^2$)

B: Change in sensitivity (1 mJ/cm$^2$ or more)

TABLE 4

|  | Receding angle (°) | Defect | Storage stability over time |
| --- | --- | --- | --- |
| Example 19 | 81.2 | A | A |
| Example 20 | 80.3 | A | A |
| Example 21 | 80.5 | A | A |
| Example 22 | 81.5 | B | A |
| Example 23 | 86.5 | B | A |
| Example 24 | 86.0 | B | A |
| Example 25 | 86.2 | B | A |
| Example 26 | 86.5 | B | A |
| Example 27 | 85.9 | B | A |
| Comparative Example 7 | 70.0 | A | A |

TABLE 4-continued

|  | Receding angle (°) | Defect | Storage stability over time |
|---|---|---|---|
| Comparative Example 8 | 78.4 | B | B |
| Comparative Example 9 | 68.7 | C | A |

As seen from the results shown in Table 4, it was confirmed that the resist compositions of Examples 19 to 27 which applied the present invention had a larger receding angle than the resist compositions of Comparative Examples 7 to 9. Therefore, the resist compositions of Examples 19 to 27 which applied the present invention are expected to reduce water mark defects.

Further, it was confirmed that the resist compositions of Examples 19 to 27 which applied the present invention had defects reduced at unexposed portions.

Furthermore, it was confirmed that the resist compositions of Examples 19 to 27 had excellent storage stability over time.

Synthesis Examples of Fluorine-Containing Polymeric Compound: Examples 28 to 37

Monomers shown in Table 5 were polymerized by a conventional method, so as to obtain fluorine-containing polymeric compounds (F)-13 to (F)-22. The weight average molecular weight (Mw) and the molecular weight dispersity (Mw/Mn) determined by the polystyrene equivalent value as measured by gel permeation chromatography (GPC) and the compositional ratios (ratio (molar ratio) of the respective structural units within the structural formula) of the copolymers as measured by $^{13}$C-NMR are shown in Table 5.

TABLE 5

|  | Fluorine-containing polymer | Monomer (Molar ratio) | Mw | Mw/Mn |
|---|---|---|---|---|
| Example 28 | (F)-13 | Monomer 6/Monomer 13 (80/20) | 17,600 | 1.68 |
| Example 29 | (F)-14 | Monomer 6/Monomer 14 (80/20) | 18,500 | 1.69 |
| Example 30 | (F)-15 | Monomer 6/Monomer 15 (80/20) | 16,100 | 1.67 |
| Example 31 | (F)-16 | Monomer 6/Monomer 16 (80/20) | 16,400 | 1.70 |
| Example 32 | (F)-17 | Monomer 6/Monomer 13 (50/50) | 16,500 | 1.77 |
| Example 33 | (F)-18 | Monomer 5/Monomer 13 (80/20) | 17,300 | 1.63 |
| Example 34 | (F)-19 | Monomer 2/Monomer 13 (80/20) | 19,200 | 1.76 |
| Example 35 | (F)-20 | Monomer 1/Monomer 14 (80/20) | 18,000 | 1.64 |
| Example 36 | (F)-21 | Monomer 2/Monomer 15 (50/50) | 18,800 | 1.71 |
| Example 37 | (F)-22 | Monomer 1/Monomer 13 (80/20) | 17,500 | 1.63 |

[Chemical Formula 69]

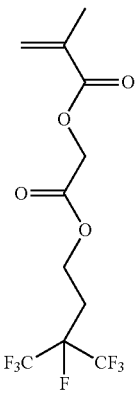

Monomer 1

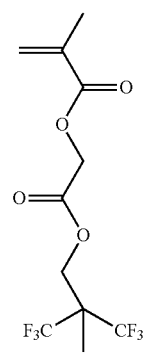

Monomer 2

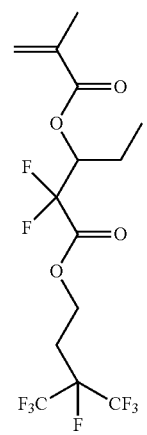

Monomer 5

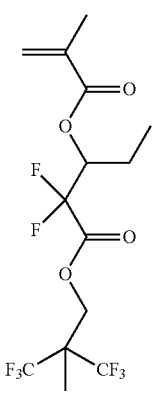

Monomer 6

Monomer 13

Monomer 14

Monomer 15

Monomer 16

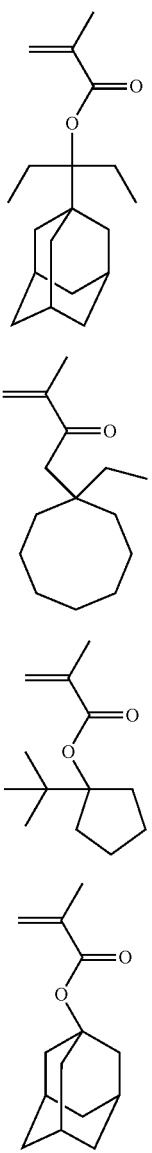

<Production of Resist Composition>

The components shown in Table 6 were mixed together and dissolved to obtain each resist composition.

TABLE 6

| | Component (A) | Component (B) | Component (D) | Component (E) | Component (F) | Component (S) | |
|---|---|---|---|---|---|---|---|
| Ex. 38 | (A)-1 [100] | (B)-1 [9.0] | (D)-1 [4.5] | (E)-1 [1.0] | (F)-13 [3.0] | (S)-1 [100] | (S)-2 [3330] |
| Ex. 39 | (A)-1 [100] | (B)-1 [9.0] | (D)-1 [4.5] | (E)-1 [1.0] | (F)-14 [3.0] | (S)-1 [100] | (S)-2 [3330] |
| Ex. 40 | (A)-1 [100] | (B)-1 [9.0] | (D)-1 [4.5] | (E)-1 [1.0] | (F)-15 [3.0] | (S)-1 [100] | (S)-2 [3330] |
| Ex. 41 | (A)-1 [100] | (B)-1 [9.0] | (D)-1 [4.5] | (E)-1 [1.0] | (F)-16 [3.0] | (S)-1 [100] | (S)-2 [3330] |
| Ex. 42 | (A)-1 [100] | (B)-1 [9.0] | (D)-1 [4.5] | (E)-1 [1.0] | (F)-17 [3.0] | (S)-1 [100] | (S)-2 [3330] |
| Ex. 43 | (A)-1 [100] | (B)-1 [9.0] | (D)-1 [4.5] | (E)-1 [1.0] | (F)-18 [3.0] | (S)-1 [100] | (S)-2 [3330] |
| Ex. 44 | (A)-1 [100] | (B)-1 [9.0] | (D)-1 [4.5] | (E)-1 [1.0] | (F)-19 [3.0] | (S)-1 [100] | (S)-2 [3330] |
| Ex. 45 | (A)-1 [100] | (B)-1 [9.0] | (D)-1 [4.5] | (E)-1 [1.0] | (F)-20 [3.0] | (S)-1 [100] | (S)-2 [3330] |
| Ex. 46 | (A)-1 [100] | (B)-1 [9.0] | (D)-1 [4.5] | (E)-1 [1.0] | (F)-21 [3.0] | (S)-1 [100] | (S)-2 [3330] |
| Ex. 47 | (A)-1 [100] | (B)-1 [9.0] | (D)-1 [4.5] | (E)-1 [1.0] | (F)-22 [3.0] | (S)-1 [100] | (S)-2 [3330] |

In Table 6, the reference characters indicate the following. The values in brackets indicate the amount (in terms of parts by weight) of the component added.

(A)-1: Polymeric compound represented by the aforementioned chemical formula (A)-1

(B)-1: an acid generator represented by the aforementioned chemical formula (B)-1

(D)-1: acid diffusion control agent represented by the aforementioned chemical formula (D)-1

(E)-1: salicylic acid (F)-13 to (F)-22: fluorine-containing polymers (F)-13 to (F)-22

(S)-1: γ-butyrolactone (S)-2: a mixed solvent of propylene glycol monomethyl ether acetate/propylene glycol monomethyl ether/cyclohexane=45/30/25 (weight ratio)

<Evaluation of Contact Angle (2)>

The contact angle (receding angle) of each of the resist compositions of Examples 38 to 47 were measured in the same manner as in the aforementioned "Evaluation of contact angle (1)". The results are shown in Table 7.

<Formation of Resist Pattern (2)>

Using the resist compositions of Examples 38 to 47, resist patterns were formed in the same manner as in the aforementioned "Formation of resist pattern (1)".

As a result, in each of the examples, a line and space pattern (LS pattern) having a line width of 50 nm and a pitch of 100 nm was formed.

<Evaluation of Defects at Unexposed Portions (2)>

The LS patterns obtained in the above "Formation of resist pattern (2)" was observed using a surface defect inspection device KLA2371 (a product name) manufactured by KLA Tencor Corporation. The number of development defects at unexposed portions per one silicon wafer was measured, and evaluation was made in accordance with the following criteria. The results are shown in Table 7.

(Criteria)

A: The number of development defect was less than 1,000.

B: The number of development defects was less than 10,000

C: The number of development defects was 10,000 or more

<Evaluation of Storage Stability Over Time (2)>

The storage stability of the resist compositions of Examples 38 to 47 over time were evaluated in the same manner as in the aforementioned "Evaluation of storage stability over time (1)". The results are shown in Table 7.

TABLE 7

| | Receding angle (°) | Defect | Storage stability over time |
|---|---|---|---|
| Example 38 | 86.8 | B | A |
| Example 39 | 86.2 | B | A |

TABLE 7-continued

|  | Receding angle (°) | Defect | Storage stability over time |
|---|---|---|---|
| Example 40 | 86.7 | B | A |
| Example 41 | 86.5 | B | A |
| Example 42 | 87.5 | B | A |
| Example 43 | 86.7 | B | A |
| Example 44 | 81.8 | A | A |
| Example 45 | 80.9 | A | A |
| Example 46 | 82.0 | A | A |
| Example 47 | 81.5 | A | A |

As seen from the results shown in Table 7, it was confirmed that the resist compositions of Examples 38 to 47 which applied the present invention had a large receding angle. Therefore, the resist compositions of Examples 38 to 47 which applied the present invention are expected to reduce water mark defects.

Further, it was confirmed that the resist compositions of Examples 38 to 47 which applied the present invention had defects reduced at unexposed portions.

Furthermore, it was confirmed that the resist compositions of Examples 38 to 47 had excellent storage stability over time.

What is claimed is:

1. A resist composition which generates acid upon exposure and exhibits changed solubility in a developing solution under action of acid, the resist composition comprising:
    a base component (A) which exhibits changed solubility in a developing solution under action of acid, an acid generator component (B) which generates acid upon exposure, and a fluorine additive component (F) which exhibits decomposability to an alkali developing solution,
    the fluorine additive component (F) comprising a fluorine resist component (F1) comprising a structural unit (f1) derived from a compound represented by general formula (f1-1-1) or (f1-1-2) shown below:

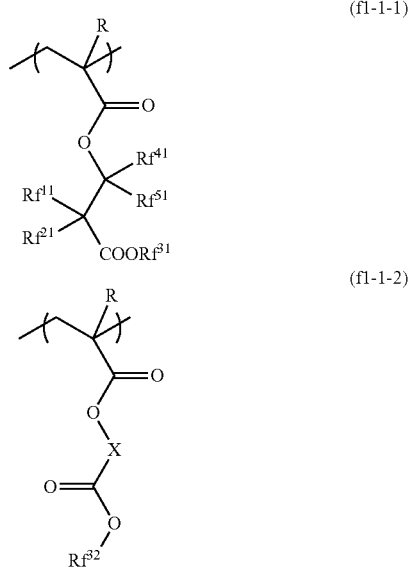

wherein each R independently represents a hydrogen atom, an alkyl group of 1 to 5 carbon atoms or a halogenated alkyl group of 1 to 5 carbon atoms; $Rf^{11}$ and $Rf^{21}$ each independently represents a hydrogen atom or an electron-withdrawing group; provided that at least one of $Rf^{11}$ and $Rf^{21}$ is an electron-withdrawing group; $Rf^{31}$ is a hydrocarbon group of 5 or more carbon atoms represented by general formula (f1-r-1) shown below, or an aromatic hydrocarbon group selected from a benzyl group, a phenethyl group, a 1-naphthylmethyl group, a 2-naphthylmethyl group, a 1-naphthylethyl group or a 2-naphthylethyl group; in the case where $Rf^{31}$ is an aromatic hydrocarbon group, 3 or more hydrogen atoms of the aromatic ring are substituted with electron-withdrawing groups, and at least one of $Rf^{11}$ and $Rf^{31}$ has a fluorine atom; $Rf^{41}$ and $Rf^{51}$ a hydrogen atom, an alkyl group or a fluorinated alkyl group; X represents a divalent linking group having no acid dissociable portion; and $Rf^{32}$ is a hydrocarbon group of 5 or more carbon atoms represented by general formula (f1-r-1) shown below,

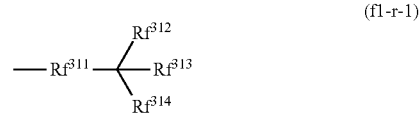

wherein $Rf^{311}$ represents an alkylene group; $Rf^{312}$ to $Rf^{314}$ each independently represents a hydrogen atom, an alkyl group, a fluorine atom or a fluorinated alkyl group; provided that at least one of $Rf^{312}$ to $Rf^{314}$ is a fluorine atom or a fluorinated alkyl group.

2. A method of forming a resist pattern, comprising:
    forming a resist film on a substrate using the resist composition according to claim 1;
    exposing the resist film; and
    developing the exposed resist film to form a resist pattern.

3. A fluorine-containing polymeric compound comprising a structural unit (f1) derived from a compound represented by general formula (f1-1-1) or (f1-1-2) shown below:

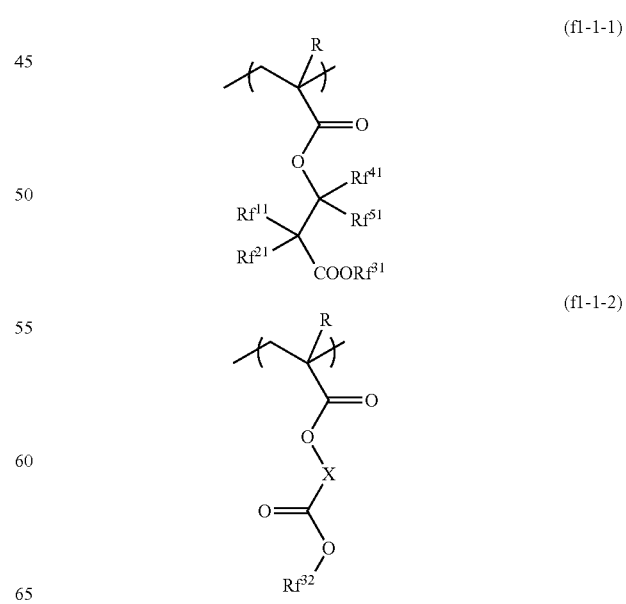

wherein each R independently represents a hydrogen atom, an alkyl group of 1 to 5 carbon atoms or a halogenated alkyl group of 1 to 5 carbon atoms; $Rf^{11}$ and $Rf^{21}$ each independently represents a hydrogen atom or an electron-withdrawing group; provided that at least one of $Rf^{11}$ and $Rf^{21}$ is an electron-withdrawing group; $Rf^{31}$ is a hydrocarbon group of 5 or more carbon atoms represented by general formula (f1-r-1) shown below, or an aromatic hydrocarbon group selected from a benzyl group, a phenethyl group, a 1-naphthylmethyl group, a 2-naphthylmethyl group, a 1-naphthylethyl group or a 2-naphthylethyl group; in the case where $Rf^{31}$ is an aromatic hydrocarbon group, 3 or more hydrogen atoms of the aromatic ring are substituted with electron-withdrawing groups, and at least one of $Rf^{11}$ and $Rf^{31}$ has a fluorine atom; $Rf^{41}$ and $Rf^{51}$ a hydrogen atom, an alkyl group or a fluorinated alkyl group; X represents a divalent linking group having no acid dissociable portion; and $Rf^{32}$ is a hydrocarbon group of 5 or more carbon atoms represented by general formula (f1-r-1) shown below,

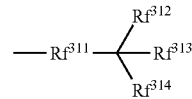

(f1-r-1)

wherein $Rf^{311}$ represents an alkylene group; $Rf^{312}$ to $Rf^{314}$ each independently represents a hydrogen atom, an alkyl group, a fluorine atom or a fluorinated alkyl group; provided that at least one of $Rf^{312}$ to $Rf^{314}$ is a fluorine atom or a fluorinated alkyl group.

4. The resist composition according to claim 1, wherein $Rf^{31}$ in general formula (f1-1-1) is a hydrocarbon group of 5 or more carbon atoms represented by general formula (f1-r-1).

5. The fluorine-containing polymeric compound according to claim 3, wherein $Rf^{31}$ in general formula (f1-1-1) is a hydrocarbon group of 5 or more carbon atoms represented by general formula (f1-r-1).

* * * * *

UNITED STATES PATENT AND TRADEMARK OFFICE
CERTIFICATE OF CORRECTION

PATENT NO. : 10,838,301 B2  Page 1 of 2
APPLICATION NO. : 15/928488
DATED : November 17, 2020
INVENTOR(S) : Tomoyuki Hirano and Takaaki Kaiho It is certified that error appears in the above-identified patent and that said Letters Patent is hereby corrected as shown below:

On the Title Page

In Column 2, item (57), Abstract, Line 13, delete "group" and insert -- group. --.

In the Specification

In Column 7, Line 34, delete "(B)";" and insert -- (B)"); --.
In Column 8, Line 23, delete "(A1))"" and insert -- (A1)") --.
In Column 12, Line 40, delete "substituted;" and insert -- substituted. --.
In Column 14, Line 19, delete "substituted;" and insert -- substituted. --.
In Column 27, Line 51, delete "Ra'" and insert -- Ra¹ --.

In Column 31, Lines 48-57 (approx.), delete " 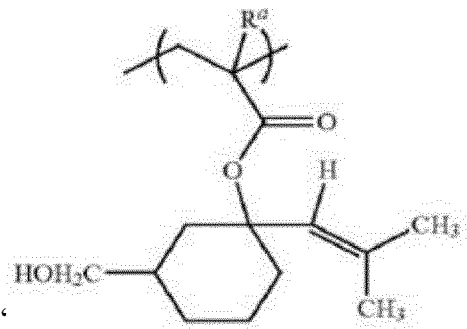 " and insert

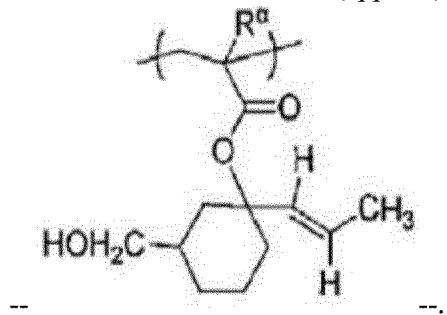

--.

Signed and Sealed this
Twenty-third Day of March, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)

In Column 51, Lines 45-49 (approx.), delete " 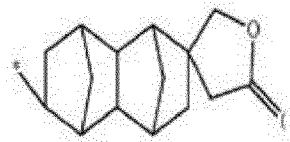 " and insert

-- --.

In Column 64, Line 46, delete "(electrons," and insert -- electrons, --.
In Column 65, Line 44, delete "0" and insert -- O --.
In Column 66, Lines 12-13, delete "O]m″″" and insert -- O]$_m$″ --.
In Column 72, Lines 50-51, delete "polycycic cycloolefine" and insert -- polycyclic cycloolefin --.
In Column 73, Line 22, delete "the a" and insert -- a --.
In Column 73, Line 63, delete "RV" and insert -- Rf$^3$ --.
In Column 76, Line 56, delete "has is the" and insert -- is the --.
In Column 88, Line 61, delete "R$^{104}$" and insert -- R$^{101}$ --.
In Column 92, Line 2, delete "R$^{104}$" and insert -- R$^{101}$ --.
In Column 115, Line 67, delete "amines" and insert -- amines. --.
In Column 116, Line 12 (approx.), delete "octanolamine" and insert -- octanolamine. --.
In Column 123, Line 38, delete "RF$^{41}$" and insert -- Rf$^1$ --.
In Column 126, Line 22, delete ")(°" and insert -- (°) --.
In Column 128, Lines 27-28, delete "dimethylaminopuridine" and insert -- dimethylaminopyridine --.
In Column 136, Line 39, delete "10,000" and insert -- 10,000. --.

In Column 139, Lines 16-25 (approx.), delete "  " and insert -- --.
In Column 140, Line 13 (approx.), delete "brackets" and insert -- brackets [ ] --.
In Column 140, Line 52, delete "10,000" and insert -- 10,000. --.
In Column 140, Line 54, delete "more" and insert -- more. --.

In the Claims

In Column 142, Line 12 (approx.), Claim 1, delete "Rf$^{51}$a" and insert -- Rf$^{51}$ a --.
In Column 143, Lines 7-8, Claim 3, delete "(f1- r-1)" and insert -- (f1-r-1) --.
In Column 143, Line 20, Claim 3, delete "(f1- r-1)" and insert -- (f1-r-1) --.